US007432257B2

(12) United States Patent
Coats et al.

(10) Patent No.: US 7,432,257 B2
(45) Date of Patent: Oct. 7, 2008

(54) PIPERDINYL-PHENOXAZINE AND PHENOTHIAZINE DERIVATIVES AS δ-OPIOID MODULATORS

(75) Inventors: Steve J. Coats, Quakertown, PA (US); Scott L. Dax, Landenberg, PA (US); Bart DeCorte, Southhampton, PA (US); Li Liu, Doylestown, PA (US); Mark McDonnell, Lansdale, PA (US); James J. McNally, Souderton, PA (US)

(73) Assignee: Janssen Pharmaceutica N.V., Beerse (BE)

( * ) Notice: Subject to any disclaimer, the term of this patent is extended or adjusted under 35 U.S.C. 154(b) by 0 days.

(21) Appl. No.: 11/326,084

(22) Filed: Jan. 5, 2006

(65) Prior Publication Data

US 2006/0148823 A1 Jul. 6, 2006

Related U.S. Application Data

(60) Provisional application No. 60/641,699, filed on Jan. 6, 2005.

(51) Int. Cl.
*A61K 31/535* (2006.01)
*A61K 31/54* (2006.01)
*C07D 265/38* (2006.01)
*C07D 417/00* (2006.01)

(52) U.S. Cl. .................. 514/229.8; 544/102; 544/42; 514/225.5

(58) Field of Classification Search .......... 514/252.04, 514/225.2; 544/42, 102
See application file for complete search history.

(56) References Cited

U.S. PATENT DOCUMENTS

| | | | |
|---|---|---|---|
| 2,368,006 A | 1/1945 | Cusic | |
| 2,784,185 A * | 3/1957 | Schuler | 544/42 |
| 2,901,478 A * | 8/1959 | Schuler | 544/42 |
| 3,179,665 A | 4/1965 | Schmutz | |
| 3,305,547 A * | 2/1967 | Bickelhaupt et al. | 544/46 |
| 3,470,188 A | 9/1969 | Kaiser et al. | |
| 3,557,287 A | 1/1971 | Berde et al. | |
| 3,931,232 A | 1/1976 | Bender et al. | |
| 3,987,042 A | 10/1976 | Gueremy et al. | |
| 4,086,350 A | 4/1978 | Zirkle | |
| 4,275,209 A | 6/1981 | Lassen et al. | |
| 4,356,184 A | 10/1982 | Deason et al. | |
| 4,666,907 A * | 5/1987 | Fortin et al. | 514/226.2 |
| 4,777,177 A | 10/1988 | Traber et al. | |
| 5,502,049 A * | 3/1996 | Garret et al. | 514/224.8 |
| 6,004,983 A * | 12/1999 | Andersen et al. | 514/325 |
| 6,114,354 A | 9/2000 | Andersen et al. | |
| 6,153,626 A | 11/2000 | Pelcman et al. | |
| 7,060,711 B2 | 6/2006 | Lubbert et al. | |
| 2003/0018447 A1 | 1/2003 | Florschuetz | |
| 2003/0166672 A1 | 9/2003 | Lubbert et al. | |
| 2005/0009860 A1 | 1/2005 | Carson et al. | |
| 2006/0030585 A1 | 2/2006 | Dax et al. | |
| 2006/0135522 A1 | 6/2006 | Carson et al. | |
| 2006/0135524 A1 | 6/2006 | Carson et al. | |
| 2006/0135763 A1 | 6/2006 | Coats et al. | |
| 2006/0148823 A1 | 7/2006 | Coats et al. | |
| 2006/0287297 A1 | 12/2006 | DeCorte et al. | |

FOREIGN PATENT DOCUMENTS

| | | |
|---|---|---|
| DE | 2009555 | 2/1970 |
| EP | 0005607 | 11/1979 |
| EP | 1049676 A | 11/2000 |
| EP | 1306376 A1 | 5/2003 |
| EP | 1321169 A1 | 6/2003 |
| FR | 2290202 A1 | 6/1976 |
| GB | 1128734 | 10/1968 |
| WO | WO 98/28275 A1 | 7/1998 |
| WO | WO 9900376 A1 | 1/1999 |
| WO | WO 0146191 A1 | 6/2001 |
| WO | WO 0166543 A2 | 9/2001 |
| WO | WO 0172303 A1 | 10/2001 |
| WO | WO 02/36573 A2 | 5/2002 |
| WO | WO 02/48122 A2 | 6/2002 |
| WO | WO 03035646 A2 | 5/2003 |
| WO | WO 04026030 A2 | 4/2004 |
| WO | WO 04035540 A1 | 4/2004 |
| WO | WO 04092165 A1 | 10/2004 |
| WO | WO 05003131 A1 | 1/2005 |

OTHER PUBLICATIONS

Dorwald F. A. Side Reactions in Organic Synthesis, 2005, Wiley: VCH, Weinheim p. IX of Prefac & Chapter 8, pp. 279-308.*
Commercial 2-Bromo-Phenols from Sigma-Aldrich.*
Commercial 4-piperidinones.*
Frontier Scientific (Logan, UT) Commercial Boronic Acids.*
Hutchins, R.O. et. al. J. Orig. Chem. 1977, 42, 82-91.*
Quock et al., "The d-Opioid Receptor: Molecular Pharmacology, Signal Transduction, and the Determination of Drug Efficacy" Pharmacological Reviews 1999, 51(3), 503-532.*
Mark Connor and Macdonald J Christie "Opioid Receptor Signaling Mechanisms" Clinical and Experimental Pharmacology and Physiology 1999 26, 493-499.*
Terry Kenakin and Ongun Onaran "The ligand paradox between affinity and efficacy: can you be there and not make a difference?" TRENDS in Pharmacological Sciences 2002, 23, 275-280.*
Nieschulz, Otto: Hoffmann, Irmgard; Popendiker, Kurt "Pharmacological studies on 10-(I-methyl-3-piperidyl)-2 methoxyphenothiazine and related compounds" Arzneimittel-Forschung 1960, 10, 156-65.*
Thomas, J.B. et al '(±)-4-[(N-Allyl-CIS-3-Methyl-4-Piperidinyl)Phenylamino]-N,N-Diethylbenzamide Displays Selective binding for the Delta Opioid Receptor' Bioorganic & Medicinal Chemistry Letters. vol. 9, No. 20 (1999) pp. 3053-3056.

(Continued)

*Primary Examiner*—Rita Desai
*Assistant Examiner*—David K O'Dell

(57) ABSTRACT

The invention is directed to delta opioid receptor modulators. More specifically, the invention relates to tricyclic δ-opioid modulators. Pharmaceutical and veterinary compositions and methods of treating mild to severe pain and various diseases using compounds of the invention are also described.

6 Claims, No Drawings

OTHER PUBLICATIONS

Thomas, J.B. et al 'Factors Influencing Agonist Potency and Selectivity for the Opioid δ Receptor are Revealed in Structure-Activity Relationship Studies of the 4-[(N-Substituted-4-piperidinyl)arylamino]-N,N-diethylbenzamides' J. Med. Chem. vol. 44, No. 6 (2001) pp. 972-987.

PCT International Search Report dated Jun. 22, 2006 for PCT Application No. PCT/US2006/000491 dated Jan. 5, 2006 which relates to U.S. Appl. No. 11/326,084 and a Written Opinion dated Jun. 22, 2006.

Kaiser, C. et al., "Analogs of Phenothiazines. 5. Synthesis and Neuropharmacological Activity of Some Piperidylidene Derivatives of Thioxanthenes, Xanthenes, Dibenzoxepins, and Acridans", *J. Med. Chem.*, 1974, pp. 57-62, vol. 17, No. 1.

Wentland, M. et al., "8-Aminocyclazocine Analogues: Synthesis and Structure-Activity relationships", *Bioorganic & Med. Chem. Lett.*, 2000, pp. 183-187, vol. 10, No. 2.

Wentland, M. et al., "Selective Protection and Functionalization of Morphine: Synthesis and Opioid Receptor Binding Properties of 3-Amino-3-desoxymorphine Derivatives", *J. Med. Chem.* 2000, pp. 3558-3565, vol. 43, No. 19.

Wentland, M. et al., "3-Carboxamide Analogues of Morphine and Naltrexone: Synthesis and Opioid Receptor Binding Properties", *Bioorganic & Med. Chem. Lett.*, 2001, pp. 1717-1721, vol. 11.

Wentland, M. et al., "8-Carboxamidocyclazocine Analogues: Redefining the Structure-Activity Relationships of 2,6-Methano-3-benzazocines", *Bioorganic & Med. Chem. Lett.*, 2001, pp. 623-626, vol. 11.

Bidlack, J.M., "8-Carboxamidocyclazocine: A Long-Acting, Novel Benzomorphan", *J. Pharm. & Exp. Ther.* 2002, pp. 374-380, vol. 302, No. 1.

Wentland, M. et al., "Synthesis and Opioid Receptor Binding Affinities of 8-Amino-2,6-methano-3-benzazocines", *J. Med. Chem.* 2003, pp. 838-849, vol. 46.

Wentland, M. et al., "Redefining the Structure—Activity Relationships of 2,6-Methano-3-benzazocines. Part 2:8-Formamidocylclazocine Analogues". *Bioorganic & Med. Chem. Lett.* 2003, pp. 1911-1914, vol. 13.

Wentland, M. et al., "Thioformamido and Thiocarboxamido Derivatives of Cyclazocine: Syntheses and Opioid Receptor Bnding Properties", *Abstract of Paper*, 226th ACS Natl. Mtg., N.Y. 2003.

Zhang, A. et. al., "10-Ketomorphinan and 3-Substituted-3-desoxymorphinan Analogues as Mixed κ and μ Opioid Ligands: Synthesis and Biological Evaluation of Their Binding Affinity at Opioid Receptors", *J. Med. Chem.*, 2004, pp. 165-174, vol. 47, No. 1.

Wentland, M. et al., "Redefining the structure-activity relationships of 2,6-methano-3-benzazocines. Part 3: 8-Thiocarboxamido and 8-thioformamido derivatives of cyclazocine", *Bioorganic & Med. Chem. Lett.*, 2005. pp. 2547-2551, vol. 15.

Wentland, M. et al., "Synthesis and opioid receptor binding properties of a highly potent 4-hydroxy analogue of naltrexone", *Bioorganic & Med. Chem. Lett.*, 2005, pp. 2107-2110.

Sun, X., et al. "Synthesis and Opioid Receptor Binding Properties of Conformation-Rigidified Analogues of 8-Carboxamidocyclazocine and 8-Formamidocyclazocine", *Abstract of Papers*, 229th ACS Natl. Mtg., N.Y. 2005.

VanAlstine, M. A., "Synthesis and evaluation of novel N-substituted derivatives of 8-carboxamidocyclazocine", Abstract of papers 231st ACS National Meeting, Atlanta, GA, 2006, MEDI-009.

Gilbert, P.E. et al.: "The Effects of Morphine- and Nalophine-Like Drugs in the Nondependent, Morphine-Dependent and Cyclazocine-dependent Chronic Spinal Dog1"; The J. of Pharm. And Exp. Thera. (1976) 198(1): 66-82.

Gross, R.A. et al: "dynorphin A and cAMP-dependent protein kinase independently regulate calcium currents"; Proc. Natl. Acad. Sci. (1990) 87: 7025-7029.

Gould, P.L.: "Salt selection for basic drugs"; Intl. J. of Pharm. (1986) 33: 201-217.

Hancock, B.C. et al.: "Characteristics and Significance of the Amorphous State in Pharmaceutical Systems"; J. of Pharm. Sciences, (Jan. 1997) 86(1): 1-12.

Kaiser, C. et al.: "Analogs of Phenothiazines. 5. Synthesis and Neuropharmacological Activity of Some Piperidylidene Derivatives of Thioxanthenes, Xanthenes, Dibenzoxepins, and Acridans"; J of Med. Chem. (1974) 17(1): 57-62.

Lord, John A.H. et al.: "Endogenous opioid peptides: multiple agonists and receptors"; Nature (1977) 267: 495-499.

Mansour, A. et al.: "Anatomy of CNS opiid receptors"; Trends In Neuroscience (1988) 11(7): 308-314.

Pert, C.B. et al.: "Opiate Receptor: Demonstration in Nervous Tissue"; Science (1973) 179: 1011-1014.

Sharma, S.K. et al.: "Dual regulation of adenylate cyclase accounts for narcotic dependence and tolerance"; Proc. Natl. Acad. Sci. (1975) 72(8): 3092-3096.

Still, W. Clark et al.: "Rapid Chromatographic Technique for Preparative Separations with Moderate Resolution"; J. Org. Chem. (1978) 43(14): 2923-2925.

Truce, W.E. et al.: "The Smiles an Related Rearrangements of Aromatic Systems"; Organic Reactions (1970) 18:99-215.

Wollemann, M.: "Recent Developments in the Research of Opioid Receptor Subtype Molecular Characterization"; J. of Neurochemistry (1990): 1095-1101.

Ananthan, S.: The AAPS Journal 2006, 8(1): E118-E125. (First cited by Examiner in application No. 11/424,311.)

Berge, S.M. et al.: Pharmaceutical Salts; J. of Pharmaceutical Sciences (1977) 66(1): 1-19.

Biemans, H.A.M. et al.: Hexapyrrolylbenzene and Octapyrrolyinaphthalene; J. Org. Chem. (1996) 61:9012-9015. (First cited byy Examiner in U.S. Appl. No. 11/195,231).

Boyd, R.E. et al.: Synthesis and Binding Affinities of 4-Diarylaminotropanes, a New Class of Delta Opioid Agonist; Bioorg. & Med. Chem. Letters (2000) 10: 1109-1111.

Calo, G. et al.: [Nphe$^1$,Arg$^{14}$,Lys$^{15}$]Nociceptin-NH$_2$, a novel potent and selective antagonist of the nociceptin/orphanin FQ receptor; British J. of Pharmacology (2002) 136:303-311. (First cited by Examiner in U.S. Appl. No. 11/195,231.).

Chang, K.J. et al.: Benzomorphan Sites Are Ligand Recognition Sites of Putative ε-receptors; Molecular Pharmacology (1984) 26: 484-488. (First cited by Examiner in U.S. Appl. No 11/195,231).

Dorwald, F.Z.: Side Reactions in Organic Synthesis (2005) Wiley: VCH, Weinheim, p. 1X of Preface. (First cited by Examiner in U.S. Appl. No. 11/314,300).

Dorwald, F.Z.: Side Reactions in Organic Synthesis (2005) Wiley: VCH, Weinheim p. 1X of Preface: 1-15. (Examiner citation in U.S. Appl. No. 11/313,704).

Erchegyi, J. et al.: Novel sst$_4$-Selective Somatostatin (SRIF) Agonists. 2. Analogues with β-Methyl-3-(2-naphthyl)alanine Substitutions at Position 8; J. Med. Chem. (2003) 46: 5587-5596. (First cited Examiner in U.S. Appl. No. 11/195,231).

Frontier Scientific Catalog (Logan, UT) Adavanced Discovery Chemicals Pure (and not so) Simple 2006; Discover Chemicals A-F, H-I, M-N, P-Q and T. Examiner citation in U.S. Appl. No. 11/314,300).

Gribble, G.W. et al.: Sodium Triacetoxyborohydride$^1$; Encyclopedia of Regents for Organic Synthesis online @ http://www.mrw.interscience.wiley.com/eros/articles/rs112/sec0.html Apr. 24, 2007. (Examiner citation in U.S. Appl. No. 11/424,311).

Kruszynski, R. et al.: Novel endomorphin-2 analogs with μ-opioid receptor antagonist activity; J. of Peptide Research (2005) 66: 125-131. (first cited by Examiner in U.S. Appl. No. 11/195,231.)

Le Bars, D. et al.: Animal Models of Nociception; Pharmacologocal Reviews (2001) 53(4): 597-652. (Examinier citation in U.S. Appl. No. 10/873,527.).

Loughhead, D.G.: Unusual Reductions Induced by Formic Acid; Tetrahedron Letters (1988) 29(45): 5701-5702. (First cited by Examiner in U.S. Appl. No. 11/314,300.).

Pozharskii, A.F. et al.: Molecular Rings Studded With Jewels; Heterocycles in Life and Society, Wiley (1997): 1-6. (First cited by Examiner in U.S. Appl. No. 11/195.231.).

Structures in copending U.S. Appl. No. 11-195,231. (Created by Examiner in U.S. Appl. No. 11/424,231.).

Tao, M. et al.: Synthesis and structure-activity relationships of novel poly (ADP-ribose) polymerase-1 inhibitors; Bioorg. & Med. Chem. Letters (2006) 16: 938-942. (First cited ny Examiner in U.S. Appl. No. 11-195,231.).

Thomas, J.B. et al.: 4-[8-Alkyl-8-azabicyclo[3.2.1.]octyl-3-yl)-3-arylanilino]-N,N-diethylbenzamides: High Affinity, Selective Ligands for the Delta Opioid Receptor Illustrate Factors Important to Antagonist Activity; Bioorg. & Med. Chem. Letters (2000) 10(11): 1281-1284.

Walpole, C.S.J. et al.: The Discovery of Capsazepine, the First Competitive Antagonist of the Sensory Neuron Excitants Capsaicin and Resiniferatoxin; J. Med. Chem. (1994) 37: 1942-1954. (Examiner citation in U.S. Appl. No. 11/314,300.).

West, A.R.: Solid State Chemistry and its Applications, Wiley, New York, 1988: 358 & 365. (First cited by Examiner in U.S. Appl. No. 11/195,231.).

Zhang, X. et al.: Probes for Narcotic Receptor Mediated Phenomena. 26.[1-3] Synthesis and Biological Evaluation of Diarylmethylpiperazines and Diarymethylpiperidines as Novel, Nonpeptidic δ Opioid Receptor Ligands; J. Med. Chem. (1999) 42: 5455-5463. (First cited by Examiner in U.S. Appl. No. 11/314,300.).

Calderon, S.N. et al.: SNC 80 and Related δ Opioid Agonist; Current Pharmaceutical Design (2004) 10: 733-742. (Cited by Examiner in U.S. Appl. No. 11/195,231).

Carson, J.R. et al.: N-Alkyl-4[(8-azabicyclo[3.2.1]-oct-3-ylident)phenylmethyl]-benzamides, μ address; Bioorganic & Med. Chem. Letters (2004) 14: 2113-2116. (Cited by Examiner in U.S. Appl. No. 10/873,527).

Furness, M. S. et al.: Probes for Narcotic Receptor-Mediated Phenomena. 27.[1] Synthesis and Pharmacological Evaluation of Selective δ-Opioid Receptor Agonists from 4-[(αR)-α-(2S,5R)-4-Substituted-2,5-dimethyl-1-piperazinyl-3-methoxybenzyl]- N,N-diethylbenzamides and Their Enantiomers; J. Med. Chem. (2000) 43: 3193-3196. (Cited by Examiner in U.S. Appl. No. 10/873,527).

Jones, M. JR.: Organic Chemistry Norton, New York (1997): 578-591. (Cited by Examiner in U.S. Appl. No. 11/424,311.).

* cited by examiner

PIPERDINYL-PHENOXAZINE AND PHENOTHIAZINE DERIVATIVES AS δ-OPIOID MODULATORS

CROSS-REFERENCE TO RELATED APPLICATIONS

This application claims the benefit of U.S. application Ser. No. 60/641,699, filed Jan. 6, 2005, which is incorporated herein in its entirety.

STATEMENT REGARDING FEDERALLY SPONSORED RESEARCH OR DEVELOPMENT

The research and development of the invention described below was not federally sponsored.

BACKGROUND OF THE INVENTION

The term "opiate" has been used to designate pharmacologically active alkaloids derived from opium, e.g., morphine, codeine, and many semi-synthetic congeners of morphine. After the isolation of peptide compounds with morphine-like actions, the term opioid was introduced to refer generically to all drugs with morphine-like actions. Included among opioids are various peptides that exhibit morphine-like activity, such as endorphins, enkephalins and dynorphins. However, some sources use the term "opiate" in a generic sense, and in such contexts, opiate and opioid are interchangeable. Additionally, the term opioid has been used to refer to antagonists of morphine-like drugs as well as to characterize receptors or binding sites that combine with such agents.

Opioids are generally employed as analgesics, but they may have many other pharmacological effects as well. Morphine and related opioids produce certain of their major effects on the central nervous and digestive systems. The effects are diverse, including analgesia, drowsiness, mood changes, respiratory depression, dizziness, mental clouding, dysphoria, pruritus, increased pressure in the biliary tract, decreased gastrointestinal motility, nausea, vomiting, and alterations of the endocrine and autonomic nervous systems.

When therapeutic doses of morphine are given to patients with pain, they report that the pain is less intense, less discomforting, or entirely gone. In addition to experiencing relief of distress, some patients experience euphoria. However, when morphine in a selected pain-relieving dose is given to a pain-free individual, the experience is not always pleasant; nausea is common, and vomiting may also occur. Drowsiness, inability to concentrate, difficulty in mentation, apathy, lessened physical activity, reduced visual acuity, and lethargy may ensue.

Two distinct classes of opioid molecules can bind opioid receptors: the opioid peptides (e.g., the enkephalins, dynorphins, and endorphins) and the alkaloid opiates (e.g., morphine, etorphine, diprenorphine and naloxone). Subsequent to the initial demonstration of opiate binding sites (Pert, C. B. and Snyder, S. H., Science (1973) 179:1011-1014), the differential pharmacological and physiological effects of both opioid peptide analogues and alkaloid opiates served to delineate multiple opioid receptors. Accordingly, three molecularly and pharmacologically distinct opioid receptor types have been described: delta, kappa and mu. Furthermore, each type is believed to have sub-types (Wollemann, M., J Neurochem (1990) 54:1095-1101; Lord, J. A., et al., Nature (1977) 267:495-499).

All three of these opioid receptor types appear to share the same functional mechanisms at a cellular level. For example, the opioid receptors cause inhibition of adenylate cyclase, and inhibition of neurotransmitter release via both potassium channel activation and inhibition of $Ca^{2+}$ channels (Evans, C. J., In: Biological Basis of Substance Abuse, S. G. Korenman & J. D. Barchas, eds., Oxford University Press (in press); North, A. R., et al., Proc Natl Acad Sci USA (1990) 87:7025-29; Gross, R. A., et al., Proc Natl Acad Sci USA (1990) 87:7025-29; Sharma, S. K., et al., Proc Natl Acad Sci USA (1975) 72:3092-96). Although the functional mechanisms are the same, the behavioral manifestations of receptor-selective drugs differ greatly (Gilbert, P. E. & Martin, W. R., J Pharmacol Exp Ther (1976) 198:66-82). Such differences may be attributable in part to the anatomical location of the different receptors.

Delta receptors have a more discrete distribution within the mammalian CNS than either mu or kappa receptors, with high concentrations in the amygdaloid complex, striatum, substantia nigra, olfactory bulb, olfactory tubercles, hippocampal formation, and the cerebral cortex (Mansour, A., et al., Trends in Neurosci (1988) 11:308-14). The rat cerebellum is remarkably devoid of opioid receptors including delta opioid receptors.

D. Delorme, E. Roberts and Z. Wei, World Patent WO/28275 (1998) discloses diaryl methylidenylpiperidines that are opioid analgesics, but does not disclose or suggest the compounds of the present invention.

C. Kaiser, and others (J. Med. Chem. 1974, Volume 17, pages 57-61) disclose some piperidylidene derivatives of thioxanthenes, xanthenes, dibenoxepins and acridans that are neuroleptic agents. These authors, however, do not disclose or suggest either the structure or the activity of the compounds of the present invention.

British Patent GB 1128734 (1966) discloses derivatives of 6,11-dihydrodibenzo[b,e]oxepine that are anticholinergic, anti-convulsive, muscle-relaxing, sedating, diuretic, and/or vasoactive agents. These, agents, however, differ significantly from the compounds of the present invention both structurally and pharmacologically.

There is a continuing need for new delta opioid receptor modulators as analgesics. There is a further need for delta opioid receptor selective agonists as analgesics having reduced side effects. There is also a need for delta opioid receptor antagonists as immunosuppressants, antiinflammatory agents, agents for the treatment of neurological and psychiatric conditions, agents for the treatment of urological and reproductive conditions, medicaments for drug and alcohol abuse, agents for treating gastritis and diarrhea, cardiovascular agents and agents for the treatment of respiratory diseases, having reduced side effects.

SUMMARY OF THE INVENTION

The present invention is directed to compounds of Formula (I) and to compositions comprising one or more compounds of Formula (I):

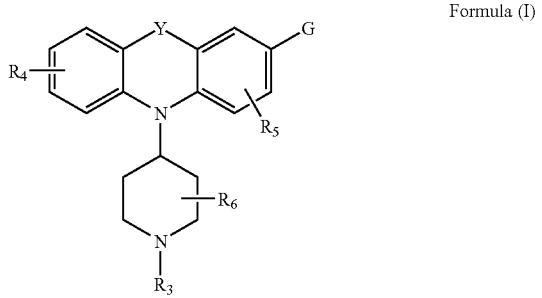

Formula (I)

wherein:
- G is —C(Z)N($R_1$)$R_2$, $C_{6-10}$aryl, or a heterocycle selected from the group consisting of imidazolyl, triazolyl, tetrazolyl, oxadiazolyl, thiadiazolyl, oxathiadiazolyl, imidazolinyl, tetrahydropyrimidinyl, thienyl, pyrazolyl, pyrimidinyl, triazinyl, furyl, indazolyl, indolyl, indolinyl, isothiazolyl, isoxazolyl, oxazolyl, isoxadiazolyl, benzoxazolyl, quinolinyl, isoquinolinyl, and pyridinyl; wherein the $C_{6-10}$aryl and the heterocycles of G are optionally substituted with one to three substituents independently selected from the group consisting of $C_{1-8}$alkanyl, $C_{2-8}$alkenyl, $C_{2-8}$alkynyl, $C_{1-8}$alkanyloxy, hydroxy($C_{1-8}$)alkanyl, carboxy($C_{1-8}$)alkanyl, $C_{1-8}$alkanylcarbonylamino, halogen, hydroxy, cyano, nitro, oxo, thioxo, amino, $C_{1-6}$alkanylamino, di($C_{1-6}$alkanyl)amino, $C_{1-8}$alkanylthio, $C_{1-8}$alkanylsulfonyl, $C_{1-8}$alkanylsulfonylamino, aminocarbonyl, aminothiocarbonyl, aminocarbonylamino, aminothiocarbonylamino, $C_{1-8}$alkanylaminocarbonyl, di($C_{1-8}$alkanyl)aminocarbonyl, and $C_{1-6}$alkanyloxycarbonylamino;
- $R_1$ is a substituent selected from the group consisting of hydrogen, $C_{1-8}$alkanyl, $C_{2-8}$alkenyl, and $C_{2-8}$alkynyl;
- $R_2$ is a substituent selected from the group consisting of hydrogen; $C_{1-8}$alkanyl; $C_{2-8}$alkenyl; $C_{2-8}$alkynyl; $C_{6-10}$aryl; and $C_{1-8}$cycloalkanyl; wherein $C_{1-8}$alkanyl is optionally substituted with one to three substituents independently selected from the group consisting of phenyl, amino, $C_{1-6}$alkanylamino, di($C_{1-6}$alkanyl)amino, $C_{1-6}$alkanyloxy, thio$C_{1-6}$alkanyloxy, hydroxy, fluoro, chloro, cyano, aminocarbonyl, $C_{1-8}$alkanylaminocarbonyl, di($C_{1-8}$alkanyl)aminocarbonyl, $C_{1-6}$alkanyloxycarbonyl, and aryloxy; and wherein any aryl-containing substituents and $C_{1-8}$cycloalkanyl substituents of $R_2$ are optionally substituted with one to three substituents independently selected from the group consisting of $C_{1-8}$alkanyl, $C_{2-8}$alkenyl, $C_{2-8}$alkynyl, $C_{1-8}$alkanyloxy, trifluoromethyl, trifluoromethoxy, phenyl, halogen, cyano, hydroxy, $C_{1-8}$alkanylthio, $C_{1-8}$alkanylsulfonyl, and $C_{1-8}$alkanylsulfonylamino;
- or $R_1$ and $R_2$ taken together with the nitrogen to which they are attached form a 5-7 membered cycloheteroalkyl optionally substituted with one to three substituents independently selected from the group consisting of $C_{1-8}$alkanyl, hydroxy($C_{1-8}$)alkanyl, hydroxy, amino, $C_{1-6}$alkanylamino, di($C_{1-6}$alkanyl)amino, and halogen;
- $R_3$ is a substituent selected from the group consisting of hydrogen, $C_{1-8}$alkanyl, halo$_{1-3}$($C_{1-8}$)alkanyl, $C_{2-8}$alkenyl, $C_{2-8}$alkynyl, $C_{3-8}$cycloalkanyl, cycloalkanyl($C_{1-8}$)alkanyl, $C_{1-8}$alkanyloxy($C_{1-8}$)alkanyl, $C_{1-8}$alkanylthio($C_{1-8}$)alkanyl, hydroxy$C_{1-8}$alkanyl, $C_{1-8}$alkanyloxycarbonyl, halo$_{1-3}$($C_{1-8}$)alkanylcarbonyl, formyl, thioformyl, carbamimidoyl, phenylimino($C_{1-8}$)alkanyl, phenyl($C_{1-8}$)alkanyl, phenyl($C_{1-8}$)alkenyl, phenyl($C_{1-8}$)alkynyl, naphthyl($C_{1-8}$)alkanyl and heteroaryl($C_{1-8}$)alkanyl wherein the heteroaryl is selected from the group consisting of benzo[1,3]dioxolyl, imidazolyl, furanyl, pyridinyl, thienyl, indazolyl, indolyl, indolinyl, isoindolinyl, isoquinolinyl, isothiazolyl, isoxazolyl, oxazolyl, pyrazinyl, pyrazolyl, pyridazinyl, pyrimidinyl, pyrrolyl, quinolinyl, isoquinolinyl, tetrazolyl, thiazolyl; wherein phenyl, naphthyl and heteroaryl are optionally substituted with one to three substituents independently selected from the group consisting of $C_{1-6}$alkanyl, $C_{2-6}$alkenyl, $C_{1-6}$alkanyloxy, amino, $C_{1-6}$alkanylamino, di($C_{1-6}$alkanyl)amino, $C_{1-6}$alkanylcarbonyl, $C_{1-6}$alkanylcarbonyloxy, $C_{1-6}$alkanylcarbonylamino, $C_{1-6}$alkanylthio, $C_{1-6}$alkanylsulfonyl, halogen, hydroxy, cyano, fluoro($C_{1-6}$)alkanyl, thioureido, and fluoro($C_{1-6}$)alkanyloxy; alternatively, when phenyl and heteroaryl are optionally substituted with alkanyl or alkanyloxy substituents attached to adjacent carbon atoms, the two substituents can together form a fused cyclic alkanyl or cycloheteroalkanyl selected from the group consisting of —(CH$_2$)$_{3-5}$—, —O(CH$_2$)$_{2-4}$—, —(CH$_2$)$_{2-4}$O—, and —O(CH$_2$)$_{1-3}$O—;
- $R_4$ is one to three substituents independently selected from the group consisting of hydrogen; $C_{1-6}$alkanyl; $C_{2-6}$alkenyl; $C_{2-6}$alkynyl; aryl($C_{2-6}$)alkynyl; $C_{1-6}$alkanyloxy; amino; $C_{1-6}$alkanylamino; di($C_{1-6}$alkanyl)amino; $C_{6-10}$arylamino wherein $C_{6-10}$aryl is optionally substituted with one to three substitutents independently selected from the group consisting of $C_{1-6}$alkanyl, $C_{1-6}$alkoxy, halogen, and hydroxyl; formylamino; pyridinylamino; $C_{1-6}$alkanylcarbonyl; $C_{1-6}$alkanylcarbonyloxy; $C_{1-6}$alkanyloxycarbonyl; aminocarbonyl; $C_{1-6}$alkanylaminocarbonyl; di($C_{1-6}$alkanyl)aminocarbonyl; $C_{1-6}$alkanylcarbonylamino; $C_{1-6}$alkanylthio; $C_{1-6}$alkanylsulfonyl; halogen; hydroxy; cyano; hydroxycarbonyl; $C_{6-10}$aryl; chromanyl; chromenyl; furanyl; imidazolyl; indazolyl; indolyl; indolinyl; isoindolinyl; isoquinolinyl; isothiazolyl; isoxazolyl; naphthyridinyl; oxazolyl; pyrazinyl; pyrazolyl; pyridazinyl; pyridinyl; pyrimidinyl; pyrrolyl; quinazolinyl; quinolinyl; quinolizinyl; quinoxalinyl; tetrazolyl; thiazolyl; thienyl; fluoroalkanyl and fluoroalkanyloxy; or optionally; when $R_4$ is two substituents attached to adjacent carbon atoms, the two substituents together form a single fused moiety, wherein the fused moiety is —(CH$_2$)$_{3-5}$—, —O(CH$_2$)$_{2-4}$—, —(CH$_2$)$_{2-4}$O—, —O(CH$_2$)$_{1-3}$O—, or —S—C(NH$_2$)=N—;
- $R_5$ is one to two substituents independently selected from the group consisting of hydrogen, $C_{1-6}$alkanyl, $C_{2-6}$alkenyl, $C_{1-6}$alkanyloxy, amino, $C_{1-6}$alkanylamino, di($C_{1-6}$alkanyl)amino, $C_{1-6}$alkanylcarbonyl, $C_{1-6}$alkanylcarbonyloxy, $C_{1-6}$alkanyloxycarbonyl, $C_{1-6}$alkanylaminocarbonyl, $C_{1-6}$alkanylcarbonylamino, $C_{1-6}$alkanylthio, $C_{1-6}$alkanylsulfonyl, halogen, hydroxy, cyano, fluoro($C_{1-6}$)alkanyl and fluoro($C_{1-6}$)alkanyloxy;
- $R_6$ is one to four substituents independently selected from the group consisting of hydrogen, $C_{1-6}$alkanyl, $C_{2-6}$alkenyl, $C_{1-6}$alkanyloxy, amino, $C_{1-6}$alkanylamino, di($C_{1-6}$alkanyl)amino, $C_{1-6}$alkanylcarbonyl, $C_{1-6}$alkanylcarbonyloxy, $C_{1-6}$alkanyloxycarbonyl, $C_{1-6}$alkanylaminocarbonyl, $C_{1-6}$alkanylcarbonylamino, $C_{1-6}$alkanylthio, $C_{1-6}$alkanylsulfonyl, halogen, hydroxy, cyano, fluoro($C_{1-6}$)alkanyl and fluoro($C_{1-6}$)alkanyloxy;

Y is O or S;

Z is O, S, NH, N($C_{1-6}$alkanyl), N(OH), N(O$C_{1-6}$alkanyl), or N(phenyl);

and enantiomers, diastereomers, tautomers, solvates, or pharmaceutically acceptable salts thereof.

Finally, the present invention is directed to veterinary and pharmaceutical compositions containing compounds of Formula (I) wherein the compositions are used to treat mild to severe pain in warm-blooded animals.

DETAILED DESCRIPTION OF THE INVENTION

As used herein, the following underlined terms are intended to have the following meanings:

"$C_{a-b}$" (where a and b are integers) refers to a radical containing from a to b carbon atoms inclusive. For example, $C_{1-3}$ denotes a radical containing 1, 2 or 3 carbon atoms "Alkyl:" refers to a saturated or unsaturated, branched, straight-chain or cyclic monovalent hydrocarbon radical derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl, cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like. Where specific levels of saturation are intended, the nomenclature "alkanyl", "alkenyl" and/or "alkynyl" is used, as defined below. In preferred embodiments, the alkyl groups are ($C_1$-$C_6$) alkyl, with ($C_1$-$C_3$) being particularly preferred.

"Alkanyl:" refers to a saturated branched, straight-chain or cyclic monovalent hydrocarbon radical derived by the removal of one hydrogen atom from a single carbon atom of a parent alkane. Typical alkanyl groups include, but are not limited to, methanyl; ethanyl; propanyls such as propan-1-yl, propan-2-yl, cyclopropan-1-yl, etc.; butyanyls such as butan-1-yl, butan-2-yl, 2-methyl-propan-1-yl, 2-methyl-propan-2-yl, cyclobutan-1-yl, etc.; and the like. In preferred embodiments, the alkanyl groups are ($C_{1-8}$) alkanyl, with ($C_{1-3}$) being particularly preferred.

"Alkenyl" refers to an unsaturated branched, straight-chain or cyclic monovalent hydrocarbon radical having at least one carbon-carbon double bond derived by the removal of one hydrogen atom from a single carbon atom of a parent alkene. The radical may be in either the cis or trans conformation about the double bond(s). Typical alkenyl groups include, but are not limited to, ethenyl; propenyls such as prop-1-en-1-yl, prop-1-en-2-yl, prop-2-en-1-yl, prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like.

"Alkynyl" refers to an unsaturated branched, straight-chain or cyclic monovalent hydrocarbon radical having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like.

"Heteroalkyl" and Heteroalkanyl" refer to alkyl or alkanyl radicals, respectively, in which one or more carbon atoms (and any necessary associated hydrogen atoms) are independently replaced with the same or different heteroatoms (including any necessary hydrogen or other atoms). Typical heteroatoms to replace the carbon atom(s) include, but are not limited to, N, P, O, S, Si, etc. Preferred heteroatoms are O, N and S. Thus, heteroalkanyl radicals can contain one or more of the same or different heteroatomic groups, including, by way of example and not limitation, epoxy (—O—), epidioxy (—O—O—), thioether (—S—), epidithio (—SS—), epoxythio (—O—S—), epoxyimino (—O—NR'—), imino (—NR'—), biimino (—NR'—NR'—), azino (=N—N=), azo (—N=N—), azoxy (—N—O—N—), azimino (—NR'—N=N—), phosphano (—PH—), $\lambda^4$-sulfano (—SH$_2$—), sulfonyl (—S(O)$_2$—), and the like, where each R' is independently hydrogen or ($C_1$-$C_6$) alkyl.

"Parent Aromatic Ring System:" refers to an unsaturated cyclic or polycyclic ring system having a conjugated π electron system. Specifically included within the definition of "parent aromatic ring system" are fused ring systems in which one or more rings are aromatic and one or more rings are saturated or unsaturated, such as, for example, indane, indene, phenalene, etc. Typical parent aromatic ring systems include, but are not limited to, aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like "Aryl:" refers to a monovalent aromatic hydrocarbon radical derived by the removal of one hydrogen atom from a single carbon atom of a parent aromatic ring system. Typical aryl groups include, but are not limited to, radicals derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like. In preferred embodiments, the aryl group is ($C_{5-20}$) aryl, with ($C_{5-10}$) being particularly preferred. Particularly preferred aryl groups are phenyl and naphthyl groups.

"Arylalkyl:" refers to an acyclic alkyl group in which one of the hydrogen atoms bonded to a carbon atom, typically a terminal carbon atom, is replaced with an aryl radical. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylalkenyl and/or arylalkynyl is used. [In preferred embodiments, the arylalkyl group is ($C_{6-26}$) arylalkyl, e.g., the alkanyl, alkenyl or alkynyl moiety of the arylalkyl group is ($C_{1-6}$) and the aryl moiety is ($C_{5-20}$). In particularly preferred embodiments the arylalkyl group is ($C_{6-13}$), e.g., the alkanyl, alkenyl or alkynyl moiety of the arylalkyl group is ($C_{1-3}$) and the aryl moiety is ($C_{5-10}$). Even more preferred arylalkyl groups are phenylalkanyls.

"Alkanyloxy:" refers to a saturated branched, straight-chain or cyclic monovalent hydrocarbon alcohol radical derived by the removal of the hydrogen atom from the hydroxide oxygen of the alcohol. Typical alkanyloxy groups include, but are not limited to, methanyloxy; ethanyloxy; propanyloxy groups such as propan-1-yloxy ($CH_3CH_2CH_2O$—), propan-2-yloxy (($CH_3)_2CHO$—), cyclopropan-1-yloxy, etc.; butanyloxy groups such as butan-1-yloxy, butan-2-yloxy, 2-methyl-propan-1-yloxy, 2-methyl-propan-2-yloxy, cyclobutan-1-yloxy, etc.; and the like. In preferred embodiments, the alkanyloxy groups are ($C_{1-8}$) alkanyloxy groups, with ($C_{1-3}$) being particularly preferred.

"Parent Heteroaromatic Ring System:" refers to a parent aromatic ring system in which one carbon atom is replaced with a heteroatom. Heteroatoms to replace the carbon atoms include N, O, and S. Specifically included within the definition of "parent heteroaromatic ring systems" are fused ring systems in which one or more rings are aromatic and one or more rings are saturated or unsaturated, such as, for example, arsindole, chromane, chromene, indole, indoline, xanthene, etc. Typical parent heteroaromatic ring systems include, but are not limited to, carbazole, imidazole, indazole, indole, indoline, indolizine, isoindole, isoindoline, isoquinoline, isothiazole, isoxazole, naphthyridine, oxadiazole, oxazole, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like.

"Heteroaryl:" refers to a monovalent heteroaromatic radical derived by the removal of one hydrogen atom from a single atom of a parent heteroaromatic ring system. Typical heteroaryl groups include, but are not limited to, radicals derived from carbazole, imidazole, indazole, indole, indoline, indolizine, isoindole, isoindoline, isoquinoline, isothiazole, isoxazole, naphthyridine, oxadiazole, oxazole, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In preferred embodiments, the heteroaryl group is a 5-20 membered heteroaryl, with 5-10 membered heteroaryl being particularly preferred.

"Cycloheteroalkyl:" refers to a saturated or unsaturated monocyclic or bicyclic alkyl radical in which one carbon atom is replaced with N, O or S. In certain specified embodiments the cycloheteroalkyl may contain up to four heteroatoms independently selected from N, O or S. Typical cycloheteroalkyl moieties include, but are not limited to, radicals derived from imidazolidine, morpholine, piperazine, piperidine, pyrazolidine, pyrrolidine, quinuclidine, and the like. In preferred embodiments, the cycloheteroalkyl is a 3-6 membered cycloheteroalkyl.

"Cycloheteroalkanyl:" refers to a saturated monocyclic or bicyclic alkanyl radical in which one carbon atom is replaced with N, O or S. In certain specified embodiments the cycloheteroalkanyl may contain up to four heteroatoms independently selected from N, O or S. Typical cycloheteroalkanyl moieties include, but are not limited to, radicals derived from imidazolidine, morpholine, piperazine, piperidine, pyrazolidine, pyrrolidine, quinuclidine, and the like. In preferred embodiments, the cycloheteroalkanyl is a 3-6 membered cycloheteroalkanyl.

"Cycloheteroalkenyl:" refers to a saturated monocyclic or bicyclic alkenyl radical in which one carbon atom is replaced with N, O or S. In certain specified embodiments the cyclo- heteroalkenyl may contain up to four heteroatoms independently selected from N, O or S. Typical cycloheteroalkenyl moieties include, but are not limited to, radicals derived from imidazoline, pyrazoline, pyrroline, indoline, pyran, and the like. In preferred embodiments, the cycloheteroalkanyl is a 3-6 membered cycloheteroalkanyl.

"Substituted:" refers to a radical in which one or more hydrogen atoms are each independently replaced with the same or different substituent(s). Typical substituents include, but are not limited to, —X, —R, —O⁻, =O, —OR, —O—OR, —SR, —S⁻, =S, —NRR, =NR, —CX₃, —CN, —OCN, —SCN, —NCO, —NCS, —NO, —NO₂, =N₂, —N₃, —NHOH, —S(O)₂O⁻, —S(O)₂OH, —S(O)₂R, —P(O)(O⁻)₂, —P(O)(OH)₂, —C(O)R, —C(O)X, —C(S)R, —C(S)X, —C(O)OR, —C(O)O⁻, —C(S)OR, —C(O)SR, —C(S)SR, —C(P)NRR, —C(S)NRR and —C(NR)NRR, where each X is independently a halogen (preferably —F, —Cl or —Br) and each R is independently —H, alkyl, alkanyl, alkenyl, alkynyl, alkylidene, alkylidyne, aryl, arylalkyl, arylheteroalkyl, heteroaryl, heteroarylalkyl or heteroaryl-heteroalkyl, as defined herein. Preferred substituents include hydroxy, halogen, $C_{1-8}$alkyl, $C_{1-8}$alkanyloxy, fluorinated alkanyloxy, fluorinated alkyl, $C_{1-8}$alkylthio, $C_{3-8}$cycloalkyl, $C_{3-8}$cycloalkanyloxy, nitro, amino, $C_{1-8}$alkylamino, $C_{1-8}$dialkylamino, $C_{3-8}$cycloalkylamino, cyano, carboxy, $C_{1-7}$alkanyloxycarbonyl, $C_{1-7}$alkylcarbonyloxy, formyl, carbamoyl, phenyl, aroyl, carbamoyl, amidino, ($C_{1-8}$alkylamino)carbonyl, (arylamino)carbonyl and aryl($C_{1-8}$alkyl)carbonyl.

With reference to substituents, the term "independently" means that when more than one of such substituent is possible, such-substituents may be the same or different from each other.

Throughout this disclosure, the terminal portion of the designated side chain is described first, followed by the adjacent functionality toward the point of attachment. Thus, for example, a "phenyl$C_{1-6}$alkanylaminocarbonyl$C_{1-6}$alkyl" substituent refers to a group of the formula

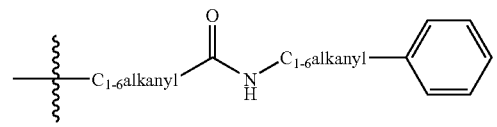

An embodiment of the present invention is directed to compounds of Formula (I) wherein the structure of Formula (I) is as defined below.

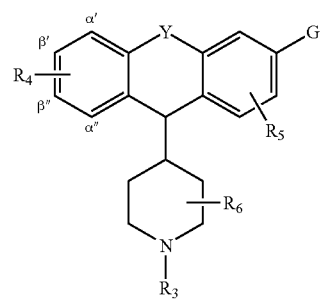

Formula (I)

The present invention is directed to analgesic and antipyretic uses of compositions comprising a compound of Formula (I):

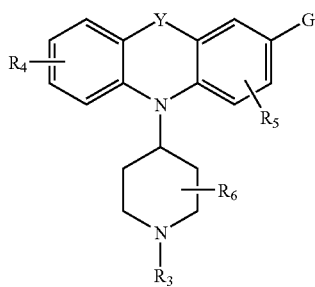

Formula (I)

wherein:
G is —C(Z)N(R₁)R₂, $C_{6-10}$aryl, or a heterocycle selected from the group consisting of: imidazolyl, triazolyl, tetrazolyl, oxadiazolyl, thiadiazolyl, oxathiadiazolyl, imidazolinyl, tetrahydropyrimidinyl, thienyl, pyrazolyl, pyrimidinyl, triazinyl, furyl, indazolyl, indolyl, indolinyl, isothiazolyl, isoxazolyl, oxazolyl, isoxadiazolyl, benzoxazolyl, quinolinyl, isoquinolinyl, and pyridinyl; wherein the $C_{6-10}$aryl and the heterocycles of G are optionally substituted with one to three substituents independently selected from the group consisting of $C_{1-8}$alkanyl, $C_{2-8}$alkenyl, $C_{2-8}$alkynyl, $C_{1-8}$alkanyloxy, hydroxy($C_{1-8}$)alkanyl, carboxy($C_{1-8}$)alkanyl, $C_{1-8}$alkanylcarbonylamino, halogen, hydroxy, cyano, nitro, oxo, thioxo, amino, $C_{1-6}$alkanylamino, di($C_{1-6}$alkanyl) amino, $C_{1-8}$alkanylthio, $C_{1-8}$alkanylsulfonyl, $C_{1-8}$alkanylsulfonylamino, aminocarbonyl, aminothiocarbonyl, aminocarbonylamino, aminothiocarbonylamino, $C_{1-8}$alkanylaminocarbonyl, di($C_{1-8}$alkanyl)aminocarbonyl, and $C_{1-6}$alkanyloxycarbonylamino;

$R_1$ is a substituent selected from the group consisting of hydrogen, $C_{1-8}$alkanyl, $C_{2-8}$alkenyl, and $C_{2-8}$alkynyl;

$R_2$ is a substituent selected from the group consisting of hydrogen; $C_{1-8}$alkanyl; $C_{2-8}$alkenyl; $C_{2-8}$alkynyl; $C_{6-10}$aryl; and $C_{1-8}$cycloalkanyl; wherein $C_{1-8}$alkanyl is optionally substituted with one to three substituents independently selected from the group consisting of phenyl, amino, $C_{1-6}$alkanylamino, di($C_{1-6}$alkanyl) amino, $C_{1-6}$alkanyloxy, thio$C_{1-6}$alkanyloxy, hydroxy, fluoro, chloro, cyano, aminocarbonyl, $C_{1-8}$alkanylaminocarbonyl, di($C_{1-8}$alkanyl)aminocarbonyl, $C_{1-6}$alkanyloxycarbonyl, and aryloxy; and wherein any aryl-containing substituents and $C_{1-8}$cycloalkanyl substituents of $R_2$ are optionally substituted with one to three substituents independently selected from the group consisting of $C_{1-8}$alkanyl, $C_{2-8}$alkenyl, $C_{2-8}$alkynyl, $C_{1-8}$alkanyloxy, trifluoromethyl, trifluoromethoxy, phenyl, halogen, cyano, hydroxy, $C_{1-8}$alkanylthio, $C_{1-8}$alkanylsulfonyl, and $C_{1-8}$alkanylsulfonylamino;

or $R_1$ and $R_2$ taken together with the nitrogen to which they are attached form a 5-7 membered cycloheteroalkyl optionally substituted with one to three substituents independently selected from the group consisting of $C_{1-8}$alkanyl, hydroxy($C_{1-8}$)alkanyl, hydroxy, amino, $C_{1-6}$alkanylamino, di($C_{1-6}$alkanyl)amino, and halogen;

$R_3$ is a substituent selected from the group consisting of hydrogen, $C_{1-8}$alkanyl, halo$_{1-3}$($C_{1-8}$)alkanyl, $C_{2-8}$alkenyl, $C_{2-8}$alkynyl, $C_{3-8}$cycloalkanyl, cycloalkanyl($C_{1-8}$) alkanyl, $C_{1-8}$alkanyloxy($C_{1-8}$)alkanyl, $C_{1-8}$alkanylthio ($C_{1-8}$)alkanyl, hydroxy$C_{1-8}$alkanyl, $C_{1-8}$alkanyloxycarbonyl, halo$_{1-3}$($C_{1-8}$)alkanylcarbonyl, formyl, thioformyl, carbamimidoyl, phenylimino($C_{1-8}$) alkanyl, phenyl($C_{1-8}$)alkanyl, phenyl($C_{1-8}$)alkenyl, phenyl($C_{1-8}$)alkynyl, naphthyl($C_{1-8}$)alkanyl and heteroaryl ($C_{1-8}$)alkanyl wherein the heteroaryl is selected from the group consisting of benzo[1,3]dioxolyl, imidazolyl, furanyl, pyridinyl, thienyl, indazolyl, indolyl, indolinyl, isoindolinyl, isoquinolinyl, isothiazolyl, isoxazolyl, oxazolyl, pyrazinyl, pyrazolyl, pyridazinyl, pyrimidinyl, pyrrolyl, quinolinyl, isoquinolinyl, tetrazolyl, thiazolyl; wherein phenyl, naphthyl and heteroaryl are optionally substituted with one to three substituents independently selected from the group consisting of $C_{1-6}$alkanyl, $C_{2-6}$alkenyl, $C_{1-6}$alkanyloxy, amino, $C_{1-6}$alkanylamino, di($C_{1-6}$alkanyl)amino, $C_{1-6}$alkanylcarbonyl, $C_{1-6}$alkanylcarbonyloxy, $C_{1-6}$alkanylcarbonylamino, $C_{1-6}$alkanylthio, $C_{1-6}$alkanylsulfonyl, halogen, hydroxy, cyano, fluoro($C_{1-6}$)alkanyl, thioureido, and fluoro($C_{1-6}$)alkanyloxy; alternatively, when phenyl and heteroaryl are optionally substituted with alkanyl or alkanloxy substituents attached to adjacent carbon atoms, the two substituents can together form a fused cyclic alkanyl or cycloheteroalkanyl selected from the group consisting of —(CH₂)₃₋₅—, —O(CH₂)₂₋₄—, —(CH₂)₂₋₄O—, and —O(CH₂)₁₋₃O—;

$R_4$ is one to three substituents independently selected from the group consisting of hydrogen; $C_{1-6}$alkanyl; $C_{2-6}$alkenyl; $C_{2-6}$alkynyl; aryl($C_{2-6}$)alkynyl; $C_{1-6}$alkanyloxy; amino; $C_{1-6}$alkanylamino; di($C_{1-6}$alkanyl)amino; $C_{6-10}$arylamino wherein $C_{6-10}$aryl is optionally substituted with one to three substituents independently selected from the group consisting of $C_{1-6}$alkanyl, $C_{1-6}$alkoxy, halogen, and hydroxy; formylamino; pyridinylamino; $C_{1-6}$alkanylcarbonyl; $C_{1-6}$alkanylcarbonyloxy; $C_{1-6}$alkanyloxycarbonyl; aminocarbonyl; $C_{1-6}$alkanylaminocarbonyl; di($C_{1-6}$alkanyl)aminocarbonyl; $C_{1-6}$alkanylcarbonylamino; $C_{1-6}$alkanylthio; $C_{1-6}$alkanylsulfonyl; halogen; hydroxy; cyano; hydroxycarbonyl; $C_{6-10}$aryl; chromanyl; chromenyl; furanyl; imidazolyl; indazolyl; indolyl; indolinyl; isoindolinyl; isoquinolinyl; isothiazolyl; isoxazolyl; naphthyridinyl; oxazolyl; pyrazinyl; pyrazolyl; pyridazinyl; pyridinyl; pyrimidinyl; pyrrolyl; quinazolinyl; quinolinyl; quinolizinyl; quinoxalinyl; tetrazolyl; thiazolyl; thienyl; fluoroalkanyl and fluoroalkanyloxy; or optionally, when $R_4$ is two substituents attached to adjacent carbon atoms, the two substituents together form a single fused moiety, wherein the fused moiety is —(CH₂)₃₋₅—, —O(CH₂)₂₋₄—, —(CH₂)₂₋₄O—, —O(CH₂)₁₋₃O—, or —S—C(NH₂)═N—;

$R_5$ is one to two substituents independently selected from the group consisting of hydrogen, $C_{1-6}$alkanyl, $C_{2-6}$alkenyl, $C_{1-6}$alkanyloxy, amino, $C_{1-6}$alkanylamino, di($C_{1-6}$alkanyl)amino, $C_{1-6}$alkanylcarbonyl, $C_{1-6}$alkanylcarbonyloxy, $C_{1-6}$alkanyloxycarbonyl, $C_{1-6}$alkanylaminocarbonyl, $C_{1-6}$alkanylcarbonylamino, $C_{1-6}$alkanylthio, $C_{1-6}$alkanylsulfonyl, halogen, hydroxy, cyano, fluoro($C_{1-6}$)alkanyl and fluoro($C_{1-6}$)alkanyloxy;

$R_6$ is one to four substituents independently selected from the group consisting of hydrogen, $C_{1-6}$alkanyl, $C_{2-6}$alkenyl, $C_{1-6}$alkanyloxy, amino, $C_{1-6}$alkanylamino, di($C_{1-6}$alkanyl)amino, $C_{1-6}$alkanylcarbonyl, $C_{1-6}$alkanylcarbonyloxy, $C_{1-6}$alkanyloxycarbonyl, $C_{1-6}$alkanylaminocarbonyl, $C_{1-6}$alkanylcarbonylamino, $C_{1-6}$alkanylthio, $C_{1-6}$alkanylsulfonyl, halogen, hydroxy, cyano, fluoro($C_{1-6}$)alkanyl and fluoro($C_{1-6}$)alkanyloxy;

Y is O or S;

Z is O, S, NH, N($C_{1-6}$alkanyl), N(OH), N(O$C_{1-6}$alkanyl), or N(phenyl);

and enantiomers, diastereomers, tautomers, solvates, or pharmaceutically acceptable salts thereof.

Embodiments of the present invention include compounds and compositions comprising compounds of Formula (I) wherein, preferably:

a) G is —C(Z)N($R_1$)$R_2$, phenyl, or a heterocycle selected from the group consisting of imidazolyl, triazolyl, tetrazolyl, oxadiazolyl, thiadiazolyl, oxathiadiazolyl, imidazolinyl, tetrahydropyrimidinyl, thienyl, pyrazolyl, pyrimidinyl, triazinyl, isothiazolyl, isoxazolyl, oxazolyl, isoxadiazolyl, and pyridinyl; wherein phenyl and the heterocycles of G are optionally substituted with one to three substituents independently selected from the group consisting of $C_{1-8}$alkanyl, $C_{1-8}$alkanyloxy, hydroxy($C_{1-8}$)alkanyl, carboxy($C_{1-8}$)alkanyl, $C_{1-8}$alkanylcarbonylamino, halogen, hydroxy, cyano, oxo, thioxo, amino, $C_{1-6}$alkanylamino, di($C_{1-6}$alkanyl)amino, $C_{1-8}$alkanylthio, aminocarbonyl, aminothiocarbonyl, $C_{1-8}$alkanylaminocarbonyl, di($C_{1-8}$alkanyl)aminocarbonyl, and $C_{1-6}$alkanyloxycarbonylamino;

b) G is —C(Z)N($R_1$)$R_2$, phenyl, or a heterocycle selected from the group consisting of imidazolyl, tetrazolyl, oxadiazolyl, thiadiazolyl, oxathiadiazolyl, imidazolinyl, thienyl, pyrazolyl, pyrimidinyl, triazinyl, isothiazolyl, isoxazolyl, oxazolyl, isoxadiazolyl, and pyridinyl; wherein phenyl and the heterocycles of G (described herein) are optionally substituted with one to three substituents independently selected from the group consisting of $C_{1-4}$alkanyl, $C_{1-4}$alkanyloxy, hydroxy($C_{1-4}$)alkanyl, carboxy($C_{1-4}$)alkanyl, $C_{1-4}$alkanylcarbonylamino, hydroxy, cyano, oxo, thioxo, amino, $C_{1-6}$alkanylamino, di($C_{1-6}$alkanyl)amino, $C_{1-8}$alkanylthio, aminocarbonyl, aminothiocarbonyl, $C_{1-8}$alkanylaminocarbonyl, and di($C_{1-8}$alkanyl)aminocarbonyl;

c) G is —C(Z)N($R_1$)$R_2$, phenyl, or a heterocycle selected from the group consisting of imidazolyl, tetrazolyl, oxadiazolyl, thiadiazolyl, oxathiadiazolyl, thienyl, isothiazolyl, isoxazolyl, isoxadiazolyl, and pyridinyl; wherein phenyl and the heterocycles of G (described herein) are optionally substituted with one to three substituents independently selected from the group consisting of $C_{1-4}$alkanyl, $C_{1-4}$alkanyloxy, hydroxy($C_{1-4}$)alkanyl, $C_{1-4}$alkanylcarbonylamino, hydroxy, cyano, oxo, thioxo, and aminocarbonyl;

d) G is —C(Z)N($R_1$)$R_2$, phenyl, or a heterocycle selected from the group consisting of tetrazolyl, oxadiazolyl, and pyridinyl, wherein the phenyl and the heterocycles of G are optionally substituted with one to three substituents independently selected from the group consisting of $C_{1-4}$alkanylcarbonylamino and oxo;

e) G is N,N-diethylaminocarbonyl, 2-methylcarbonylaminophenyl, N-N-diethylamidino, pyridin-3-yl, 3-hydroxypyrrolidin-1-ylcarbonyl, N-ethylaminocarbonyl, 1H-tetrazol-4-yl, pyridine-4-yl, 4H-[1,2,4]-oxadiazol-5-oxo-3-yl, N,N-dimethylaminocarbonyl, or pyrrolidin-1-ylcarbonyl;

f) $R_1$ is a substituent selected from the group consisting of hydrogen and $C_{1-4}$alkanyl;

g) $R_1$ is selected from the group consisting of hydrogen, methyl, ethyl, and propyl;

h) $R_1$ is selected from the group consisting of hydrogen, methyl, or ethyl;

i) $R_1$ is selected from the group consisting of hydrogen and ethyl;

j) $R_2$ is selected from the group consisting of hydrogen; $C_{1-4}$alkanyl; phenyl; and $C_{1-6}$cycloalkanyl; wherein $C_{1-4}$alkanyl is optionally substituted with one to three substituents independently selected from the group consisting of phenyl, amino, $C_{1-6}$alkanylamino, di($C_{1-6}$alkanyl)amino, $C_{1-4}$alkanyloxy, hydroxy, fluoro, chloro, cyano, aminocarbonyl, $C_{1-8}$alkanylaminocarbonyl, di($C_{1-8}$alkanyl)aminocarbonyl, and phenoxy; and wherein any phenyl-containing substituents and $C_{1-6}$cycloalkanyl substituents of $R_2$ are optionally substituted with one to three substituents independently selected from the group consisting of $C_{1-8}$alkanyl, $C_{1-8}$alkanyloxy, trifluoromethyl, phenyl, fluoro, hydroxy, $C_{1-8}$alkanylthio, $C_{1-8}$alkanylsulfonyl, and $C_{1-8}$alkanylsulfonylamino; or $R_1$ and $R_2$ taken together with the nitrogen to which they are attached form a 5-7 membered cycloheteroalkyl optionally substituted with one to three substituents independently selected from the group consisting of $C_{1-4}$alkanyl, hydroxy($C_{1-4}$)alkanyl, hydroxy, amino, $C_{1-6}$alkanylamino, di($C_{1-6}$alkanyl)amino, and fluoro;

k) $R_2$ is selected from the group consisting of hydrogen, $C_{1-4}$alkanyl, phenyl, and $C_{1-6}$cycloalkanyl, wherein $C_{1-4}$alkanyl is optionally substituted with one to three substituents independently selected from the group consisting of phenyl, $C_{1-4}$alkanyloxy, hydroxy, fluoro, aminocarbonyl, $C_{1-8}$alkanylaminocarbonyl, di($C_{1-8}$alkanyl)aminocarbonyl, and phenoxy; and wherein any phenyl-containing substituent of $R_2$ is optionally substituted with one to three substituents independently selected from the group consisting of $C_{1-6}$alkanyl, $C_{1-6}$alkanyloxy, fluoro, hydroxy, and $C_{1-6}$alkanylthio; or $R_1$ and $R_2$ taken together with the nitrogen to which they are attached form a 5-7 membered cycloheteroalkyl optionally substituted with one to three substituents independently selected from the group consisting of $C_{1-4}$alkanyl and hydroxy;

l) $R_2$ is selected from the group consisting of hydrogen, $C_{1-4}$alkanyl and phenyl, wherein $C_{1-4}$alkanyl is optionally substituted with one to three substituents independently selected from the group consisting of phenyl, $C_{1-4}$alkanyloxy, hydroxy, fluoro, and phenoxy; and wherein any phenyl-containing substituent of $R_2$ is optionally substituted with one to three substituents independently selected from the group consisting of $C_{1-6}$alkanyl, $C_{1-6}$alkanyloxy, fluoro, and hydroxy; or $R_1$ and $R_2$ taken together with the nitrogen to which they are attached form a pyrrolidinyl or piperidinyl ring wherein said pyrrolidinyl or piperidinyl is optionally substituted with a substituent selected from the group consisting of $C_{1-3}$alkanyl and hydroxy;

m) $R_2$ is selected from the group consisting of hydrogen and $C_{1-4}$alkanyl; or $R_1$ and $R_2$ taken together with the nitrogen to which they are attached form a pyrrolidinyl ring optionally substituted with hydroxy;

n) $R_2$ is hydrogen or ethyl; or $R_1$ and $R_2$ taken together with the nitrogen to which they are attached form a pyrrolidinyl ring optionally substituted with hydroxy;

o) $R_3$ is selected from the group consisting of hydrogen, $C_{1-8}$alkanyl, $C_{2-8}$alkenyl, $C_{2-8}$alkynyl, $C_{1-8}$alkanyloxy($C_{1-8}$)alkanyl, $C_{1-8}$alkanylthio($C_{1-8}$)alkanyl, hydroxy$C_{1-8}$alkanyl, thioformyl, phenylimino($C_{1-8}$)alkanyl, phenyl($C_{1-8}$)alkanyl, and heteroaryl($C_{1-8}$)alkanyl wherein heteroaryl is selected from the group consisting of benzo[1,3]dioxolyl, imidazolyl, furanyl, pyridinyl, thienyl, indolyl, indolinyl, isoquinolinyl, pyrazinyl, pyrazolyl, pyridazinyl, pyrimidinyl, pyrrolyl, quinolinyl, isoquinolinyl, tetrazolyl; wherein phenyl and heteroaryl are optionally substituted with one to three substituents independently selected from the group consisting of $C_{1-6}$alkanyloxy and hydroxy; or optionally, when phenyl and heteroaryl are optionally substituted with two substituents attached to adjacent carbon atoms, the two substituents together form a single fused moiety; wherein the moiety is selected from —O(CH$_2$)$_{1-3}$O—;

p) $R_3$ is selected from the group consisting of hydrogen, methyl, allyl, 2-methyl-allyl, propynyl, hydroxyethyl, methylthioethyl, methoxyethyl, thioformyl, phenyliminomethyl, phenethyl, and heteroaryl($C_{1-8}$)alkanyl wherein the heteroaryl is selected from the group consisting of benzo[1,3]dioxolyl, imidazolyl, furanyl, pyridinyl, thienyl, pyrimidinyl, pyrrolyl, quinolinyl, isoquinolinyl, tetrazolyl; wherein the phenyl in any phenyl-containing substituent is optionally substituted with one hydroxyl group;

q) $R_3$ is hydrogen, $C_{1-8}$alkanyl, $C_{2-8}$alkenyl, phenyl($C_{1-8}$)alkanyl, or heteroaryl($C_{1-8}$)alkanyl wherein the heteroaryl is imidazolyl, furanyl, pyridinyl, or thienyl;

r) $R_3$ is hydrogen, methyl, allyl, or heteroarylmethyl wherein heteroaryl is selected from the group consisting of benzo[1,3]dioxolyl, imidazolyl, furanyl, pyridinyl, and thienyl;

s) $R_3$ is hydrogen, methyl, 3-methyl-2-butenyl, benzyl, phenethyl, or heteroarylmethyl wherein the heteroaryl is furanyl, imidazolyl, pyridinyl, or thienyl;

t) $R_4$ is one to three substituents independently selected from the group consisting of hydrogen; $C_{1-6}$alkanyl; $C_{1-6}$alkanyloxy; $C_{6-10}$arylamino wherein $C_{6-10}$aryl is optionally substituted with one to three substituents independently selected from the group consisting of $C_{1-6}$alkanyl, $C_{1-6}$alkoxy, halogen, and hydroxy; formylamino; pyridinylamino; aminocarbonyl; $C_{1-6}$alkanylaminocarbonyl; $C_{1-6}$alkanylcarbonylamino; halogen; hydroxy; $C_{6-10}$aryl; chromanyl; chromenyl; furanyl; imidazolyl; indazolyl; indolyl; indolinyl; isoindolinyl; isoquinolinyl; isothiazolyl; isoxazolyl; naphthyridinyl; oxazolyl; pyrazinyl; pyrazolyl; pyridazinyl; pyridinyl; pyrimidinyl; pyrrolyl; quinazolinyl; quinolinyl; quinolizinyl; quinoxalinyl; tetrazolyl; thiazolyl; and thienyl;

u) $R_4$ is one to two substituents independently selected from the group consisting of hydrogen, $C_{1-4}$alkanyl, $C_{1-4}$alkanyloxy, halogen, phenyl, furanyl, imidazolyl, indazolyl, indolyl, indolinyl, isoindolinyl, isoquinolinyl, isothiazolyl, isoxazolyl, oxazolyl, pyrazinyl, pyrazolyl, pyridazinyl, pyridinyl, pyrimidinyl, pyrrolyl, quinolinyl, tetrazolyl, thiazolyl, thienyl, aminocarbonyl; and hydroxy;

v) $R_4$ is one to two substituents independently selected from the group consisting of hydrogen, methyl, methoxy, bromo, fluoro, α'- or β'-phenyl, α'- or β'-pyridinyl, α'- or β'-furanyl, aminocarbonyl; and hydroxy;

w) $R_4$ is one substituent selected from the group consisting of hydrogen, methoxy, hydroxyl, hydroxycarbonyl, and aminocarbonyl;

x) $R_4$ is one substituent and is hydrogen, methoxy, or hydroxy;

y) $R_5$ is one to two substituents independently selected from the group consisting of hydrogen and halogen;

z) $R_5$ is hydrogen;

aa) $R_6$ is one to four substituents independently selected from the group consisting of hydrogen, $C_{1-6}$alkanyl, $C_{2-6}$alkenyl, $C_{1-6}$alkanyloxy, halogen, hydroxy, fluoro($C_{1-6}$)alkanyl and fluoro($C_{1-6}$)alkanyloxy;

bb) $R_6$ is one to two substituents independently selected from the group consisting of hydrogen and $C_{1-4}$alkanyl;

cc) $R_6$ is one to two substituents independently selected from the group consisting of hydrogen and methyl;

dd) $R_6$ is hydrogen;

ee) Y is O or S;

ff) Y is O;

gg) Z is O, NH, N($C_{1-6}$alkanyl), N(OH), N(O$C_{1-6}$alkanyl), or N(phenyl);

hh) Z is O, NH, or N(OH);

ii) Z is O or NH;

jj) Z is O;

kk) $R_4$ is hydrogen and Y is O;

ll) $R_4$ is α'-hydroxy and Y is O;

mm) $R_4$ is hydrogen and Y is S;

nn) $R_4$ is α'-hydroxy and Y is S;

and combinations of a) through nn) above.

embodiment of the present invention is a compound of Formula (I) or a composition comprising a compound of Formula (I) whereinOne embodiment of the present invention is a compound of Formula (I) or a composition comprising a compound of Formula (I) wherein:

G is —C(Z)N($R_1$)$R_2$, phenyl, or a heterocycle selected from the group consisting of imidazolyl, triazolyl, tetrazolyl, oxadiazolyl, thiadiazolyl, oxathiadiazolyl, imidazolinyl, tetrahydropyrimidinyl, thienyl, pyrazolyl, pyrimidinyl, triazinyl, isothiazolyl, isoxazolyl, oxazolyl, isoxadiazolyl, and pyridinyl; wherein phenyl and the heterocycles of G are optionally substituted with one to three substituents independently selected from the group consisting of $C_{1-8}$alkanyl, $C_{1-8}$alkanyloxy, hydroxy($C_{1-8}$)alkanyl, carboxy($C_{1-8}$)alkanyl, $C_{1-8}$alkanylcarbonylamino, halogen, hydroxy, cyano, oxo, thioxo, amino, $C_{1-6}$alkanylamino, di($C_{1-6}$alkanyl)amino, $C_{1-8}$alkanylthio, aminocarbonyl, aminothiocarbonyl, $C_{1-8}$alkanylaminocarbonyl, di($C_{1-8}$alkanyl)aminocarbonyl, and $C_{1-6}$alkanyloxycarbonylamino;

$R_1$ is hydrogen or $C_{1-4}$alkanyl;

$R_2$ is selected from the group consisting of hydrogen; $C_{1-4}$alkanyl; phenyl; and $C_{1-6}$cycloalkanyl; wherein $C_{1-4}$alkanyl is optionally substituted with one to three substituents independently selected from the group consisting of phenyl, amino, $C_{1-6}$alkanylamino, di($C_{1-6}$alkanyl)amino, $C_{1-4}$alkanyloxy, hydroxy, fluoro, chloro, cyano, aminocarbonyl, $C_{1-8}$alkanylaminocarbonyl, di($C_{1-8}$alkanyl)aminocarbonyl, and phenoxy; and wherein the phenyl and $C_{1-6}$cycloalkanyl substituents of $R_2$ are optionally substituted with one to three substituents independently selected from the group consisting of $C_{1-8}$alkanyl, $C_{1-8}$alkanyloxy, trifluoromethyl, phenyl, fluoro, hydroxy, $C_{1-8}$alkanylthio, $C_{1-8}$alkanylsulfonyl, and $C_{1-8}$alkanylsulfonylamino; or $R_1$ and $R_2$ taken together with the nitrogen to which they are attached form a 5-7 membered cycloheteroalkyl optionally substituted with one to three substituents independently selected from the group consisting of $C_{1-4}$alkanyl, hydroxy($C_{1-4}$)alkanyl, hydroxy, amino, $C_{1-6}$alkanylamino, di($C_{1-6}$alkanyl)amino, and fluoro;

$R_3$ is selected from the group consisting of hydrogen, $C_{1-8}$alkanyl, $C_{2-8}$alkenyl, $C_{2-8}$alkynyl, $C_{1-8}$alkanyloxy($C_{1-8}$)alkanyl, $C_{1-8}$alkanylthio($C_{1-8}$)alkanyl, hydroxy$C_{1-8}$alkanyl, thioformyl, phenylimino($C_{1-8}$)alkanyl, phenyl($C_{1-8}$)alkanyl, and heteroaryl($C_{1-8}$)alkanyl wherein heteroaryl is selected from the group consisting of benzo[1,3]dioxolyl, imidazolyl, furanyl, pyridinyl, thienyl, indolyl, indolinyl, isoquinolinyl, pyrazinyl, pyrazolyl, pyridazinyl, pyrimidinyl, pyrrolyl, quinolinyl, isoquinolinyl, tetrazolyl; wherein phenyl and heteroaryl are optionally substituted with one to three substituents independently selected from the group consisting of $C_{1-6}$alkanyloxy and hydroxy; or optionally, when phenyl and heteroaryl are optionally substituted with two substituents attached to adjacent carbon atoms, the two substituents together form a single fused moiety; wherein the moiety is selected from —O(CH$_2$)$_{1-3}$O—;

$R_4$ is one to three substituents independently selected from the group consisting of hydrogen; $C_{1-6}$alkanyl; $C_{1-6}$alkanyloxy; $C_{6-10}$arylamino wherein $C_{6-10}$aryl is optionally substituted with one to three substitutents independently selected from the group consisting of $C_{1-6}$alkanyl, $C_{1-6}$alkoxy, halogen, and hydroxy; formylamino; pyridinylamino; aminocarbonyl; $C_{1-6}$alkanylaminocarbonyl; $C_{1-6}$alkanylcarbonylamino; halogen; hydroxy; $C_{6-10}$aryl; chromanyl; chromenyl; furanyl; imidazolyl; indazolyl; indolyl; indolinyl; isoindolinyl; isoquinolinyl; isothiazolyl; isoxazolyl; naphthyridinyl; oxazolyl; pyrazinyl; pyrazolyl; pyridazinyl; pyridinyl; pyrimidinyl; pyrrolyl; quinazolinyl; quinolinyl; quinolizinyl; quinoxalinyl; tetrazolyl; thiazolyl; and thienyl;

$R_5$ is one to two substituents independently selected from the group consisting of hydrogen and halogen;

$R_6$ is one to four substituents independently selected from the group consisting of hydrogen, $C_{1-6}$alkanyl, $C_{2-6}$alkenyl, $C_{1-6}$alkanyloxy, halogen, hydroxy, fluoro($C_{1-6}$)alkanyl and fluoro($C_{1-6}$)alkanyloxy;

Y is O or S;

Z is O, NH, N($C_{1-6}$alkanyl), N(OH), N(O$C_{1-6}$alkanyl), or N(phenyl); and enantiomers, diastereomers, tautomers, solvates, and pharmaceutically acceptable salts thereof.

Another embodiment of the present invention is a compound of Formula (I) or a composition comprising a compound of Formula (I) wherein:

G is —C(Z)N(R$_1$)R$_2$, phenyl, or a heterocycle selected from the group consisting of imidazolyl, tetrazolyl, oxadiazolyl, thiadiazolyl, oxathiadiazolyl, imidazolinyl, thienyl, pyrazolyl, pyrimidinyl, triazinyl, isothiazolyl, isoxazolyl, oxazolyl, isoxadiazolyl, and pyridinyl; wherein phenyl and the heterocycles of G (described herein) are optionally substituted with one to three substituents independently selected from the group consisting of $C_{1-4}$alkanyl, $C_{1-4}$alkanyloxy, hydroxy($C_{1-4}$)alkanyl, carboxy($C_{1-4}$)alkanyl, $C_{1-4}$alkanylcarbonylamino, hydroxy, cyano, oxo, thioxo, amino, $C_{1-6}$alkanylamino, di($C_{1-6}$alkanyl)amino, $C_{1-8}$alkanylthio, aminocarbonyl, aminothiocarbonyl, $C_{1-8}$alkanylaminocarbonyl, and di($C_{1-8}$alkanyl)aminocarbonyl;

$R_1$ is selected from the group consisting of hydrogen, methyl, ethyl, and propyl;

$R_2$ is selected from the group consisting of hydrogen, $C_{1-4}$alkanyl, phenyl, and $C_{1-6}$cycloalkanyl; wherein $C_{1-4}$alkanyl is optionally substituted with one to three substituents independently selected from the group consisting of phenyl, $C_{1-4}$alkanyloxy, hydroxy, fluoro, aminocarbonyl, $C_{1-8}$alkanylaminocarbonyl, di($C_{1-8}$alkanyl)aminocarbonyl, and phenoxy; and wherein any phenyl-containing substituent of $R_2$ is optionally substituted with one to three substituents independently selected from the group consisting of $C_{1-6}$alkanyl, $C_{1-6}$alkanyloxy, fluoro, hydroxy, and $C_{1-6}$alkanylthio; or $R_1$ and $R_2$ taken together with the nitrogen to which they are attached form a pyrrolidinyl or piperidinyl ring wherein said pyrrolidinyl or piperidinyl is optionally substituted with a substituent selected from the group consisting of $C_{1-3}$alkanyl and hydroxy;

$R_3$ is selected from the group consisting of hydrogen, methyl, allyl, 2-methyl-allyl, propynyl, hydroxyethyl, methylthioethyl, methoxyethyl, thioformyl, phenyliminomethyl, phenethyl, and heteroaryl($C_{1-8}$)alkanyl wherein the heteroaryl is selected from the group consisting of benzo[1,3]dioxolyl, imidazolyl, furanyl, pyridinyl, thienyl, pyrimidinyl, pyrrolyl, quinolinyl, isoquinolinyl, tetrazolyl wherein the phenyl in any phenyl-containing substituent is optionally substituted with one hydroxyl group;

$R_4$ is one to two substituents independently selected from the group consisting of hydrogen, $C_{1-4}$alkanyl, $C_{1-4}$alkanyloxy, halogen, phenyl, furanyl, imidazolyl, indazolyl, indolyl, indolinyl, isoindolinyl, isoquinolinyl, isothiazolyl, isoxazolyl, oxazolyl, pyrazinyl, pyrazolyl, pyridazinyl, pyridinyl, pyrimidinyl, pyrrolyl, quinolinyl, tetrazolyl, thiazolyl, thienyl, aminocarbonyl; and hydroxy;

$R_5$ is hydrogen;

$R_6$ is one to two substituents independently selected from the group consisting of hydrogen and $C_{1-4}$alkanyl;

Y is O or S;

Z is O, NH, or N(OH); and enantiomers, diastereomers, tautomers, solvates, and pharmaceutically acceptable salts thereof.

Another embodiment of the present invention is directed to compounds and to compositions comprising a compound of Formula (I) wherein:

G is selected from —C(Z)N(R$_1$)R$_2$, phenyl, or a heterocycle selected from the group consisting of imidazolyl, tetrazolyl, oxadiazolyl, thiadiazolyl, oxathiadiazolyl, thienyl, isothiazolyl, isoxazolyl, isoxadiazolyl, and pyridinyl; wherein phenyl and the heterocycles of G are optionally substituted with one to three substituents independently selected from the group consisting of $C_{1-4}$alkanyl, $C_{1-4}$alkanyloxy, hydroxy($C_{1-4}$)alkanyl, $C_{1-4}$alkanylcarbonylamino, hydroxy, cyano, oxo, thioxo, and aminocarbonyl; $R_1$ is hydrogen, methyl, or ethyl;

$R_2$ is independently selected from the group consisting of hydrogen, $C_{1-4}$alkanyl and phenyl; wherein $C_{1-4}$alkanyl is optionally substituted with one to three substituents independently selected from the group consisting of phenyl, $C_{1-4}$alkanyloxy, hydroxy, fluoro, and phenoxy; and wherein any phenyl-containing substituent of $R_2$ is optionally substituted with one to three substituents independently selected from the group consisting of $C_{1-6}$alkanyl, $C_{1-6}$alkanyloxy, fluoro, and hydroxy; or $R_1$ and $R_2$ taken together with the nitrogen to which they are attached form a pyrrolidinyl or piperidinyl ring wherein said pyrrolidinyl or piperidinyl are optionally substituted with a substituent selected from the group consisting of $C_{1-3}$alkanyl and hydroxy;

$R_3$ is hydrogen, methyl, allyl, or heteroarylmethyl wherein heteroaryl is selected from the group consisting of benzo[1,3]dioxolyl, imidazolyl, furanyl, pyridinyl, and thienyl;

$R_4$ is one to two substituents independently selected from the group consisting of hydrogen, $C_{1-4}$alkanyl, $C_{1-4}$alkanyloxy, halogen, phenyl, furanyl, imidazolyl, indazolyl, indolyl, indolinyl, isoindolinyl, isoquinolinyl, isothiazolyl, isoxazolyl, oxazolyl, pyrazinyl, pyrazolyl, pyridazinyl, pyridinyl, pyrimidinyl, pyrrolyl, quinolinyl, tetrazolyl, thiazolyl, thienyl, aminocarbonyl; and hydroxy;

$R_6$ is one to two substituents independently selected from the group consisting of hydrogen and methyl;

Y is O or S;

Z is O or NH; and enantiomers, diasteromers, tautomers, solvates, and pharmaceutically acceptable salts thereof.

Another embodiment of the present invention is a compound of Formula (I) or a composition comprising a compound of Formula (I) wherein:

G is selected from $—C(Z)N(R_1)R_2$, 2-methylcarbonylaminophenyl, 2-aminocarbonyl-phenyl, 1H-tetrazol-4-yl, 2-methyl-tetrazol-5-yl, 4H-[1,2,4]-oxadiazol-5-oxo-3-yl, 4H-[1,2,4]-oxadiazol-5-thioxo-3-yl, 4H-[1,2,4]thiadiazol-5-oxo-3-yl, [1,2,3,5]oxathiadiazol-2-oxo-4-yl, or pyridin-3-yl;

$R_1$ is hydrogen, methyl, or ethyl;

$R_2$ is selected from the group consisting of hydrogen, $C_{1-4}$alkanyl and phenyl; wherein $C_{1-4}$alkanyl is optionally substituted with one to three substituents independently selected from the group consisting of phenyl, $C_{1-4}$alkanyloxy, hydroxy, fluoro, and phenoxy; and wherein any phenyl-containing substituent of $R_2$ is optionally substituted with one to three substituents independently selected from the group consisting of $C_{1-6}$alkanyl, $C_{1-6}$alkanyloxy, fluoro, and hydroxy;

or $R_1$ and $R_2$ taken together with the nitrogen to which they are attached form a pyrrolidinyl or piperidinyl ring;

$R_3$ is selected from the group consisting of hydrogen, $C_{1-8}$alkanyl, $C_{2-8}$alkenyl, $C_{2-8}$alkynyl, $C_{1-8}$alkanyloxy $(C_{1-8})$alkanyl, $C_{1-8}$alkanylthio$(C_{1-8})$alkanyl, hydroxy$C_{1-8}$alkanyl, thioformyl, phenylimino$(C_{1-8})$alkanyl, phenyl$(C_{1-8})$alkanyl, and heteroaryl$(C_{1-8})$alkanyl wherein heteroaryl is selected from the group consisting of hydrogen, methyl, allyl, or heteroarylmethyl; wherein heteroaryl is selected from the group consisting of benzo[1,3]dioxolyl, imidazolyl, furanyl, pyridinyl, and thienyl; wherein phenyl and heteroaryl are optionally substituted with one to three substituents independently selected from the group consisting of $C_{1-6}$alkanyloxy and hydroxy; or optionally, when phenyl and heteroaryl are optionally substituted with two substituents attached to adjacent carbon atoms, the two substituents together form a single fused moiety; wherein the moiety is selected from $—O(CH_2)_{1-3}O—$;

$R_4$ is one to three substituents independently selected from the group consisting of hydrogen, $C_{1-4}$alkanyl, $C_{1-4}$alkanyloxy, halogen, phenyl, furanyl, imidazolyl, indazolyl, indolyl, indolinyl, isoindolinyl, isoquinolinyl, isothiazolyl, isoxazolyl, oxazolyl, pyrazinyl, pyrazolyl, pyridazinyl, pyridinyl, pyrimidinyl, pyrrolyl, quinolinyl, tetrazolyl, thiazolyl, thienyl, aminocarbonyl; and hydroxy;

$R_5$ is hydrogen;

$R_6$ is one to two substituents independently selected from the group consisting of hydrogen and methyl;

Y is O or S;

Z is O or NH; and enantiomers, diastereomers, tautomers, solvates, and pharmaceutically acceptable salts thereof.

Another embodiment of the present invention is directed to compounds and to compositions comprising a compound of Formula (I) wherein:

G is independently selected from $—C(Z)N(R_1)R_2$, 2-methylcarbonylaminophenyl, 2-aminocarbonyl-phenyl, 1H-tetrazol-4-yl, 2-methyl-tetrazol-5-yl, 4H-[1,2,4]-oxadiazol-5-oxo-3-yl, 4H-[1,2,4]-oxadiazol-5-thioxo-3-yl, 4H-[1,2,4]thiadiazol-5-oxo-3-yl, [1,2,3,5]oxathiadiazol-2-oxo-4-yl, and pyridin-3-yl;

$R_1$ is hydrogen, methyl, or ethyl;

$R_2$ is a substituent selected from the group consisting of hydrogen, $C_{1-4}$alkanyl and phenyl; wherein $C_{1-4}$alkanyl is optionally substituted with one to three substituents independently selected from the group consisting of phenyl, $C_{1-4}$alkanyloxy, hydroxy, and 2,6-dimethyl-phenoxy; and wherein the any phenyl-containing substituent of $R_2$ is optionally substituted with one to three substituents independently selected from the group consisting of $C_{1-6}$alkanyl, $C_{1-6}$alkanyloxy, fluoro, and hydroxy;

or $R_1$ and $R_2$ taken together with the nitrogen to which they are attached form a pyrrolidinyl or piperidinyl ring wherein said pyrrolidinyl or piperidinyl is optionally substituted with a substituent selected from the group consisting of $C_{1-3}$alkanyl and hydroxy;

$R_3$ is a substituent selected from the group consisting of benzo[1,3]dioxol-5-ylmethyl, carbamimidoyl, 1-H-imidazol-4-ylmethyl, phenyliminomethyl, 1-prop-2-ynyl, thioformyl, 2-hydroxyphenyl-methyl, hydroxy-ethyl, methoxy-ethyl, 2-methyl-allyl, 2-methyl-but-2-enyl, allyl, furan-3-ylmethyl, H, Me, methylthioethyl, phenethyl, pyridin-2-yl methyl, and thiophen-2-ylmethyl;

$R_4$ is one to two substituents independently selected from the group consisting of hydrogen, $C_{1-4}$alkanyl, $C_{1-4}$alkanyloxy, halogen, phenyl, furanyl, imidazolyl, indazolyl, indolyl, indolinyl, isoindolinyl, isoquinolinyl, isothiazolyl, isoxazolyl, oxazolyl, pyrazinyl, pyrazolyl, pyridazinyl, pyridinyl, pyrimidinyl, pyrrolyl, quinolinyl, tetrazolyl, thiazolyl, thienyl, aminocarbonyl; and hydroxy;

$R_5$ is hydrogen;

$R_6$ is one to two substituents independently selected from the group consisting of hydrogen and methyl;

Y is O or S; and

Z is O or NH.

Another embodiment of the present invention is directed to compounds, and to compositions comprising a compound of Formula (I) wherein:

G is selected from $—C(Z)N(R_1)R_2$, 2-methylcarbonylaminophenyl, 2-aminocarbonyl-phenyl, 1H-tetrazol-4-yl, 2-methyl-tetrazol-5-yl, 4H-[1,2,4]-oxadiazol-5-oxo-3-yl, 4H-[1,2,4]-oxadiazol-5-thioxo-3-yl, 4H-[1,2,4]thiadiazol-5-oxo-3-yl, [1,2,3,5]oxathiadiazol-2-oxo-4-yl, or pyridin-3-yl;

$R_1$ is hydrogen, methyl, or ethyl;

$R_2$ is a substituent selected from the group consisting of hydrogen, $C_{1-4}$alkanyl and phenyl; wherein $C_{1-4}$alkanyl is optionally substituted with one to three substituents independently selected from the group consisting of phenyl, methoxy, hydroxy, and 2,6-dimethyl-phenoxy; and wherein any phenyl-containing substituent of $R_2$ is optionally substituted with one to three substituents independently selected from the group consisting of $C_{1-6}$alkanyl, $C_{1-6}$alkanyloxy, fluoro, and hydroxy;

or $R_1$ and $R_2$ taken together with the nitrogen to which they are attached form a pyrrolidinyl or piperidinyl ring wherein said pyrrolidinyl or piperidinyl are optionally substituted with a substituent selected from the group consisting of $C_{1-3}$alkanyl and hydroxy; $R_3$ is a substituent selected from the group consisting of benzo[1,3]dioxol-5-ylmethyl, carbamimidoyl, 1-H-imidazol-4-ylmethyl, phenyliminomethyl, 1-prop-2-ynyl, thioformyl, 2-hydroxyphenyl-methyl, hydroxyethyl, methoxyethyl, allyl, furan-3-yl methyl, H, Me, methylthioethyl, and phenethyl;

$R_4$ is one to two substituents independently selected from the group consisting of hydrogen, methyl, methoxy, bromo, fluoro, α'- or β'-phenyl, α'- or β'-pyridinyl, α'- or β'-furanyl, aminocarbonyl; and hydroxy:

$R_5$ is hydrogen;

$R_6$ is one to two substituents independently selected from the group consisting of hydrogen and methyl;

Y is O or S; and

Z is O or NH.

Another embodiment of the present invention is directed to compounds and to compositions comprising a compound of Formula (I) wherein:

G is selected from —C(Z)N($R_1$)$R_2$, 2-methylcarbonylaminophenyl, 2-aminocarbonyl-phenyl, 1H-tetrazol-4-yl, 2-methyl-tetrazol-5-yl, 4H-[1,2,4]-oxadiazol-5-oxo-3-yl, 4H-[1,2,4]-oxadiazol-5-thioxo-3-yl, 4H-[1,2,4]thiadiazol-5-oxo-3-yl, [1,2,3,5]oxathiadiazol-2-oxo-4-yl, or pyridin-3-yl;

$R_1$ is hydrogen, methyl, or ethyl;

$R_2$ is a substituent selected from the group consisting of hydrogen, $C_{1-4}$alkanyl and phenyl; wherein $C_{1-4}$alkanyl is optionally substituted with one to three substituents independently selected from the group consisting of phenyl, methoxy, hydroxy, and 2,6-dimethyl-phenoxy; and wherein any phenyl-containing substituent of $R_2$ is optionally substituted with one to three substituents independently selected from the group consisting of $C_{1-6}$alkanyl, $C_{1-6}$alkanyloxy, fluoro, and hydroxy;

alternatively $R_1$ and $R_2$ are taken together with the nitrogen to which they are attached to form a pyrrolidinyl or piperidinyl ring wherein said pyrrolidinyl or piperidinyl are optionally substituted with a substituent selected from the group consisting of $C_{1-3}$alkanyl and hydroxy;

$R_3$ is a substituent selected from the group consisting of H, benzo[1,3]dioxol-5-ylmethyl, 1-H-imidazol-4-yl methyl, furan-3-ylmethyl, pyridin-2-ylmethyl, and phenyliminomethyl;

$R_4$ is a substituent independently selected from the group consisting of hydrogen, methyl, methoxy, bromo, fluoro, α'- or β'-phenyl, α'- or β'-pyridinyl, α'- or β'-furanyl, aminocarbonyl; and hydroxy;

$R_5$ is hydrogen;

$R_6$ is one to two substituents independently selected from the group consisting of hydrogen and methyl;

Y is O or S; and

Z is O or NH.

Another embodiment of the present invention is directed to compounds of Formula (I) and to compostions compsiring compounds of Formula (I) wherein:

G is —C(Z)N($R_1$)$R_2$, phenyl, or a heterocycle selected from the group consisting of tetrazolyl, oxadiazolyl, and pyridinyl, wherein the phenyl and the heterocycles of G are optionally substituted with one to three substituents independently selected from the group consisting of $C_{1-4}$alkanylcarbonylamino and oxo;

$R_1$ is selected from the group consisting of hydrogen and ethyl;

$R_2$ is selected from the group consisting of hydrogen and $C_{1-4}$alkanyl;

or $R_1$ and $R_2$ taken together with the nitrogen to which they are attached form a pyrrolidinyl ring optionally substituted with hydroxy;

$R_3$ is hydrogen, $C_{1-8}$alkanyl, $C_{2-8}$alkenyl, phenyl($C_{1-8}$)alkanyl, or heteroaryl($C_{1-8}$)alkanyl wherein the heteroaryl is imidazolyl, furanyl, pyridinyl, or thienyl;

$R_4$ is one substituent selected from the group consisting of hydrogen, methoxy, hydroxy, hydroxycarbonyl, and aminocarbonyl;

$R_5$ is hydrogen;

$R_6$ is hydrogen;

Y is O or S; and

Z is O.

Another embodiment of the present invention is directed to compounds of Formula (I) and to compostions compsiring compounds of Formula (I) wherein:

G is N,N-diethylaminocarbonyl, 2-methylcarbonylaminophenyl, N-N-diethylamidino, pyridin-3-yl, 3-(S)-hydroxypyrrolidin-1-ylcarbonyl, N-ethylaminocarbonyl, 1H-tetrazol-4-yl, pyridine-4-yl, 4H-[1,2,4]-oxadiazol-5-oxo-3-yl, N,N-dimethylaminocarbonyl, or pyrrolidin-1-ylcarbonyl;

$R_1$ is selected from the group consisting of hydrogen and ethyl;

$R_2$ is hydrogen or ethyl;

or $R_1$ and $R_2$ taken together with the nitrogen to which they are attached form a pyrrolidinyl ring optionally substituted with hydroxy;

$R_3$ is hydrogen, methyl, 3-methyl-2-butenyl, benzyl, phenethyl, or heteroarylmethyl wherein the heteroaryl is furanyl, imidazolyl, pyridinyl, or thienyl;

$R_4$ is one substituent and is hydrogen, methoxy, or hydroxyl;

$R_5$ is hydrogen;

$R_6$ is hydrogen;

Y is O or S; and

Z is O.

Still further embodiments of the invention relate to compounds of Formula (I) and to compositions containing compounds of Formula (I) that are:

10-(1-Benzyl-piperidin-4-yl)-6-hydroxy-10H-phenoxazine-3-carboxylic acid diethylamide;

10-(1-Benzylpiperidin-4-yl)-10H-phenoxazine-3,6-dicarboxylic acid 6-amide 3-diethylamide;

10-(1-Benzyl-piperidin-4-yl)-6-hydroxy-10H-phenoxazine-3-carboxylic acid dimethylamide;

3-[10-(1-Thiophen-2-ylmethyl-piperidin-4-yl)-10H-phenoxazin-3-yl]-4H-[1,2,4]oxadiazol-5-one;

10-(1-Pyridin-2-ylmethyl-piperidin-4-yl)-10H-phenoxazine-3-carboxylic acid diethylamide;

10-(1-Furan-3-ylmethyl-piperidin-4-yl)-3-(1H-tetrazol-5-yl)-10H-phenoxazine;

3-[10-(1-Pyridin-2-ylmethyl-piperidin-4-yl)-10H-phenoxazin-3-yl]-4H-[1,2,4]oxadiazol-5-one;

10-(1-Pyridin-2-ylmethyl-piperidin-4-yl)-3-(1H-tetrazol-5-yl)-10H-phenothiazine;

10-(1-Pyridin-3-ylmethyl-piperidin-4-yl)-10H-phenoxazine-3-carboxylic acid diethylamide;

N-[2-(6-Hydroxy-10-piperidin-4-yl-10H-phenoxazin-3-yl)-phenyl]-acetamide;

10-(1-Benzyl-piperidin-4-yl)-6-methoxy-10H-phenoxazine-3-carboxylic acid diethylamide;

10-Piperidin-4-yl-7-pyridin-3-yl-10H-phenoxazin-4-ol;

3-[10-(1-Furan-3-ylmethyl-piperidin-4-yl)-10H-phenoxazin-3-yl]-4H-[1,2,4]oxadiazol-5-one;

10-Piperidin-4-yl-10H-phenoxazine-3,6-dicarboxylic acid 6-amide 3-diethylamide;

N-[2-(10-Piperidin-4-yl-10H-phenothiazin-3-yl)-phenyl]-acetamide;
N-[2-(10-Piperidin-4-yl-10H-phenoxazin-3-yl)-phenyl]-acetamide;
10-(1-Benzyl-piperidin-4-yl)-7-bromo-10H-phenoxazine-4-carboxylic acid amide;
10-[1-(1H-Imidazol-2-ylmethyl)-piperidin-4-yl]-10H-phenoxazine-3-carboxylic acid diethylamide;
10-(1-Benzyl-piperidin-4-yl)-10H-phenoxazine-3-carboxylic acid diethylamide;
10-(1-Methyl-piperidin-4-yl)-10H-phenoxazine-3-carboxylic acid diethylamide;
10-[1-(3-Methyl-but-2-enyl)-piperidin-4-yl]-10H-phenoxazine-3-carboxylic acid diethylamide;
10-Piperidin-4-yl-3-pyridin-3-yl-10H-phenoxazine;
N,N-Diethyl-10-piperidin-4-yl-10H-phenoxazine-3-carboxamidine;
N-(2-{10-[1-(3-Methyl-but-2-enyl)-piperidin-4-yl]-10H-phenothiazin-3-yl}-phenyl)-acetamide;
[10-(1-Furan-3-ylmethyl-piperidin-4-yl)-10H-phenoxazin-3-yl]-(3-(S)-hydroxypyrrolidin-1-yl)-methanone;
(3-(S)-Hydroxypyrrolidin-1-yl)-[10-(1-pyridin-2-ylmethyl-piperidin-4-yl)-10H-phenoxazin-3-yl]-methanone;
10-Piperidin-4-yl-3-(1H-tetrazol-5-yl)-10H-phenoxazine;
10-(1-Benzyl-piperidin-4-yl)-7-bromo-10H-phenoxazine-4-carboxylic acid;
N-{2-[10-(1-Methyl-piperidin-4-yl)-10H-phenothiazin-3-yl]-phenyl}-acetamide;
10-(1-Pyridin-2-ylmethyl-piperidin-4-yl)-3-(1H-tetrazol-5-yl)-10H-phenoxazine;
(3-Hydroxypyrrolidin-1-yl)-[10-(1-pyridin-2-ylmethyl-piperidin-4-yl)-10H-phenothiazin-3-yl]-methanone;
N-(2-{10-[1-(1H-Imidazol-2-ylmethyl)-piperidin-4-yl]-10H-phenoxazin-3-yl}-phenyl)-acetamide;
N,N-Diethyl-10-(1-furan-3-ylmethyl-piperidin-4-yl)-10H-phenoxazine-3-carboxamidine;
N-{2-[10-(1-Pyridin-2-ylmethyl-piperidin-4-yl)-10H-phenothiazin-3-yl]-phenyl}-acetamide;
N,N-Diethyl-10-(1-pyridin-2-ylmethyl-piperidin-4-yl)-10H-phenoxazine-3-carboxamidine;
3-(10-Piperidin-4-yl-10H-phenoxazin-3-yl)-4H-[1,2,4]oxadiazol-5-one;
N,N-Diethyl-10-(1-phenethyl-piperidin-4-yl)-10H-phenoxazine-3-carboxamidine;
10-(1-Thiazol-2-ylmethyl-piperidin-4-yl)-10H-phenoxazine-3-carboxylic acid diethylamide;
10-(1-Methyl-piperidin-4-yl)-10H-phenoxazine-3-carboxylic acid diethylamide;
3-Pyridin-3-yl-10-(1-pyridin-2-ylmethyl-piperidin-4-yl)-10H-phenothiazine;
10-(1-Benzyl-piperidin-4-yl)-6-methoxy-10H-phenoxazine-3-carboxylic acid dimethylamide;
10-[1-(Imino-phenyl-methyl)-piperidin-4-yl]-10H-phenoxazine-3-carboxylic acid diethylamide;
N-{2-[10-(1-Benzyl-piperidin-4-yl)-10H-phenoxazin-3-yl]-phenyl}-acetamide;
3-[10-(1-Phenethyl-piperidin-4-yl)-10H-phenoxazin-3-yl]-4H-[1,2,4]oxadiazol-5-one;
10-Piperidin-4-yl-10H-phenoxazine-3-carbonitrile;
[10-(1-Benzyl-piperidin-4-yl)-10H-phenoxazin-3-yl]-(3-(S)-Hydroxypyrrolidin-1-yl)-methanone;
10-Piperidin-4-yl-3-pyridin-3-yl-10H-phenothiazine;
10-(1-Phenethyl-piperidin-4-yl)-3-(1H-tetrazol-5-yl)-10H-phenoxazine;
10-(1-Furan-3-ylmethyl-piperidin-4-yl)-3-pyridin-4-yl-10H-phenothiazine;
10-Piperidin-4-yl-7-pyridin-4-yl-10H-phenoxazin-4-ol;
10-Piperidin-4-yl-3-pyridin-4-yl-10H-phenoxazine;
N-{2-[10-(1-Thiophen-2-ylmethyl-piperidin-4-yl)-10H-phenothiazin-3-yl]-phenyl}-acetamide;
N-{2-[10-(1-Pyridin-2-ylmethyl-piperidin-4-yl)-10H-phenoxazin-3-yl]-phenyl}-acetamide;
6-Methoxy-10-piperidin-4-yl-3-pyridin-4-yl-10H-phenoxazine;
10-(1-Furan-3-ylmethyl-piperidin-4-yl)-10H-phenoxazine-3-carboxylic acid diethylamide;
10-[1-(1H-Imidazol-2-ylmethyl)-piperidin-4-yl]-3-(1H-tetrazol-5-yl)-10H-phenoxazine;
10-Piperidin-4-yl-10H-phenoxazine-3-carboxylic acid amide;
10-(1-Thiophen-2-ylmethyl-piperidin-4-yl)-10H-phenothiazine-3-carboxylic acid ethylamide;
N N-Diethyl-10-(1-methyl-piperidin-4-yl)-10H-phenothiazine-3-carboxamidine;
10-(1-Benzyl-piperidin-4-yl)-3-pyridin-3-yl-10H-phenoxazine;
10-(1-Methyl-piperidin-4-yl)-10H-phenoxazine-3-carboxylic acid methyl ester;
10-(1-Phenethyl-piperidin-4-yl)-10H-phenoxazine-3-carboxylic acid diethylamide;
10-(1-Methyl-piperidin-4-yl)-10H-phenoxazine-3-carboxylic acid;
10-(1-Methyl-piperidin-4-yl)-10H-phenothiazine-3-carboxylic acid ethylamide;
3-Pyridin-4-yl-10-(1-pyridin-2-ylmethyl-piperidin-4-yl)-10H-phenoxazine;
10-(1-Furan-3-ylmethyl-piperidin-4-yl)-3-pyridin-4-yl-10H-phenoxazine;
10-(1-Benzyl-piperidin-4-yl)-10H-phenoxazine-3-carboxylic acid;
(3-(S)-Hydroxypyrrolidin-1-yl)-(10-piperidin-4-yl-10H-phenoxazin-3-yl)-methanone;
N-{2-[10-(1-Thiophen-2-ylmethyl-piperidin-4-yl)-10H-phenoxazin-3-yl]-phenyl}-acetamide;
3-Bromo-10-piperidin-4-yl-10H-phenothiazine;
[10-(1-Methyl-piperidin-4-yl)-10H-phenothiazin-3-yl]-pyrrolidin-1-yl-methanone;
3-Bromo-10-(1-phenethyl-piperidin-4-yl)-10H-phenothiazine;
10-(1-Benzyl-piperidin-4-yl)-3-chloro-10H-phenoxazine;
10-Piperidin-4-yl-10H-phenothiazine-3-carbonitrile;
10-(1-Thiophen-2-ylmethyl-piperidin-4-yl)-10H-phenoxazine-3-carboxylic acid diethylamide;
3-Chloro-6-methoxy-10-piperidin-4-yl-10H-phenoxazine;
10-(1-Phenethyl-piperidin-4-yl)-3-pyridin-4-yl-10H-phenothiazine;
10-(1-Benzyl-piperidin-4-yl)-3-pyridin-4-yl-10H-phenoxazine;
10-(1-Phenethyl-piperidin-4-yl)-3-pyridin-4-yl-10H-phenoxazine;
10-Piperidin-4-yl-3-(1H-tetrazol-5-yl)-10H-phenothiazine;
N-{2-[10-(1-Furan-3-ylmethyl-piperidin-4-yl)-10H-phenoxazin-3-yl]-phenyl}-acetamide;
10-(1-Methyl-piperidin-4-yl)-10H-phenoxazine-3-carboxylic acid;
(3-(S)-Hydroxypyrrolidin-1-yl)-[10-(1-methyl-piperidin-4-yl)-10H-phenoxazin-3-yl]-methanone;
(3-Hydroxypyrrolidin-1-yl)-[10-(1-methylpiperidin-4-yl)-10H-phenothiazin-3-yl]-methanone;
(3-(S)-Hydroxypyrrolidin-1-yl)-[10-(1-phenethyl-piperidin-4-yl)-10H-phenoxazin-3-yl]-methanone;
(3-Hydroxypyrrolidin-1-yl)-[10-(1-phenethyl-piperidin-4-yl)-10H-phenothiazin-3-yl]-methanone;

3-Pyridin-4-yl-10-(1-thiophen-2-ylmethyl-piperidin-4-yl)-10H-phenoxazine;
10-(1-Methyl-piperidin-4-yl)-3-(1H-tetrazol-5-yl)-10H-phenothiazine;
3-Bromo-10-(1-methylpiperidin-4-yl)-10H-phenothiazine;
3-Pyridin-3-yl-10-(1-thiophen-2-ylmethyl-piperidin-4-yl)-10H-phenoxazine;
N-{2-[10-(1-Phenethyl-piperidin-4-yl)-10H-phenoxazin-3-yl]-phenyl}-acetamide;
10-(1-Methyl-piperidin-4-yl)-10H-phenothiazine-3-carbonitrile;
10-(1-Benzylpiperidin-4-yl)-7-diethylcarbamoyl-10H-phenoxazine-4-carboxylic acid;
10-(1-Phenethyl-piperidin-4-yl)-3-pyridin-3-yl-10H-phenoxazine;
3-Pyridin-3-yl-10-(1-pyridin-2-ylmethyl-piperidin-4-yl)-10H-phenoxazine;
10-(1-Furan-3-ylmethyl-piperidin-4-yl)-3-pyridin-3-yl-10H-phenoxazine;
7-Chloro-10-piperidin-4-yl-10H-phenoxazin-4-ol; or
10-(1-Benzoyl-piperidin-4-yl)-10H-phenoxazine-3-carboxylic acid diethylamide.

Another embodiment of the present invention is directed to a compound of Formula (I) wherein $R_4$ is preferably substituted at the $\alpha'$- or $\beta'$-position of Formula (I).

Another embodiment of the present invention is a composition comprising the dextrorotatory enantiomer of a compound of formula (I), wherein said composition is substantially free from the levorotatory isomer of said compound. In the present context, substantially free means less than 25%, preferably less than 10%, more preferably less than 5%, even more preferably less than 2% and even more preferably less than 1% of the levorotatory isomer calculated as.

$$\% \text{ levorotatory} = \frac{(\text{mass levorotatory})}{(\text{mass dextrorotatory}) + (\text{mass levorotatory})} \times 100$$

Another embodiment of the present invention is a composition comprising the levorotatory enantiomer of a compound of formula (I) wherein said composition is substantially free from the dextrorotatory isomer of said compound. In the present context, substantially free from means less than 25%, preferably less than 10%, more preferably less than 5%, even more preferably less than 2% and even more preferably less than 1% of the dextrorotatory isomer calculated as $$\% \text{ dextrorotatory} = \frac{(\text{mass dextrorotatory})}{(\text{mass dextrorotatory}) + (\text{mass levorotatory})} \times 100$$

The compounds of the present invention may also be present in the form of pharmaceutically acceptable salts. For use in medicine, the salts of the compounds of this invention refer to non-toxic "pharmaceutically acceptable salts" (Ref. International J. Pharm., 1986, 33, 201-217; J. Pharm. Sci., 1997 (January), 66, 1, 1). Other salts well known to those in the art may, however, be useful in the preparation of compounds according to this invention or of their pharmaceutically acceptable salts. Representative organic or inorganic acids include, but are not limited to, hydrochloric, hydrobromic, hydriodic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benzenesulfonic, oxalic, pamoic, 2-naphthalenesulfonic, p-toluenesulfonic, cyclohexanesulfamic, salicylic, saccharinic or trifluoroacetic acid. Representative organic or inorganic bases include, but are not limited to, basic or cationic salts such as benzathine, chloroprocaine, choline, diethanolamine, ethylenediamine, meglumine, procaine, aluminum, calcium, lithium, magnesium, potassium, sodium and zinc.

The present invention includes within its scope prodrugs of the compounds of this invention. In general, such prodrugs will be functional derivatives of the compounds that are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs", ed. H. Bundgaard, Elsevier, 1985.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-d-tartaric acid and/or (+)-di-p-toluoyl-l-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

Even though the compounds of the present invention (including their pharmaceutically, acceptable salts and pharmaceutically acceptable solvates) can be administered alone, they will generally be administered in admixture with a pharmaceutical carrier, excipient or diluent selected with regard to the intended route of administration and standard pharmaceutical or veterinary practice. Thus, the present invention is directed to pharmaceutical and veterinary compositions comprising compounds of Formula (I) and one or more pharmaceutically acceptable carriers, excipients or diluents.

By way of example, in the pharmaceutical and veterinary compositions of the present invention, the compounds of the present invention may be admixed with any suitable binder(s), lubricant(s), suspending agent(s), coating agent(s), and/or solubilising agent(s).

Tablets or capsules of the compounds may be administered singly or two or more at a time, as appropriate. It is also possible to administer the compounds in sustained release formulations.

Alternatively, the compounds of the general Formula (I) can be administered by inhalation or in the form of a suppository or pessary, or they may be applied topically in the form of a lotion, solution, cream, ointment or dusting powder. An alternative means of transdermal administration is by use of a skin patch. For example, they can be incorporated into a cream consisting of an aqueous emulsion of polyethylene glycols or liquid paraffin. They can also be incorporated, at a concentration of between 1 and 10% by weight, into an ointment consisting of a white wax or white soft paraffin base together with such stabilizers and preservatives as may be required.

For some applications, preferably the compositions are administered orally in the form of tablets containing excipients such as starch or lactose, or in capsules or ovules either alone or in admixture with excipients, or in the form of elixirs, solutions or suspensions containing flavoring or coloring agents.

The compositions (as well as the compounds alone) can also be injected parenterally, for example intracavernosally, intravenously, intramuscularly or subcutaneously. In this case, the compositions will comprise a suitable carrier or diluent.

For parenteral administration, the compositions are best used in the form of a sterile aqueous solution which may contain other substances, for example enough salts or monosaccharides to make the solution isotonic with blood.

For buccal or sublingual administration the compositions may be administered in the form of tablets or lozenges which can be formulated in a conventional manner.

By way of further example, pharmaceutical and veterinary compositions containing one or more of the compounds of the invention described herein as the active ingredient can be prepared by intimately mixing the compound or compounds with a pharmaceutical carrier according to conventional pharmaceutical compounding techniques. The carrier may take a wide variety of forms depending upon the desired route of administration (e.g., oral, parenteral). Thus for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Solid oral preparations may also be coated with substances such as sugars or be enteric-coated so as to modulate the major site of absorption. For parenteral administration, the carrier will usually consist of sterile water and other ingredients may be added to increase solubility or preservation. Injectable suspensions or solutions may also be prepared utilizing aqueous carriers along with appropriate additives.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those skilled in that art. To be administered in the form of a transdermal delivery system, the dosage administration will, of course, be continuous rather than intermittent throughout the dosage regimen.

It is also apparent to one skilled in the art that the therapeutically effective dose for active compounds of the invention or a pharmaceutical composition thereof will vary according to the desired effect. Therefore, optimal dosages to be administered may be readily determined and will vary with the particular compound used, the mode of administration, the strength of the preparation, and the advancement of the disease condition. In addition, factors associated with the particular subject being treated, including subject age, weight, diet and time of administration, will result in the need to adjust the dose to an appropriate therapeutic level. The above dosages are thus exemplary of the average case. There can, of course, be individual instances where higher or lower dosage ranges are merited, and such are within the scope of this invention.

Compounds of this invention may be administered in any of the foregoing compositions and dosage regimens or by means of those compositions and dosage regimens established in the art whenever use of the compounds of the invention as analgesics is required for a subject in need thereof.

The invention also provides a pharmaceutical or veterinary pack or kit comprising one or more containers filled with one or more of the ingredients of the pharmaceutical and veterinary compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

The compounds of the present invention may be used to treat mild to severe pain in warm-blooded animals such as humans by administration of an analgesically effective dose. The dosage range would be from about 0.1 mg to about 15,000 mg, in particular from about 50 mg to about 3500 mg or, more particularly from about 100 mg to about 1000 mg of active ingredient in a regimen of about 1 to 4 times per day for an average (70 kg) human; although, it is apparent to one skilled in the art that the therapeutically effective amount for active compounds of the invention will vary as will the types of pain being treated.

For oral administration, a pharmaceutical composition is preferably provided in the form of tablets containing 0.01, 10.0, 50.0, 100, 150, 200, 250, and 500 milligrams of the active ingredient for the symptomatic adjustment of the dosage to the subject to be treated.

Examples of pain intended to be within the scope of the present invention include, but are not limited to, inflammatory pain, centrally mediated pain, peripherally mediated pain, visceral pain, structural or soft tissue injury related pain, progressive disease related pain, neuropathic pain and acute pain such as caused by acute injury, trauma or surgery and chronic pain such as headache and that caused by neuropathic conditions, post-stroke conditions, cancer, and migraine.

Compounds of the present invention are also useful as immunosuppressants, antiinflammatory agents, agents for the treatment and prevention of neurological and psychiatric conditions, for instance, depression and Parkinson's disease, agents for the treatment of urological and reproductive conditions, for instance, urinary incontinence and premature ejaculation, medicaments for drug and alcohol abuse, agents for treating gastritis and diarrhea, cardiovascular agents and cardioprotective agents and agents for the treatment of respiratory diseases.

The compounds of the present invention are also useful in treating pain caused by osteoarthritis, rheumatoid arthritis, fibromyalgia, migraine, headache, toothache, burn, sunburn, snake bite (in particular, venomous snake bite), spider bite, insect sting, neurogenic bladder, benign prostatic hypertrophy, interstitial cystitis, rhinitis, contact dermatitis/hypersensitivity, itch, eczema, pharyngitis, mucositis, enteritis, cellulites, causalgia, sciatic neuritis, mandibular joint neuralgia, peripheral neuritis, polyneuritis, stump pain, phantom limb pain, post-operative ileus, cholecystitis, postmastectomy pain syndrome, oral neuropathic pain, Charcot's pain, reflex sympathetic dystrophy, Guillain-Barre syndrome, meralgia paresthetica, burning-mouth syndrome, post-herpetic neuralgia, trigeminal neuralgia, cluster headache, migraine headache, peripheral neuropathy, bilateral peripheral neuropathy, diabetic neuropathy, postherpetic neuralgia, trigeminal neuralgia, optic neuritis, postfebrile neuritis, migrating neuritis, segmental neuritis, Gombault's neuritis, neuronitis, cervicobrachial neuralgia, cranial neuralgia, geniculate neuralgia, glossopharyngial neuralgia, migrainous neuralgia, idiopathic neuralgia, intercostals neuralgia, mammary neuralgia, Morton's neuralgia, nasociliary neuralgia, occipital neuralgia, red neuralgia, Sluder's neuralgia, splenopalatine neuralgia, supraorbital neuralgia, vidian neuralgia, inflammatory bowel disease, irritable bowel syndrome, sinus headache, tension headache, labor, childbirth, menstrual cramps, and cancer.

In regard to the use of the present compounds in treatment of the disases or conditions such as those listed above, a therapeutically effective dose can be determined by persons skilled in the art by the use of established animal models. Such a dose would likely fall in the range of from about 0.01 mg to about 15,000 mg of active ingredient administered 1 to 4 times per day for an average (70 kg) human.

General Synthetic Methods

Representative compounds of the present invention can be synthesized in accordance with the general synthetic methods described below and are illustrated in the schemes that follow. Since the schemes are an illustration, the invention should not be construed as being limited by the chemical reactions and conditions expressed. The preparation of the various starting materials used in the schemes is well within the skill of persons versed in the art.

Scheme 1

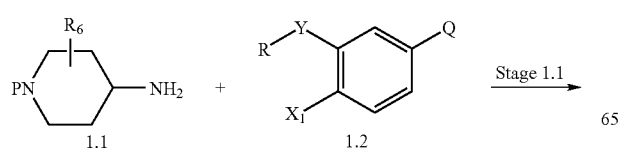

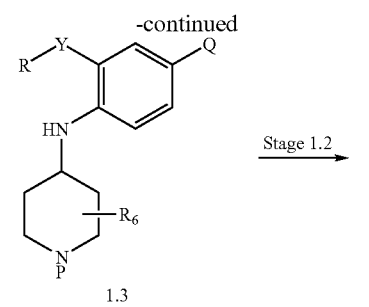

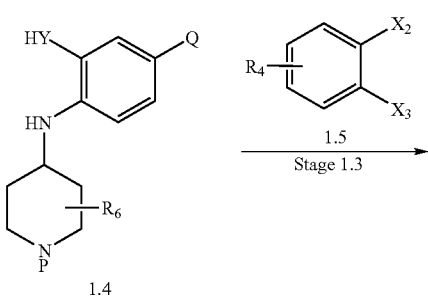

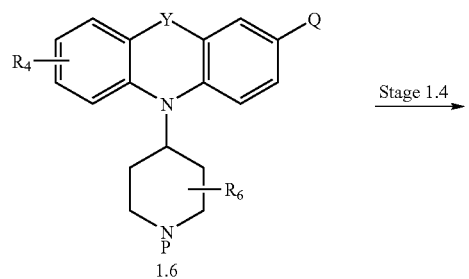

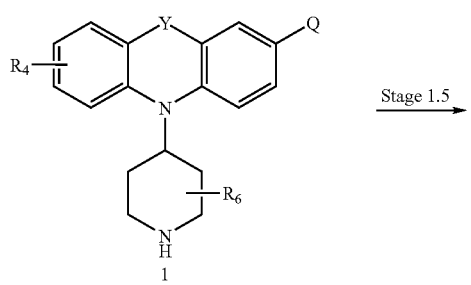

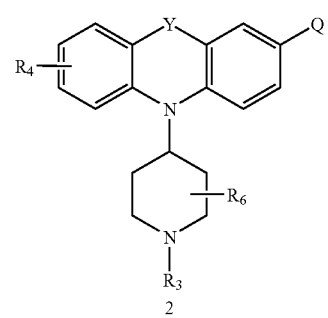

The preparation of compounds of this invention is illustrated in Schemes 1 through 11. The overall strategy in Scheme 1 is based on the synthesis of appropriately substituted compounds of formula 1.4 (Y=O, S) that are condensed with an appropriately substituted compound of formula 1.5. In compounds of formula 1.5, $X_2$ and $X_3$ can each be a halogen atom, trifluoromethanesulfonyloxy or a nitro group. In stage 1.1, an appropriately substituted N1-protected 4-aminopiperidine 1.1 is condensed with an appropriately substituted O-protected phenol (Y=O) or thiophenol (Y=S) 1.2. The protection group on the N1 nitrogen of 1.1 (represented as P) may include an alkanyl, alkenyl or aralkanyl group in which case they are the therapeutically useful products of this invention. The group P may also be trifluoromethylcarbonyl, alkoxycarbonyl or aralkoxycarbonyl. Useful phenol or thiophenol protection groups (R) include lower alkyl groups, benzyl, trialkylsilyl and the like. Appropriate substituents on the protected phenol or thiophenol in the 2-position ($X_1$) may include halogens and trifluoromethanesulfonyloxy. The Q group in the 5-position may be a substituent such as fluoro, chloro, bromo, cyano, iodo, carboxy, or trifluoromethanesulfonyloxy. Stage 1.2 includes removal of the phenol or thiophenol protective group. Such transformations may include the dealkylation of lower alkyl ethers to give their corresponding alcohols using reagents such as boron trihalides, or dealkylation of lower alkyl thioethers using reagents such as Na/NH$_3$. A benzyl protective group may be removed under conditions of hydrogenation in the presence of a transition metal such as palladium. Trialkylsilyl protective groups may be removed by treatment with a source of fluoride anion such as tetrabutyl ammonium fluoride, or by exposure to an inorganic acid such as aqueous hydrogen chloride and the like.

In stage 1.3, hydroxyaniline (Y=O) or thioaniline (Y=S) 1.4 may be condensed with an appropriately substituted benzene moiety 1.5. Substituents $X_2$ and $X_3$ may include halogens, trifluoromethanesulfonyloxy, or a nitro group. Useful coupling conditions of the anilino nitrogen with a compound of formula 1.5 include palladium catalyzed condensations in the presence of a phosphine ligand such as Pd$_2$(dba)$_3$ and a base such as cesium carbonate. Coupling of the hydroxy or thio moiety with the remaining substituted phenyl group may proceed using Ullmann type coupling conditions. In addition, the two steps described in stage 1.3 may be reversed with biaryl ether or biaryl thioether formation preceding the formation of the biaryl amine. Alternatively, the condensation between compounds of formula 1.4 and compounds of formula 1.5 to yield compounds of formula 1.6 in one step may be affected by treatment with an inorganic base such as potassium carbonate in a suitable solvent such as dimethyl formamide.

The regiochemical outcome of the condensation between compounds of formula 1.4 and compounds of formula 1.5 depends on the position of the R4 substituent in compounds of formula 1.5 and on the reaction conditions used for the condensation. An extensive review on this topic is available in the literature (see, for eample: 'The Smiles and Related Rearrangements of aromatic Systems' by W. E. Truce, E. M. Kreider, and W. W. Brand in Organic Reactions, 1970, Vol. 18, pp. 99-215).

The protective group P can be removed to obtain secondary amines 1 as illustrated in Stage 1.4. These transformations may be carried out using certain acidic reagents such as hydrogen bromide or trimethylsilyl iodide. Phenoxazines (Y=O) or phenothiazines (Y=S) of type 1.6 bearing readily cleavable groups such as methyl, allyl or benzyl may be transformed into the aforementioned alkoxycarbonyl derivatives by treatment with alkanylchloroformates such as ethyl chloroformate or 1-chloroethyl chloroformate and thus serve as sources of phenoxazines and phenothiazines 1. Phenoxazines or phenothiazines of type 1.6 bearing a trifluoromethylcarbonyl group may be treated with potassium carbonate in an alcoholic solvent such as methanol to yield phenoxazines and phenothiazines 1.

Finally the secondary amines 1 may be converted to a compound of formula 2 as shown in Stage 1.5. These transformations may be carried out by reductive alkylation using a carbonyl compound and a reducing agent such as sodium borohydride, sodium cyanoborohydride, sodium triacetoxyborohydride, or tetramethylammonium triacetoxyborohydride. They may also be carried out by alkylation using an alkanyl, alkenyl or aralkyl halide and an organic or inorganic base.

The Q function in compounds 1 or 2 may be converted into group G, which may be —C(Z)NR$_1$R$_2$, an aryl substituent, or an appropriate heterocycle as defined herein, to give compounds of formula I. When the Q function is a halogen or trifluoromethanesulfonyloxy, it may be converted to an ester via alkoxycarbonylation using carbon monoxide, an aliphatic alcohol, a trialkanyl amine, and a palladium catalyst such as bis(triphenylphosphine) palladium(II)dichloride. Subsequently, when Q is an ester, the ester may be hydrolyzed to a carboxylic acid. The carboxylic acid may then be coupled with ammonia, a primary amine, or a secondary amine to form a primary, secondary or tertiary amide, respectively. Alternatively, the conversion of a carboxylic acid to an amide may be carried out via an acid chloride using thionyl chloride, oxalyl chloride, or the like, followed by a Schotten-Baumann reaction using ammonia or an amine in the presence of an alkali metal hydroxide. Alternatively, the conversion of a carboxylic acid to an amide may be carried out via the use of peptide coupling agents such as 1,3-dicyclohexylcarbondiimide (DCC), O-(7-azabenzotriazol-1-yl)-N,N,N',N'-tetramethyluronium hexafluorophosphate (HATU), O-benzotriazol-1-yl-N,N,N',N'-tetramethyluronium hexafluorophosphate (HBTU), or the like. Alternatively, the ester may be converted directly to the amide by the action of a dimethylaluminum amide.

Alternatively, when the Q function is a halogen or trifluoromethanesulfonyloxy, it may be converted directly to an amide via aminocarbonylation using a carbon monoxide source such as molybdenum hexacarbonyl, an appropriate amine, and a palladium catalyst such as Hermann's catalyst.

Alternatively, one may effect the transformation of the group Q to a substituent G (wherein G is an amidino or heterocycle) by way of a nitrile. Synthesis of the nitrile may be accomplished by treatment of the compounds 1 or 2 (when Q is bromo or trifluoromethanesulfonyloxy) with Zn(CN)$_2$ and a palladium catalyst such as (Ph$_3$P)$_4$Pd or by treatment of the compounds 1 or 2 with CuCN at elevated temperatures. For the synthesis of amidino functional groups, the nitrile is treated with hydroxylamine under basic conditions to afford an oxime. Treatment of the oxime with a primary or secondary amine, CuCl, and an alkali metal carbonate under microwave irradiation in an alcoholic solvent provides the amidino compounds of the present invention. Microwave accelerated reactions may be performed using either a CEM Discover or a Personal Chemistry Smith Synthesizer microwave instrument. The oxime described above is instrumental in the preparation of compounds wherein G is a heterocycle. The oxime may be cyclized with a variety of electrophiles known to one versed in the art to give the heterocycles of the present invention. For instance, reaction of an oxime with CDI provides oxadiazolones, and treatment of the oxime with TCDI provides the corresponding oxadiazolethiones. Similarly, the treatment of the oxime with thionyl chloride in the presence of a tertiary amine gives oxathiadiazoles of the present invention.

Alternatively, compounds where Q is a halogen atom or a trifluoromethanesulfonyloxy group may participate in transition metal-mediated coupling reactions such as Suzuki, Stille or Negishi chemistry.

Desired end products of the present invention may include chemical modifications at $R_4$. Such transformations may include the dealkylation of lower alkyl ethers to give the corresponding alcohols using reagents such as boron trihalides. Compounds where $R_4$ is a halogen atom may participate in transition metal-mediated coupling reactions such as Suzuki, Stille or Negishi chemistry.

this scheme, an appropriately substituted phenol (Y=O) or thiophenol (Y=S) of type 2.2 is reacted with an appropriately substituted benzene moiety 2.1 in the presence of a base, such as potassium carbonate or sodium hydroxide in an organic solvent, such as dimethyl formamide, dimethyl acetamide, dimethyl sulfoxide or the like as shown in stage 2.1. Appropriate substituents $X_1$ and $X_2$ in this scheme may include halogens and trifluoromethanesulfonyloxy. In stage 2.2, the nitro functionality is reduced to the corresponding amine. This reduction can be accomplished via treatment with tin(II) chloride in an alcoholic solvent such as ethanol. Stage 2.3 depicts the conversion of primary aniline 2.4 to secondary aniline 2.6, which can be accomplished via reductive alkylation using a carbonyl compound 2.5 and a reducing agent such as sodium borohydride, sodium cyanoborohydride, sodium triacetoxyborohydride, or tetramethylammonium triacetoxyborohydride. Stage 2.4 depicts formation of compounds of formula 1.6, which can be accomplished by treatment of secondary aniline 2.6 with an appropriate base such as potassium carbonate.

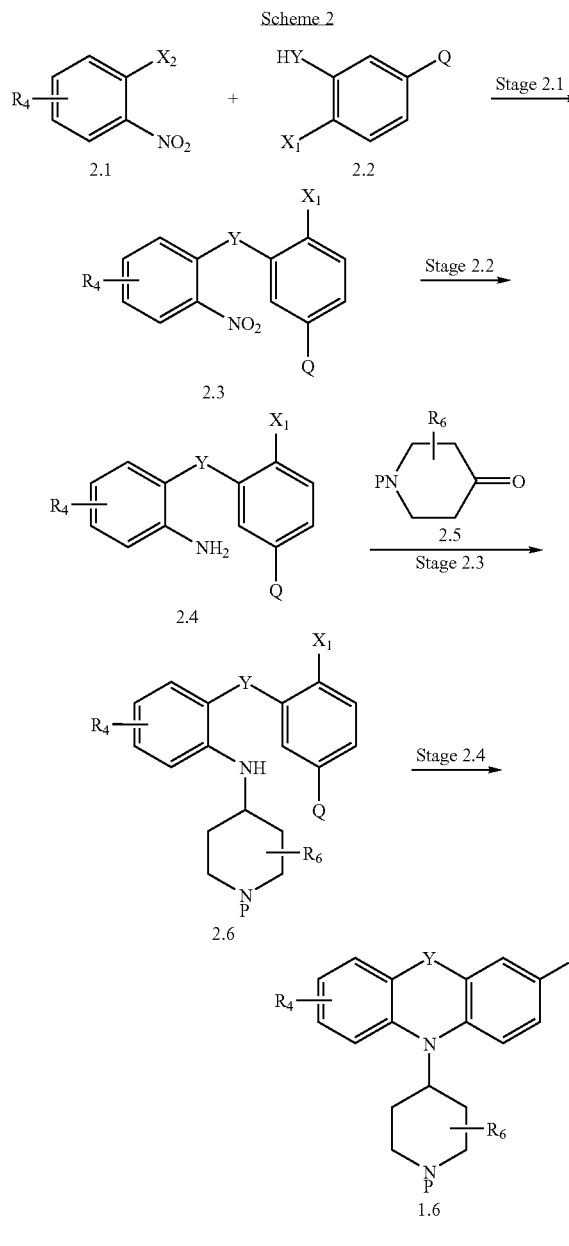

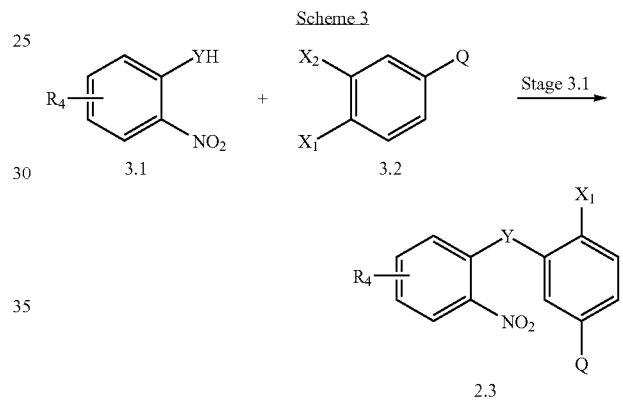

Scheme 3 illustrates an alternative synthesis of compound 2.3. In this approach, an appropriately substituted 2-nitrophenol (Y=O) or 2-nitrothiophenol (Y=S) may be condensed with an appropriately substituted benzene moiety of type 3.2 under Ullmann type coupling conditions. Appropriate substituents $X_1$ and $X_2$ include halogens and trifluoromethanesulfonyloxy.

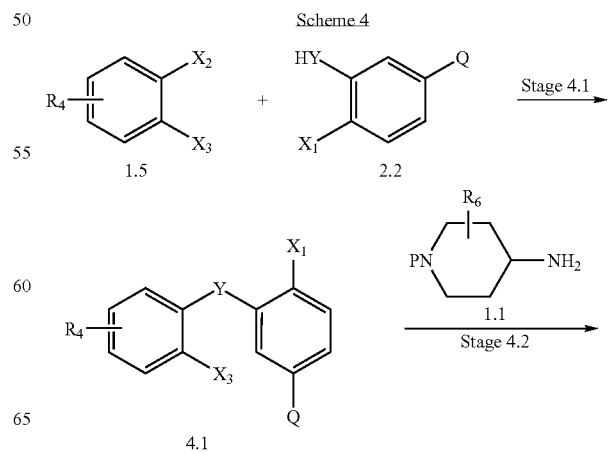

Scheme 2 outlines an alternative approach to the synthesis of phenoxazines (Y=O) or phenothiazines (Y=S) 1.6. In -continued

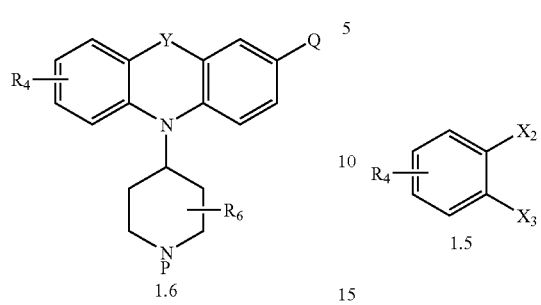

Scheme 4 illustrates an alternative approach to the synthesis of phenoxazines (Y=O) or phenothiazines (Y=S) 1.6. Condensation of appropriately substituted phenols (Y=O) or thiophenols (Y=S) 2.2 with an appropriately substituted benzene moiety 1.5 under Ullmann type coupling conditions as shown in stage 4.1 may result in the formation of biaryl ethers (Y=O) or biaryl thioethers (Y=S) 4.1. Appropriate $X_1$, $X_2$ and $X_3$ substituents may include halogens and trifluoromethanesulfonyloxy. Palladium catalyzed condensation of biaryl ethers or biaryl thioethers 4.1 with appropriately substituted N1-protected 4-aminopiperidines 1.1 in the presence of a phosphine ligand such as $Pd_2(dba)_3$ and a base such as cesium carbonate as shown in stage 4.2 may result in the formation of phenoxazines or phenothiazines 1.6.

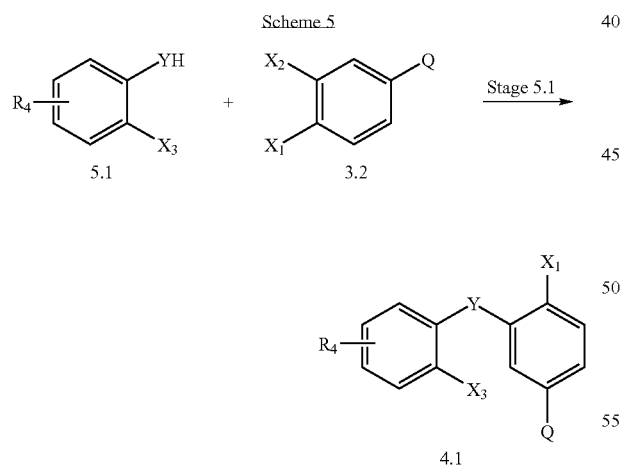

An alternative approach to the synthesis of intermediate 4.1 is depicted in Scheme 5 and is based on the reaction of appropriately substituted phenols (Y=O) or thiophenols (Y=S) 5.1 with an appropriately substituted benzene moiety 3.2 under Ullmann type coupling conditions (stage 5.1). Substituents $X_1$, $X_2$, and $X_3$ may include halogens or trifluoromethanesulfonyloxy.

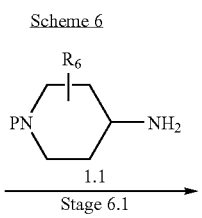

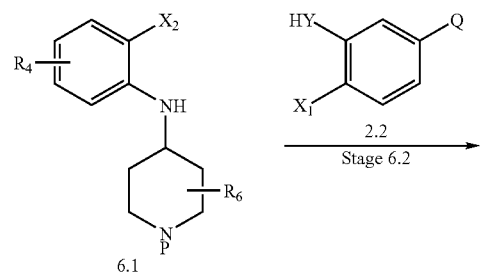

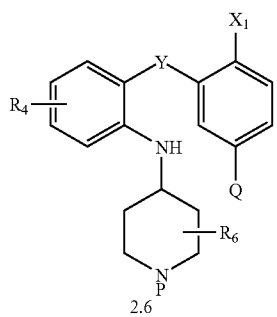

Scheme 6 illustrates an alternative approach to the synthesis of intermediates 2.6. An appropriately substituted compound of formula 1.5 may be reacted with $R_6$-substituted N1-protected 4-aminopiperidines 1.1 in the presence of a palladium catalyst such as $Pd_2(dba)_3$, a phosphine ligand and a base such as cesium carbonate as shown in stage 6.1. Appropriate $X_1$ and $X_2$ substituents may include halogens and trifluoromethanesulfonyloxy. Compounds of formula 6.1 may then be reacted with appropriately substituted phenols (Y=O) or thiophenols (Y=S) 2.2 under Ullmann type coupling conditions to yield anilines 2.6 as shown in stage 6.2.

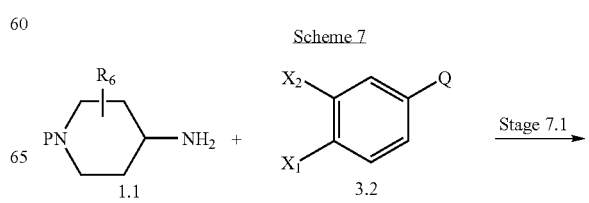

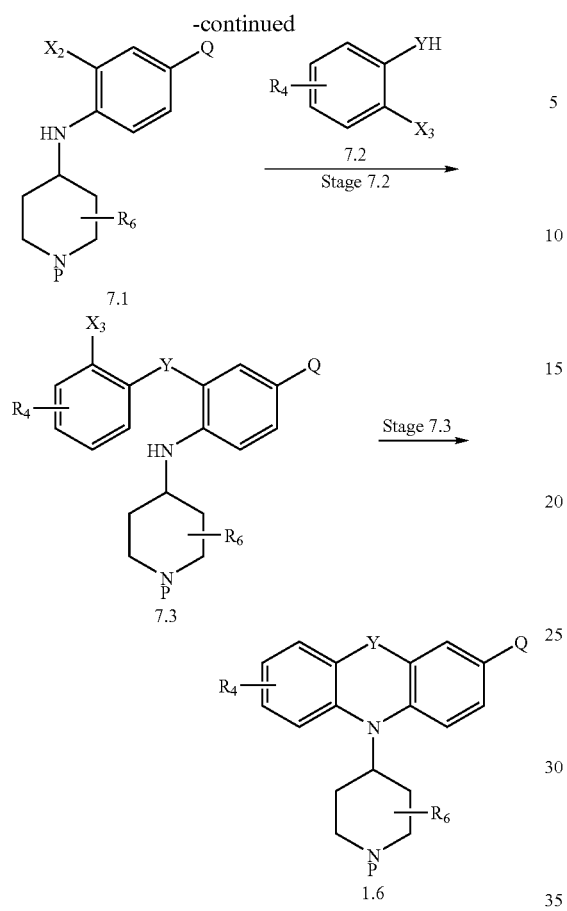

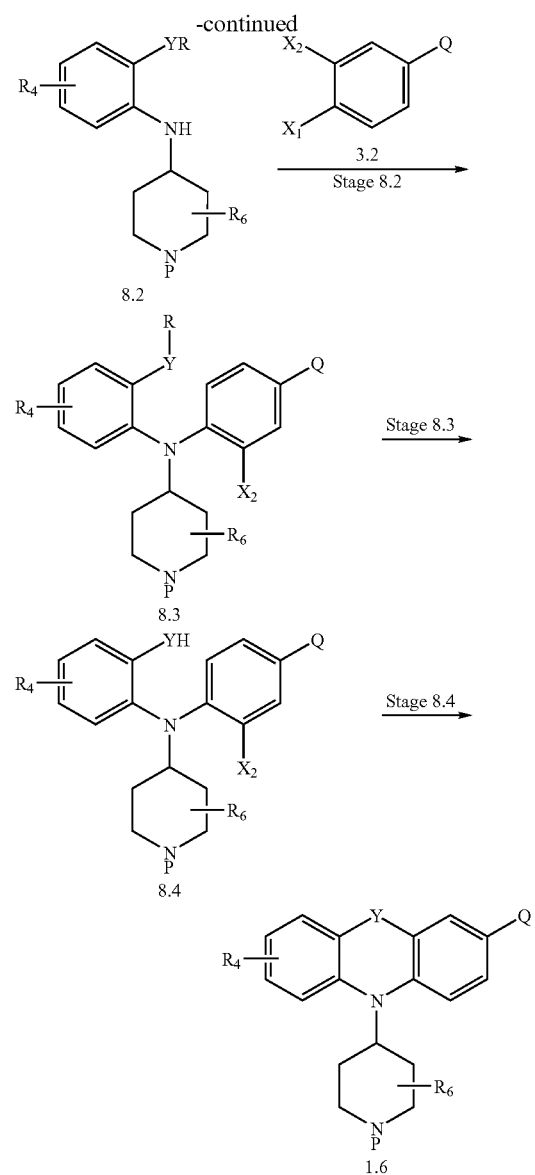

Scheme 7 illustrates an alternative approach to the synthesis of phenoxazines (Y=O) or phenothiazines (Y=S) 1.6. Condensation of appropriately substituted compounds of formula 3.2 with $R_6$-substituted N1-protected 4-aminopiperidines 1.1 may result in formation of intermediate 7.1 as shown in stage 7.1. Appropriate $X_1$, $X_2$, and $X_3$ substituents may include halogens and trifluoromethanesulfonyloxy. Reaction of compounds 7.1 with appropriately substituted phenols (Y=O) or thiophenols (Y=S) 7.2 under Ullmann like coupling conditions may result in formation of compounds 7.3 as shown in stage 7.2. Finally, ring closure of compounds 7.3 may be accomplished in the presence of a palladium catalyst such as $Pd_2(dba)_3$, a phosphine ligand such as 4,5-bis(diphenylphosphino)-9,9-dimethylxanthene (xant phos) and a base such as potassium tert-butoxide or cesium carbonate as shown in stage 7.3.

Scheme 8

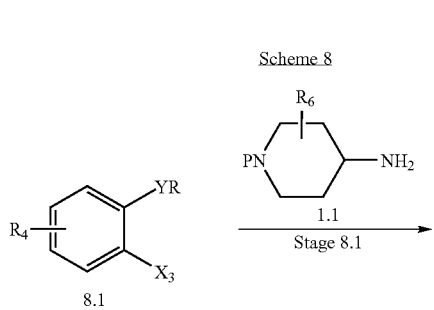

Scheme 8 illustrates an alternative synthesis of phenoxazines (Y=O) or phenothiazines (Y=S) 1.6 and is based on an Ullmann-like coupling of $R_6$-substituted N1-protected 4-aminopiperidines 1.1 with appropriately substituted and protected phenols (Y=O) or thiophenols (Y=S) 8.1 as shown in stage 8.1. Useful phenol or thiophenol protective groups for compounds 8.1 include lower alkyl groups, benzyl, trialkylsilyl and the like. Appropriate $X_1$, $X_2$, and $X_3$ substituents may include halogens and trifluoromethanesulfonyloxy. The resulting compounds 8.2 may be condensed with appropriately functionalized benzene compounds 3.2 to yield diarylanilines 8.3. Stage 8.3 includes deprotection of the phenol or thiophenol protective group. Such transformations may include the dealkylation of lower alkyl ethers to give their corresponding alcohols using reagents such as boron trihalides or the dealkylation of the alkyl thioethers using $Na/NH_3$. A benzyl protective group may be removed under conditions of hydrogenation in the presence of a transition metal such as palladium. Trialkylsilyl protective groups may be removed by treatment with a source of fluoride anion such as tetrabutyl ammonium fluoride, or by exposure to an inorganic acid such as aqueous hydrogen chloride and the like. Finally, ring closure of compounds 8.3 to phenoxazines or phenothiazines 1.6 may be accomplished via an Ullmann type transformation as shown in stage 8.4.

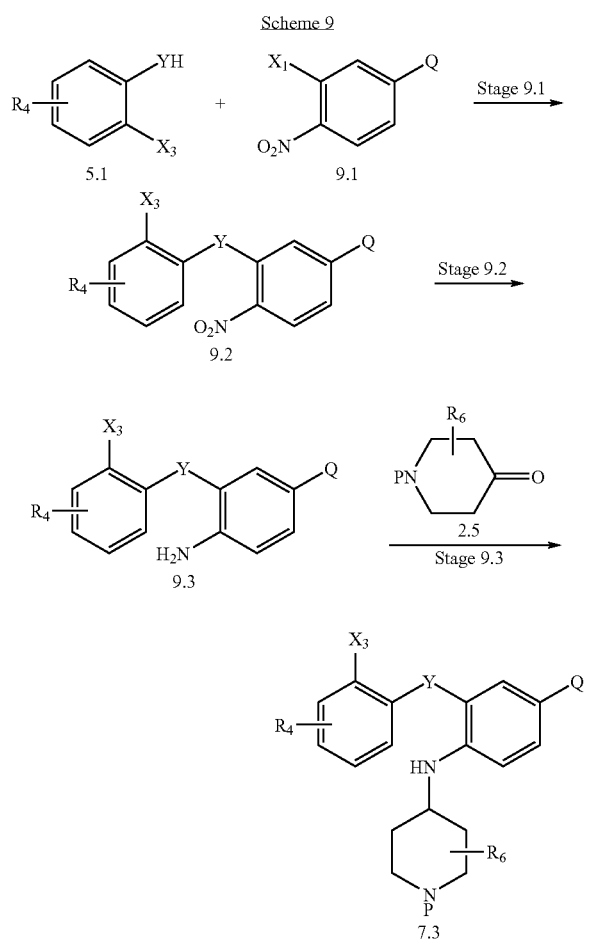

Scheme 9 illustrates another synthetic approach to compounds of formula 7.4. Displacement of $X_1$ in appropriately substituted compounds of formula 9.1 with appropriately substituted compounds of formula 5.1 as shown in stage 9.1 may lead to biaryl ethers (Y=O) and biarylthioethers (Y=S) of formula 9.2. Appropriate $X_1$ and $X_3$ substituents may include halogens and trifluoromethanesulfonyloxy. Reduction of compounds of formula 9.2 to amines of formula 9.3 as shown in stage 9.2 may be accomplished using tin(II) chloride in an alcoholic solvent such as ethanol. Stage 9.3 depicts the conversion of primary anilines 9.3 to secondary anilines of formula 7.4 and can be accomplished via reductive alkylation using a carbonyl compound of formula 2.5 and a reducing agent such as sodium borohydride, sodium cyanoborohydride, sodium triacetoxyborohydride, or tetramethylammonium triacetoxyborohydride.

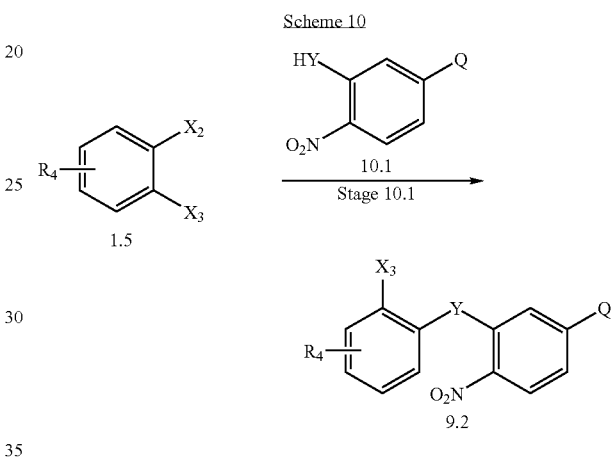

Scheme 10 illustrates another synthetic approach to compounds of formula 9.2. For construction of diaryl ethers (Y=O) and diaryl thioethers (Y=S) of formula 9.2, appropriately substituted 2-hydroxynitrobenzenes or 2-thionitrobenzenes of formula 10.1 may be caused to react with appropriately substituted compounds of formula 1.5 under Ullmann type conditions as shown in stage 10.1. Appropriate $X_2$ and $X_3$ substituents may include halogens and trifluoromethanesulfonyloxy.

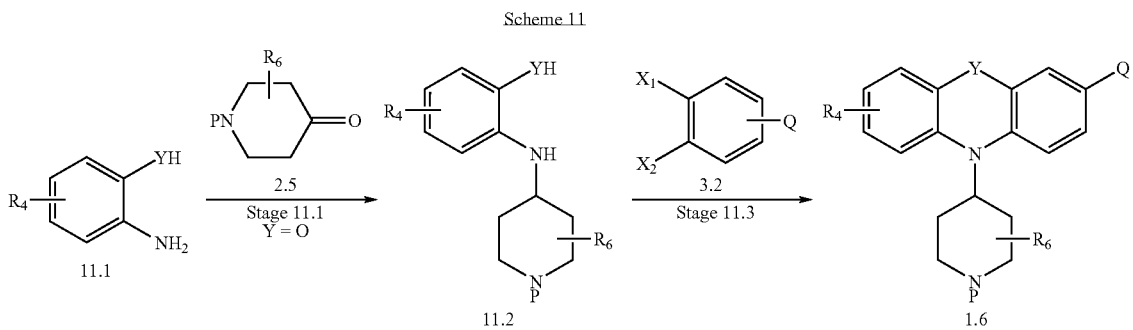

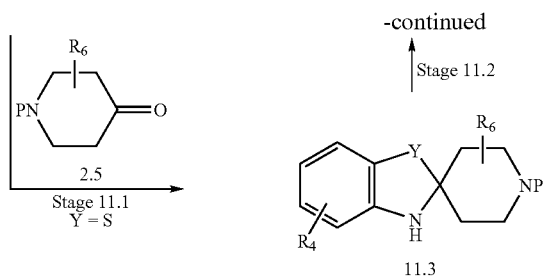

Scheme 11 illustrates another synthetic approach to compounds of formula 1.6. Stage 11.1 depicts the conversion of appropriately substituted 2-hydroxyanilines (Y=O) or 2-thioanilines (Y=S) of formula 11.1 to compounds of formula 11.2, which can be accomplished via reductive alkylation using a carbonyl compound of formula 2.5 and a reducing agent such as sodium borohydride, sodium cyanoborohydride, sodium triacetoxyborohydride, or tetramethylammonium triacetoxyborohydride.

Appropriately substituted 2-hydroxyanilines or 2-thioanilines of formula 11.2 may be caused to react with an appropriately substituted benzene of formula 3.2 under Ullmann type conditions or under basic conditions such as potassium carbonate in DMF (when $X_1$=$NO_2$) as shown in stage 11.3 to yield compounds of formula 1.6. Appropriate $X_1$ and $X_2$ substituents may include halogens, trifluoromethanesulfonyloxy, and a nitro group.

The regiochemical outcome of the condensation of compounds of formula 11.2 with compounds of formula 3.2 depends on the position of the Q substituent in compounds of formula 3.2 and on the reaction conditions used for the condensation. An extensive review on this topic is available in the literature (see, for eample: 'The Smiles and Related Rearrangements of aromatic Systems' by W. E. Truce, E. M. Kreider, and W. W. Brand in Organic Reactions, 1970, Vol. 18, pp. 99-215).

In compounds of formula 11.1 where Y is sulfur, an intermediate spiro compound of formula 11.3 may be formed. Compounds of formula 11.3 may be converted to compounds of formula 11.2 (Y=S) by treatment with a hydride reagent such as lithium aluminum hydride or sodium borohydride.

In the above Schemes 1 through 11, the Q function of compounds of formula 2 may be converted into group G, which may be —C(Z)NR$_1$R$_2$, an aryl substituent, or an appropriate heterocycle as defined herein, to give compounds of formula 3. When the Q function of compounds of formula 2 is a halogen or trifluoromethanesulfonyloxy, it may be converted to an ester via alkoxycarbonylation using carbon monoxide, an aliphatic alcohol, a trialkanyl amine, and a palladium catalyst such as bis(triphenylphosphine) palladium(II) dichloride. Subsequently, when Q is an ester, the ester may be hydrolyzed to a carboxylic acid. The carboxylic acid may then be coupled with ammonia, a primary amine, or a secondary amine to form a primary, secondary or tertiary amide, respectively. Alternatively, the conversion of a carboxylic acid to an amide may be carried out via an acid chloride using thionyl chloride, oxalyl chloride, or the like, followed by a Schotten-Baumann reaction using ammonia or an amine in the presence of an alkali metal hydroxide. Alternatively, the conversion of a carboxylic acid to an amide may be carried out via the use of peptide coupling agents such as 1,3-dicyclohexylcarbondiimide (DCC), O-(7-azabenzotriazol-1-yl)-N,N,N'N'-tetramethyluronium hexafluorophosphate (HATU), O-benzotriazol-1-yl-N,N,N'N'-tetramethyluronium hexafluorophosphate (HBTU), or the like. Alternatively, the ester may be converted directly to the amide by the action of a dimethylaluminum amide.

Alternatively, when the Q function of compounds of formula 2 is a halogen or trifluoromethanesulfonyloxy, it may be converted directly to an amide via aminocarbonylation using a carbon monoxide source such as molybdenum hexacarbonyl, an amine, a base such as DBU, and a palladium catalyst such as Herrmann's catalyst.

Instead of proceeding to compounds of formula 3 via an ester, one may effect the transformation of the group Q to a substituent G (wherein G is an amidino or heterocycle) by way of a nitrile. Synthesis of the nitrile may be accomplished by treatment of the compounds of formula 2 (when Q is bromo or trifluoromethanesulfonyloxy) with $Zn(CN)_2$ and a palladium catalyst such as $(Ph_3P)_4Pd$ or by treatment of the compounds of formula 2 with CuCN at elevated temperatures. For the synthesis of amidino functional groups, the nitrile is treated with hydroxylamine under basic conditions to afford an oxime. Treatment of the oxime with a primary or secondary amine, CuCl, and an alkali metal carbonate under microwave irradiation in an alcoholic solvent provides the amidino compounds of the present invention. Microwave accelerated reactions may be performed using either a CEM Discover or a Personal Chemistry Smith Synthesizer microwave instrument. The oxime described above is instrumental in the preparation of compounds wherein G is a heterocycle. The oxime may be cyclized with a variety of electrophiles known to one versed in the art to give the heterocycles of the present invention. For instance, reaction of an oxime with CDI provides oxadiazolones, and treatment of the oxime with TCDI provides the corresponding oxadiazolethiones. Similarly, the treatment of the oxime with thionyl chloride in the presence of a tertiary amine gives oxathiadiazoles of the present invention.

An aryl substituent may be installed in place of the functional group Q by coupling compounds of formula 2 (when Q is bromo or trifluoromethanesulfonyloxy) with a suitably substituted arylboronic acid in the presence of a palladium catalyst and an alkali metal carbonate.

Desired end products of the present invention may include chemical modifications at $R_4$. Such transformations may include the dealkylation of lower alkyl ethers to give their corresponding alcohols, using reagents such as boron trihalides. Compounds where $R_4$ is a halogen atom may participate in transition metal-mediated coupling reactions such as Suzuki, Stille or Negishi chemistry.

It is generally preferred that the respective product of each process step be separated from other components of the reaction mixture and subjected to purification before its use as a starting material in a subsequent step. Separation techniques typically include evaporation, extraction, precipitation and filtration. Purification techniques typically include column chromatography (Still, W. C. et. al., *J. Org. Chem.* 1978, 43, 2921), thin-layer chromatography, crystallization and distillation. The structures of the final products, intermediates and starting materials are confirmed by spectroscopic, spectrometric and analytical methods including nuclear magnetic resonance (NMR), mass spectrometry (MS) and liquid chromatography (HPLC). In the descriptions for the preparation of compounds of this invention, ethyl ether, tetrahydrofuran and dioxane are common examples of an ethereal solvent; benzene, toluene, hexanes and heptanes are typical hydrocarbon solvents and dichloromethane and dichloroethane are representative halogenated hydrocarbon solvents. In those cases where the product is isolated as the acid addition salt the free base may be obtained by techniques known to those skilled in the art. In those cases in which the product is isolated as an acid addition salt, the salt may contain one or more equivalents of the acid. Enantiomers of the compounds of the present invention may be separated using chiral HPLC.

Representative compounds of the present invention can be synthesized in accordance with the general synthetic methods described above and are illustrated more particularly in the schemes that follow. Since the schemes are illustrations, the invention should not be construed as being limited by the chemical reactions and conditions expressed. The preparation of the various starting materials used in the schemes is well within the skill of persons versed in the art.

ABBREVIATIONS

AcOH=acetic acid
Boc=tert-butoxycarbonyl
$CH_3CN$=acetonitrile
DIEA=N,N-diisopropyl-N-ethylamine
DME=dimethoxyethane
DMF=N,N-dimethylformamide
DMSO=dimethyl sulfoxide
Et=ethyl
EtOAc=ethyl acetate
h=hour(s)
HATU=O-(7-azabenzotriazol-1-yl)-N,N,N',N'-tetramethyluronium hexafluorophosphate
HBTU=O-benzotriazol-1-yl-N,N',N'-tetramethyluronium hexafluorophosphate
$K_2CO_3$=potassium carbonate
Me=methyl
min=minute(s)
rt=room temperature
TFA=trifluoroacetic acid
THF=tetrahydrofuran

EXAMPLES

Example A

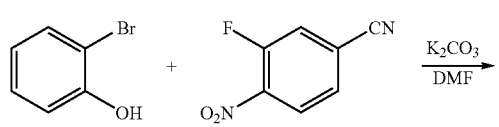

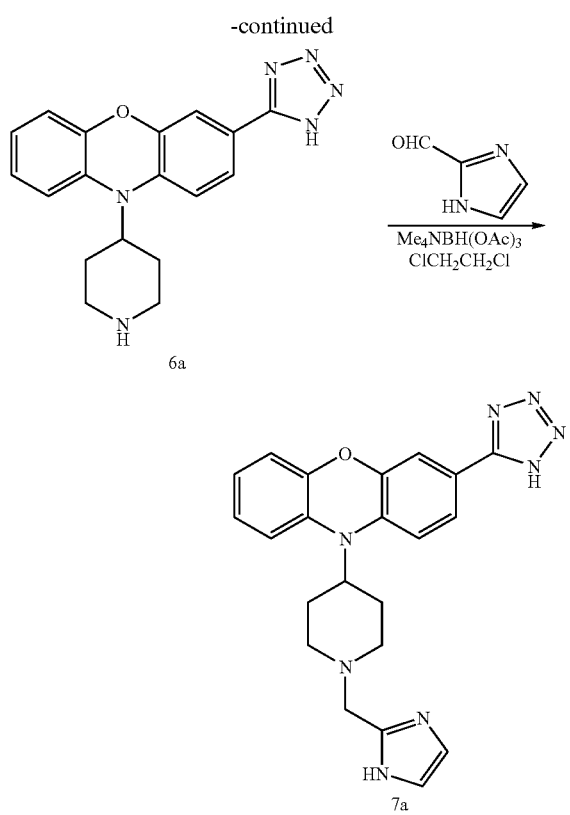

Procedure 1

3-(2-Bromo-phenoxy)-4-nitrobenzonitrile, 1a

To a solution of 3-fluoro-4-nitrobenzonitrile (6.3 g; 37.93 mmol) and 2-bromophenol (4.4 mL; 37.94 mmol) in DMF (50 mL) was added potassium carbonate (6.29 g; 45.51 mmol). The mixture was stirred for 5 h at rt. Water (100 mL) was added, and a precipitate formed. The solid was separated via filtration, washed with water, and dried to yield 11.20 g (92.5%) of 3-(2-bromo-phenoxy)-4-nitrobenzonitrile, 1a.

Procedure 2

4-Amino-3-(2-bromophenoxy)-benzonitrile, 2a

To a mixture of 3-(2-bromophenoxy)-4-nitrobenzonitrile, 1 (5 g; 15.67 mmol) in methanol (100 mL) was added tin(II) chloride dihydrate (17.68 g; 78.36 mmol). The mixture was stirred at rt overnight, and the solvent was removed via evaporation. Ethyl acetate (100 mL) and 1N NaOH (100 mL) were added, and the solvents were removed via evaporation. Ethyl acetate (200 mL) was added, and white solid formed. The solid was removed via filtration, washed with ethyl acetate, and the combined filtrates were evaporated. The residue was purified via column chromatography (eluent gradient: 10% to 30% ethyl acetate in heptane) to yield 3.0 g (66%) of 4-amino-3-(2-bromophenoxy)-benzonitrile, 2a. MS m/z (MH$^+$) 288.7/289.7.

Procedure 3

4-[2-(2-Bromophenoxy)-4-cyanophenylamino]-piperidine-1-carboxylic acid tert-butyl ester, 3a To a solution of 4-amino-3-(2-bromophenoxy)-benzonitrile, 2a (0.8 g; 2.77 mmol) and 4-oxo-piperidine-1-carboxylic acid tert-butyl ester (1.1 g; 5.52 mmol) in dichloroethane (80 mL) was added sodium triacetoxyborohydride (1.17 g; 5.52 mmol) and acetic acid (0.16 mL; 2.8 mmol). The mixture was stirred for 2 h at rt. An additional 4 equiv of sodium triacetoxyborohydride was added, and the mixture was heated to 90° C. for 5 h. The mixture was allowed to cool to rt, diluted with ethyl acetate (15 mL) and treated with H$_2$O (15 mL). The organic layer was separated, dried over MgSO$_4$, filtered, and evaporated. The residue was purified via column chromatography (eluent gradient: 0 to 30% ethyl acetate in heptane) to yield 0.6 g (46%) of 4-[2-(2-bromophenoxy)-4-cyanophenylamino]-piperidine-1-carboxylic acid tert-butyl ester, 3a. MS m/z (MH$^+$) 493.7.

Procedure 4

4-(3-Cyanophenoxazin-10-yl)-piperidine-1-carboxylic acid tert-butyl ester, 4a To a suspension of sodium hydride (0.1-1 g; 0.74 mmol) in DMF (5 mL) was added a solution of 4-[2-(2-bromophenoxy)-4-cyanophenylamino]-piperidine-1-carboxylic acid tert-butyl ester, 3a (0.35 g; 0.74 mmol) in DMF (3 mL). The mixture was heated to 120° C. for 90 min and allowed to cool to rt. The mixture was poured into ice-water and a precipitate formed. The solid was separated via filtration, dried to yield 4-(3-cyanophenoxazin-10-yl)-piperidine-1-carboxylic acid tert-butyl ester, 4a. MS m/z (M+Na) 413.9. The material was used as such for the next reaction.

Procedure 5

4-[3-(1H-Tetrazol-5-yl)-phenoxazin-10-yl]-piperidine-1-carboxylic acid tert-butyl ester, 5a To a solution of 4-(3-cyanophenoxazin-10-yl)-piperidine-1-carboxylic acid tert-butyl ester, 4a (0.29 g; 0.68 mmol) in DMF (7 mL) were added sodium azide (0.13 g, 2.0 mmol) and ammonium chloride (0.11 g; 2.06 mmol), and the mixture was heated at 120° C. for 16 h. The mixture was allowed to cool to rt, and filtered. The filtrate was acidified with 1N hydrochloric acid (10 mL) and extracted with ethyl acetate (3×10 mL). The combined organic layers were dried over MgSO$_4$, filtered, and evaporated, yielding 4-[3-(1H-tetrazol-5-yl)-phenoxazin-10-yl]-piperidine-1-carboxylic acid tert-butyl ester, 5a. MS m/z (M+Na) 456.9. The crude material was used as such for the next reaction.

Procedure 6

10-Piperidin-4-yl-3-(1H-tetrazol-5-yl)-10H-phenoxazine, 6a

To a solution of 4-[3-(1H-tetrazol-5-yl)-phenoxazin-10-yl]-piperidine-1-carboxylic acid tert-butyl ester, 5a (0.265 g, 0.61 mmol) in DMF (2 mL) was added a 4N hydrochloric acid solution (4 mL). The mixture was stirred for 2 h at rt. Another 4 mL of the 4N HCl solution was added, and the mixture was stirred for 16 h at rt. The solvent was removed via evaporation, and the residue was purified via reverse phase chromatography (eluent gradient: 10 to 40% acetonitrile in water containing 0.1% TFA) to yield 0.12 g (44%) of 10-piperidin-4-yl-3-(1H-tetrazol-5-yl)-10H-phenoxazine, 6a as a TFA salt. MS m/z (MH$^+$) 335.0.

Procedure 7

10-[1-(1H-Imidazol-2-ylmethyl)-piperidin-4-yl]-3-(1H-tetrazol-5-yl)-10H-phenoxazine, 7a To a solution of the TFA salt of 10-piperidin-4-yl-3-(1H-tetrazol-5-yl)-10H-phenoxazine, 6a (40.7 mg; 0.091 mmol) and 1H-imidazole-2-carboxaldehyde (35 mg; 0.36 mmol) in dichloroethane (5 mL) was added tetramethylammonium triacetoxyborohydride (36 mg; 0.14 mmol). The mixture was heated to 80° C. for 15 hr in a sealed tube. The mixture was allowed to cool to rt, and the solvent was removed via evaporation. The residue was purified via reverse phase HPLC (eluent gradient: 15 to 40% acetonitrile in water containing 0.1% TFA) to yield 3.1 mg (6.5%) of 10-[1-(1H-imidazol-2-ylmethyl)-piperidin-4-yl]-3-(1H-tetrazol-5-yl)-10H-phenoxazine, 7a as a TFA salt. MS m/z (MH$^+$) 414.9.

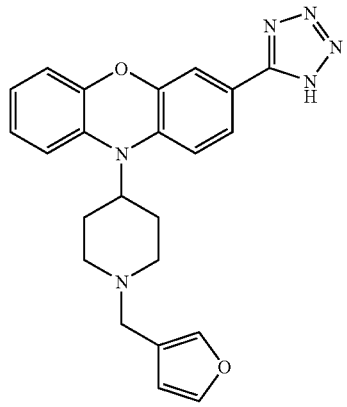

10-(1-Furan-3-ylmethyl-piperidin-4-yl)-3-(1H-tetrazol-5-yl)-10H-phenoxazine, 8a

Using an adaptation of the method described in Procedure 7, substituting 3-furyl carboxaldehyde for 1H-imidazole-2-carboxaldehyde and sodium triacetoxyborohydride for tetramethylammonium triacetoxyborohydride, the title compound 10-(1-furan-3-ylmethyl-piperidin-4-yl)-3-(1H-tetrazol-5-yl)-10H-phenoxazine, 8a was obtained as a TFA salt after purification via reverse phase HPLC (eluent: CH$_3$CN in H$_2$O containing 0.1% TFA). MS m/z (MH$^+$) 414.9.

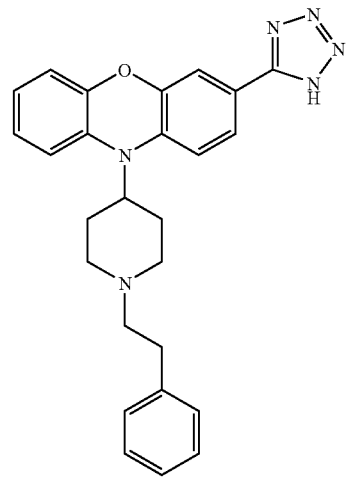

10-(1-Phenethyl-piperidin-4-yl)-3-(1H-tetrazol-5-yl)-10H-phenoxazine, 9a

Using an adaptation of the method described in Procedure 7, substituting phenyl acetaldehyde for 1H-imidazole-2-carboxaldehyde, and sodium triacetoxyborohydride for tetramethylammonium triacetoxyborohydride, the title compound 10-(1-phenethyl-piperidin-4-yl)-3-(1H-tetrazol-5-yl)-10H-phenoxazine, 9a was obtained as a TFA salt after purification via reverse phase HPLC (eluent: CH$_3$CN in H$_2$O containing 0.1% TFA). MS m/z (MH$^+$) 438.9.

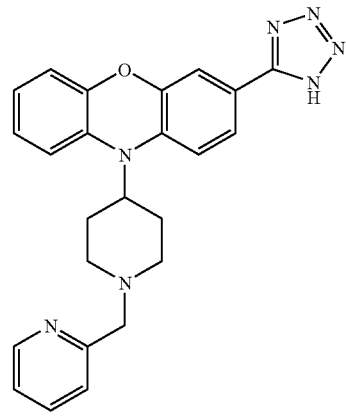

10-(1-Pyridin-2-ylmethyl-piperidin-4-yl)-3-(1H-tetrazol-5-yl)-10H-phenoxazine, 10a Using an adaptation of the method described in Procedure 7, substituting 2-pyridylcarboxaldehyde for 1H-imidazole-2- carboxaldehyde, and sodium triacetoxyborohydride for tetramethylammonium triacetoxyborohydride, the title compound 10-(1-pyridin-2-ylmethyl-piperidin-4-yl)-3-(1H-tetrazol-5-yl)-10H-phenoxazine, 10a was obtained as a TFA salt after purification via reverse phase HPLC (eluent: CH$_3$CN in H$_2$O containing 0.1% TFA). MS m/z (MH$^+$) 425.9.

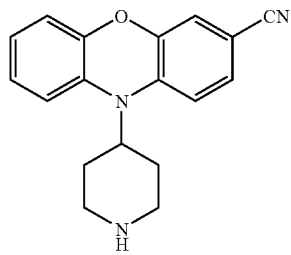

10-Piperidin-4-yl-10H-phenoxazine-3-carbonitrile, 11a

Using an adaptation of the method described in Procedure 6, substituting 4-(3-cyanophenoxazin-10-yl)-piperidine-1-carboxylic acid tert-butyl ester, 4a for 4-[3-(1H-tetrazol-5-yl)-phenoxazin-10-yl]-piperidine-1-carboxylic acid tert-butyl ester, 5a, the title compound 10-piperidin-4-yl-10H-phenoxazine-3-carbonitrile, 11a was obtained as a TFA salt after purification via reverse phase HPLC (eluent: CH$_3$CN in H$_2$O containing 0.1% TFA). MS m/z (MH$^+$) 291.9.

10-Piperidin-4-yl-10H-phenoxazine-3-carboxylic Acid amide, 12a

Using an adaptation of the method described in Procedure 6, substituting 10-piperidin-4-yl-10H-phenoxazine-3-carbonitrile, 11a for 4-[3-(1H-tetrazol-5-yl)-phenoxazin-10-yl]-piperidine-1-carboxylic acid tert-butyl ester, 5a, the title compound 10-piperidin-4-yl-10H-phenoxazine-3-carboxylic acid amide, 12a was obtained as a TFA salt after purification via reverse phase HPLC (eluent: CH$_3$CN in H$_2$O containing 0.1% TFA). MS m/z (MH$^+$) 309.9.

Example B

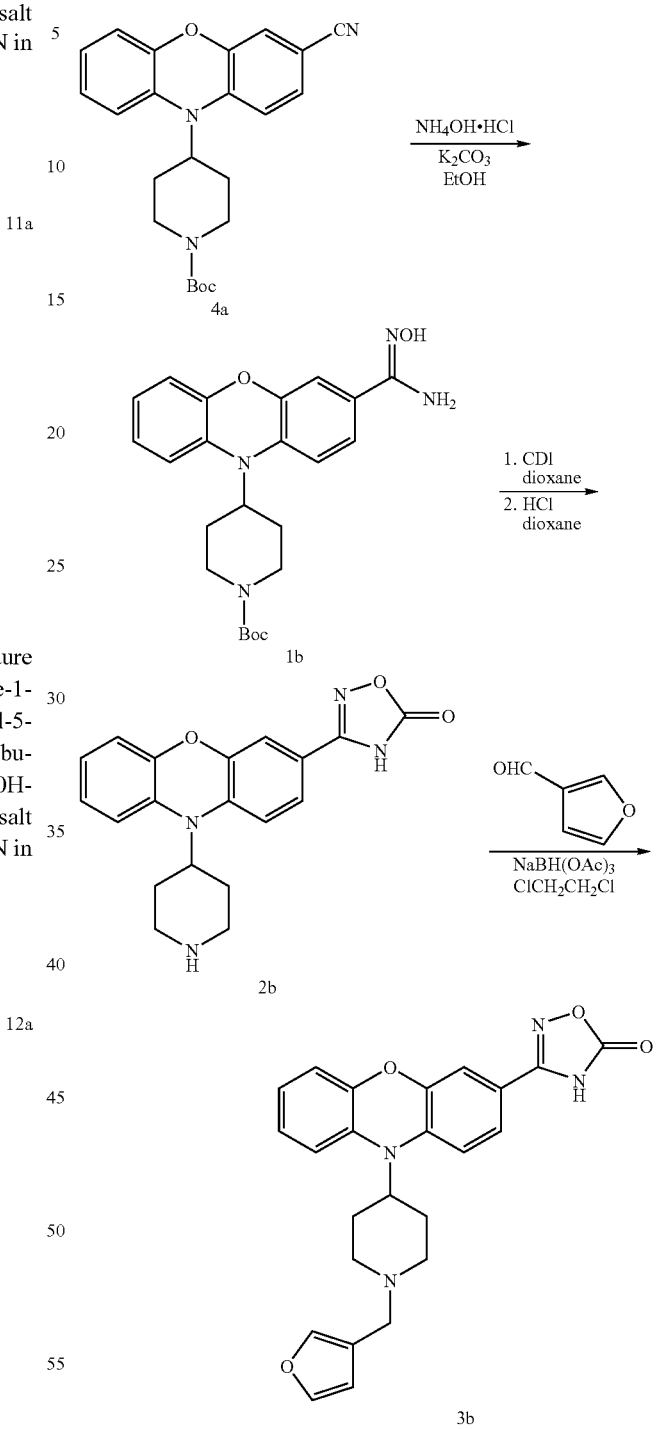

Procedure 8

4-[3-(N-Hydroxycarbamimidoyl)-phenoxazin-10-yl]-piperidine-1-carboxylic acid tert-butyl ester, 1b To a solution of 4-(3-cyanophenoxazin-10-yl)-piperidine-1-carboxylic acid tert-butyl ester, 4a (130 mg; 0.33 mmol) in ethanol (3 mL) was added ammonium hydroxide hydrochlo ride (69 mg; 0.99 mmol) and potassium carbonate (91 mg; 0.66 mmol), and the mixture was heated to reflux for 16 h. The mixture was allowed to cool to rt, water (5 mL) was added, and the mixture was extracted with ethyl acetate (2×5 mL). The combined organic layers were dried over MgSO$_4$, filtered, and evaporated, yielding 4-[3-(N-hydroxycarbamimidoyl)-phenoxazin-10-yl]-piperidine-1-carboxylic acid tert-butyl ester, 1b. The crude material was used as such in the next reaction. MS m/z (M+Na) 473.

Procedure 9

3-(10-Piperidin-4-yl-10H-phenoxazin-3-yl)-4H-[1,2,4]oxadiazol-5-one, 2b

To a solution of 4-[3-(N-hydroxycarbamimidoyl)-phenoxazin-10-yl]-piperidine-1-carboxylic acid tert-butyl ester, 1b (0.13 g; 0.31 mmol) in dioxane (5 mL) was added 1,1'-carbonyldiimidazole (75 mg; 0.46 mmol), and the mixture was stirred at 110° C. for 4 hr. The mixture was allowed to cool to rt, and treated with 4N HCl in dioxane (5 mL). The mixture was stirred at rt for 16 hr and evaporated. The residue was suspended in methanol, and the solid was removed via filtration. The filtrate was purified via reverse phase HPLC (eluent gradient: 20 to 40% CH$_3$CN in water containing 0.1% TFA) to yield 8.8 mg (14.4%) of 3-(10-piperidin-4-yl-10H-phenoxazin-3-yl)-4H-[1,2,4]oxadiazol-5-one, 2b as a TFA salt. MS m/z (MH$^+$) 351.1.

3-[10-(1-Furan-3-ylmethyl-piperidin-4-yl)-10H-phenoxazin-3-yl]-4H-[1,2,4]oxadiazol-5-one, 3b Using an adaptation of the method described in Procedure 7, substituting the TFA salt of 3-(10-piperidin-4-yl-10H-phenoxazin-3-yl)-4H-[1,2,4]oxadiazol-5-one, 2b for the TFA salt of 10-piperidin-4-yl-3-(1H-tetrazol-5-yl)-10H-phenoxazine, 6a, 3-furyl carboxaldehyde for 1H-imidazole-2-carboxaldehyde and sodium triacetoxyborohydride for tetramethylammonium triacetoxyborohydride, the title compound 3-[10-(1-furan-3-ylmethyl-piperidin-4-yl)-10H-phenoxazin-3-yl]-4H-[1,2,4]oxadiazol-5-one, 3b was obtained as a TFA salt after purification via reverse phase HPLC (eluent: CH$_3$CN in H$_2$O containing 0.1% TFA). MS m/z (MH$^+$) 438.8.

noxazin-3-yl)-4H-[1,2,4]oxadiazol-5-one, 2b for the TFA salt of 10-piperidin-4-yl-3-(1H-tetrazol-5-yl)-10H-phenoxazine, 6a, phenyl acetaldehyde for 1H-imidazole-2-carboxaldehyde and sodium triacetoxyborohydride for tetramethylammonium triacetoxyborohydride, the title compound 3-[10-(1-phenethyl-piperidin-4-yl)-10H-phenoxazin-3-yl]-4H-[1,2,4]oxadiazol-5-one, 4b was obtained as a TFA salt after purification via reverse phase HPLC (eluent: CH$_3$CN in H$_2$O containing 0.1% TFA). MS m/z (MH$^+$) 454.8.

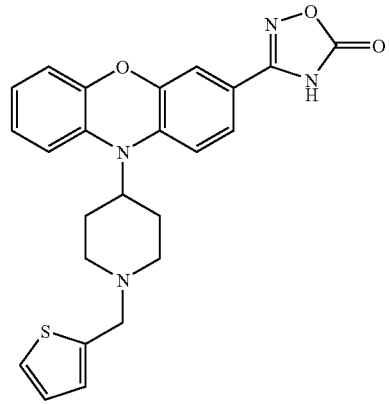

3-[10-(1-Thiophen-2-ylmethyl-piperidin-4-yl)-10H-phenoxazin-3-yl]-4H-[1,2,4]oxadiazol-5-one, 5b Using an adaptation of the method described in Procedure 7, substituting the TFA salt of 3-(10-piperidin-4-yl-10H-phenoxazin-3-yl)-4H-[1,2,4]oxadiazol-5-one, 2b for the TFA salt of 10-piperidin-4-yl-3-(1H-tetrazol-5-yl)-10H-phenoxazine, 6a, 2-thiophene carboxaldehyde for 1H-imidazole-2-carboxaldehyde and sodium triacetoxyborohydride for tetramethylammonium triacetoxyborohydride, the title compound 3-[10-(1-thiophen-2-ylmethyl-piperidin-4-yl)-10H-phenoxazin-3-yl]-4H-[1,2,4]oxadiazol-5-one, 5b was obtained as a TFA salt after purification via reverse phase HPLC (eluent: CH$_3$CN in H$_2$O containing 0.1% TFA). MS m/z (MH$^+$) 446.9.

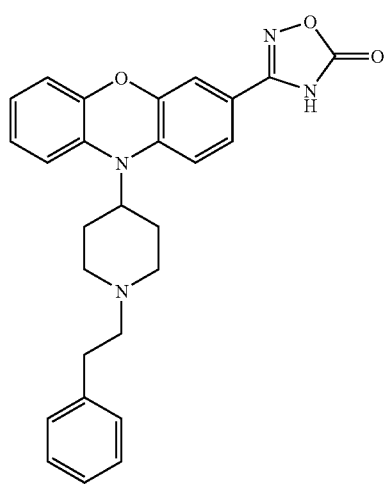

3-[10-(1-Phenethyl-piperidin-4-yl)-10H-phenoxazin-3-yl]-4H-[1,2,4]oxadiazol-5-one, 4b Using an adaptation of the method described in Procedure 7, substituting the TFA salt of 3-(10-piperidin-4-yl-10H-phe-

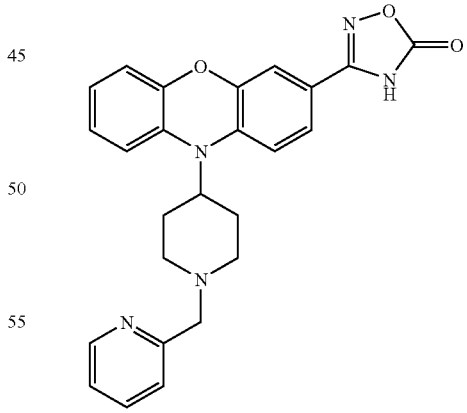

3-[10-(1-Pyridin-2-ylmethyl-piperidin-4-yl)-10H-phenoxazin-3-yl]-4H-[1,2,4]oxadiazol-5-one, 6b Using an adaptation of the method described in Procedure 7, substituting the TFA salt of 3-(10-piperidin-4-yl-10H-phenoxazin-3-yl)-4H-[1,2,4]oxadiazol-5-one, 2b for the TFA salt of 10-piperidin-4-yl-3-(1H-tetrazol-5-yl)-10H-phenoxazine, 6a, 2-pyridylcarboxaldehyde for 1H-imidazole-2-carboxaldehyde and sodium triacetoxyborohydride for tetramethylammonium triacetoxyborohydride, the title compound 3-[10-(1-pyridin-2-ylmethyl-piperidin-4-yl)-10H-phenoxazin-3-yl]-4H-[1,2,4]oxadiazol-5-one, 6b was obtained as a TFA salt after purification via reverse phase HPLC (eluent: $CH_3CN$ in $H_2O$ containing 0.1% TFA). MS m/z ($MH^+$) 441.9.

Example C

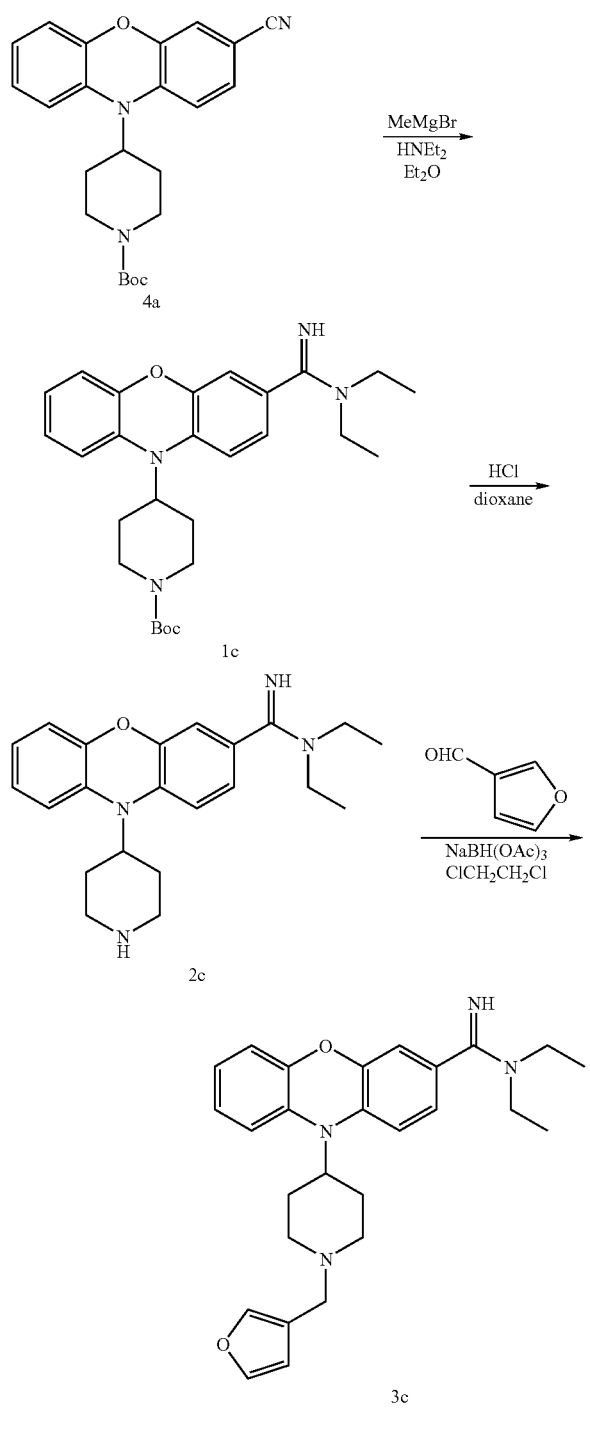

Procedure 10

4-[3-(N,N-Diethyl-carbamimidoyl)-phenoxazin-10-yl]-piperidine-1-carboxylic acid tert-butyl ester, 1c To a solution of methylmagnesium bromide in diethyl ether (3.0 M, 2.4 mL) under a $N_2$ atmosphere was added dropwise a solution of diethylamine (0.8 mL; 7.68 mmol) in diethyl ether (2 mL). The mixture was heated to reflux for 30 min and allowed to cool to rt. A suspension of 4-(3-cyanophenoxazin-10-yl)-piperidine-1-carboxylic acid tert-butyl ester, 4a (1 g; 2.55 mmol) in diethyl ether (10 mL) was added, and the mixture was heated to reflux for 2 h. Water (10 mL) was added, and the organic layer was separated. The aqueous layer was extracted with chloroform (2×10 mL), and the combined organic layers were dried over $MgSO_4$, filtered, and evaporated. The residue was used as such for the next reaction. MS m/z ($MH^+$) 465.0.

N,N-Diethyl-10-piperidin-4-yl-10H-phenoxazine-3-carboxamidine, 2c

Using an adaptation of the method described in Procedure 6, substituting 4-[3-(N,N-diethylcarbamimidoyl)-phenoxazin-10-yl]-piperidine-1-carboxylic acid tert-butyl ester, 1c, for 4-[3-(1H-tetrazol-5-yl)-phenoxazin-10-yl]-piperidine-1-carboxylic acid tert-butyl ester, 5a, and dioxane for DMF, the title compound N,N-diethyl-10-piperidin-4-yl-10H-phenoxazine-3-carboxamidine, 2c was obtained as a TFA salt after purification via reverse phase HPLC (eluent gradient: 10 to 35% $CH_3CN$ in $H_2O$ containing 0.1% TFA). MS m/z ($MH^+$) 365.2.

N,N-Diethyl-10-(1-furan-3-ylmethyl-piperidin-4-yl)-10H-phenoxazine-3-carboxamidine, 3c Using an adaptation of the method described in Procedure 7, substituting the TFA salt of N,N-diethyl-10-piperidin-4-yl-10H-phenoxazine-3-carboxamidine, 2c for the TFA salt of 10-piperidin-4-yl-3-(1H-tetrazol-5-yl)-10H-phenoxazine, 6a, 3-furyl carboxaldehyde for 1H-imidazole-2-carboxaldehyde and sodium triacetoxyborohydride for tetramethylammonium triacetoxyborohydride, the title compound N,N-diethyl-10-(1-furan-3-ylmethyl-piperidin-4-yl)-10H-phenoxazine-3-carboxamidine, 3c was obtained as a TFA salt after purification via reverse phase HPLC (eluent: $CH_3CN$ in $H_2O$ containing 0.1% TFA). MS m/z ($MH^+$) 444.9.

N,N-Diethyl-10-(1-phenethyl-piperidin-4-yl)-10H-phenoxazine-3-carboxamidine, 4c Using an adaptation of the method described in Procedure 7, substituting the TFA salt of N,N-diethyl-10-piperidin-4-yl-10H-phenoxazine-3-carboxamidine, 2c for the TFA salt of 10-piperidin-4-yl-3-(1H-tetrazol-5-yl)-10H-phenoxazine, 6a, phenyl acetaldehyde for 1H-imidazole-2-carboxaldehyde and sodium triacetoxyborohydride for tetramethylammonium triacetoxyborohydride, the title compound N,N-diethyl-10-(1-phenethyl-piperidin-4-yl)-10H-phenoxazine-3-carboxamidine, 4c was obtained as a TFA salt after purification via reverse phase HPLC (eluent: CH$_3$CN in H$_2$O containing 0.1% TFA). MS m/z (MH$^+$) 468.9.

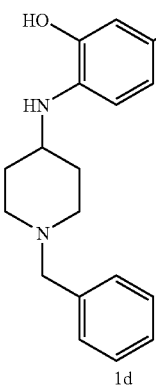

5c

N,N-Diethyl-10-(1-pyridin-2-ylmethyl-piperidin-4-yl)-10H-phenoxazine-3-carboxamidine, 5c Using an adaptation of the method described in Procedure 7, substituting the TFA salt of N,N-diethyl-10-piperidin-4-yl-10H-phenoxazine-3-carboxamidine, 2c for the TFA salt of 10-piperidin-4-yl-3-(1H-tetrazol-5-yl)-10H-phenoxazine, 6a, 2-pyridylcarboxaldehyde for 1H-imidazole-2-carboxaldehyde and sodium triacetoxyborohydride for tetramethylammonium triacetoxyborohydride, the title compound N,N-diethyl-10-(1-pyridin-2-ylmethyl-piperidin-4-yl)-10H-phenoxazine-3-carboxamidine, 5c was obtained as a TFA salt after purification via reverse phase HPLC (eluent: CH$_3$CN in H$_2$O containing 0.1% TFA). MS m/z (MH$^+$) 456.

Example D

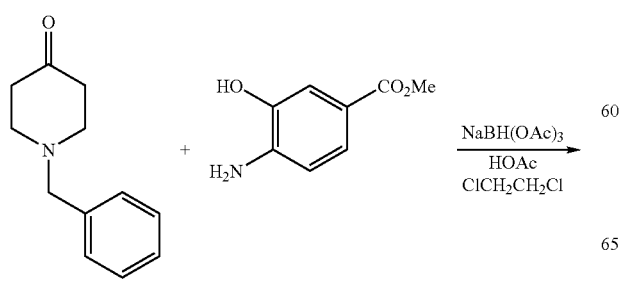

-continued

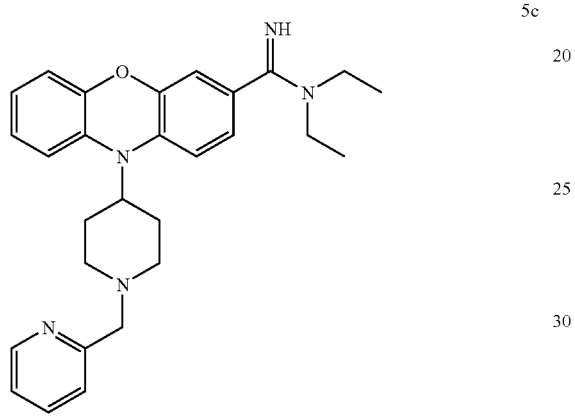

1d

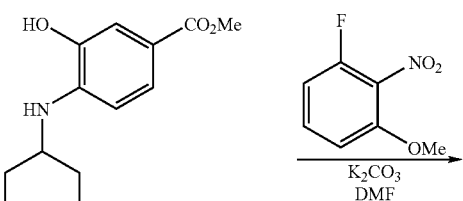

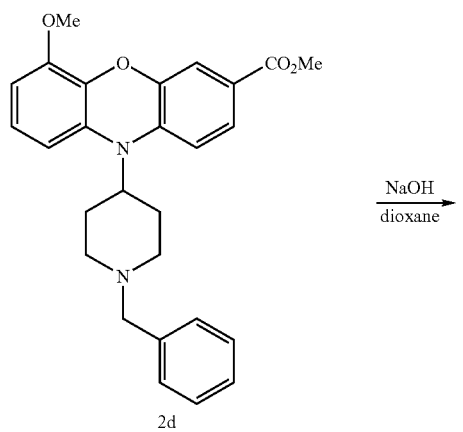

2d

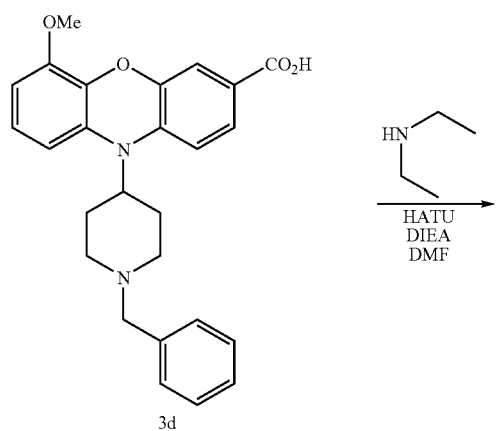

3d

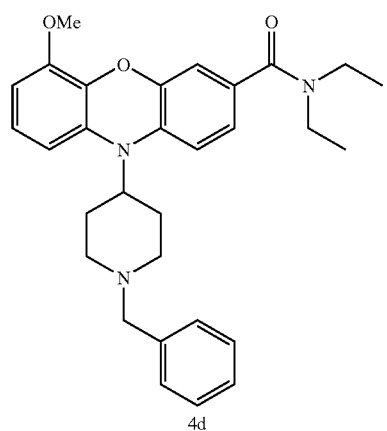

4d

+

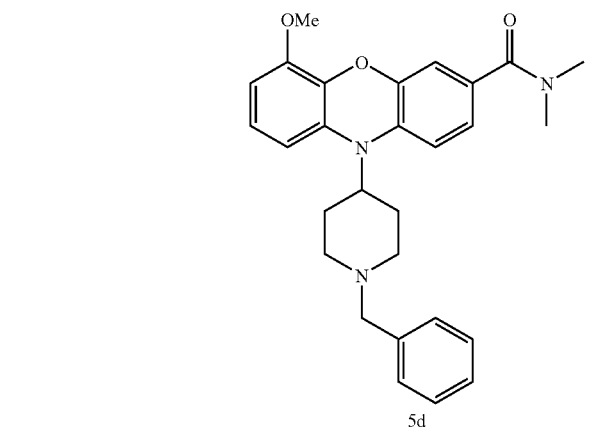

5d

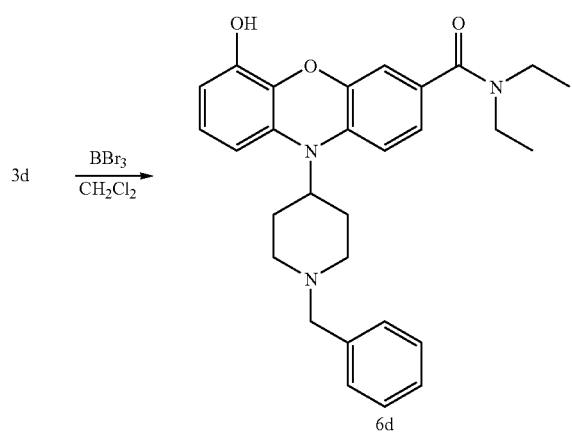

6d

4-(1-Benzyl-piperidin-4-ylamino)-3-hydroxy-benzoic acid methyl ester, 1d

Using an adaptation of the method described in Procedure 7, substituting 4-amino-3-hydroxy-benzoic acid methyl ester for the TFA salt of 10-piperidin-4-yl-3-(1H-tetrazol-5-yl)-10H-phenoxazine, 6a, 1-benzyl-piperidin-4-one for 1H-imidazole-2-carboxaldehyde, and sodium triacetoxyborohydride for tetramethylammonium triacetoxyborohydride, the title compound 4-(1-benzyl-piperidin-4-ylamino)-3-hydroxy-benzoic acid methyl ester, 1d was obtained.

10-(1-Benzyl-piperidin-4-yl)-6-methoxy-10H-phenoxazine-3-carboxylic acid methyl ester, 2d Using an adaptation of the method described in Procedure 1, substituting 4-(1-benzyl-piperidin-4-ylamino)-3-hydroxybenzoic acid methyl ester, 1d for 2-bromophenol, and 1-fluoro-3-methoxy-2-nitrobenzene for 3-fluoro-4-nitrobenzonitrile, the title compound 10-(1-benzyl-piperidin-4-yl)-6-methoxy-10H-phenoxazine-3-carboxylic acid methyl ester, 2d was obtained.

Procedure 11

10-(1-Benzyl-piperidin-4-yl)-6-methoxy-10H-phenoxazine-3-carboxylic acid, 3d To a solution of 10-(1-benzyl-piperidin-4-yl)-6-methoxy-10H-phenoxazine-3-carboxylic acid methyl ester, 2d (270 mg, 0.7 mmol) in dioxane (15 mL) was added sodium hydroxide (31 mg, 0.77 mmol) and the mixture was heated to reflux for 4 h. The mixture was allowed to cool to rt, water (15 mL) was added, and the solution was acidified with 1N HCl to pH 2. The mixture was extracted with methylene chloride, the organic phase was separated, dried, and evaporated to yield 245 mg (94%) of title compound 10-(1-benzyl-piperidin-4-yl)-6-methoxy-10H-phenoxazine-3-carboxylic acid, 3d.

Procedure 12

10-(1-Benzyl-piperidin-4-yl)-6-methoxy-10H-phenoxazine-3-carboxylic acid diethylamide, 4d and 10-(1-Benzyl-piperidin-4-yl)-6-methoxy-10H-phenoxazine-3-carboxylic acid dimethylamide, 5d To a solution of 10-(1-benzyl-piperidin-4-yl)-6-methoxy-10H-phenoxazine-3-carboxylic acid, 3d (240 mg, 0.56 mmol) in DMF was added HATU (424 mg, 1.11 mmol), N,N-diisopropyl-N-ethylamine (115 mg, 1.12 mmol), and N,N-diethylamine (82 mg, 1.12 mmol). The mixture was allowed to stir overnight at rt. Water (5 mL) was added, and the solution was extracted with EtOAc. The organic layer was separated, dried, and evaporated. The residue was purified via reverse phase HPLC (eluent: $CH_3CN$ in water containing 0.1% TFA) to yield 93.3 mg (28%) of 10-(1-benzyl-piperidin-4-yl)-6-methoxy-10H-phenoxazine-3-carboxylic acid diethylamide, 4d and 91.4 mg (29%) of 10-(1-benzyl-piperidin-4-yl)-6-methoxy-10H-phenoxazine-3-carboxylic acid dimethylamide, 5d, both as TFA salts (presence of 5d is presumably due to N,N-dimethylamine present in DMF). 4d: MS m/z (MH$^+$) 486.0; 5d: MS m/z (MH$^+$) 458.8.

Procedure 13

10-(1-Benzyl-piperidin-4-yl)-6-hydroxy-10H-phenoxazine-3-carboxylic acid diethylamide, 6d To a solution of 10-(1-benzyl-piperidin-4-yl)-6-methoxy-10H-phenoxazine-3-carboxylic acid diethylamide, 4d (50 mg, 0.1 mmol) in methylene chloride (2 mL) at 0° C. was added a 1M solution of boron tribromide in methylene chloride (0.8 mL, 0.8 mmol). The mixture was allowed to stir for 15 min at rt, followed by stirring at rt for 4 h. A saturated $NaHCO_3$ solution and methylene chloride were added, and the organic phase was separated. The organic phase was dried, filtered, and evaporated. The residue was purified via reverse phase HPLC (eluent: $CH_3CN$ in water containing 0.1% TFA) to yield 17 mg (29%) of title compound 10-(1-benzyl-piperidin-4-yl)-6-hydroxy-10H-phenoxazine-3-carboxylic acid diethylamide, 6d as a TFA salt. MS m/z (MH$^+$) 471.0.

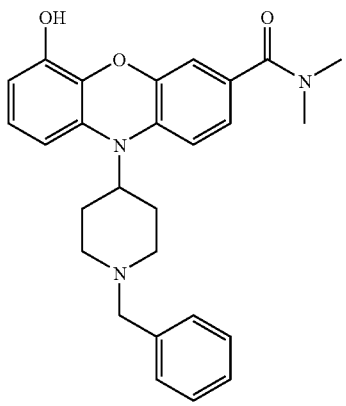

10-(1-Benzyl-piperidin-4-yl)-6-hydroxy-10H-phenoxazine-3-carboxylic acid dimethylamide, 7d Using an adaptation of the method described in Procedure 13, substituting 10-(1-benzyl-piperidin-4-yl)-6-methoxy-10H-phenoxazine-3-carboxylic acid dimethylamide, 5d for 10-(1-benzyl-piperidin-4-yl)-6-methoxy-10H-phenoxazine-3-carboxylic acid diethylamide, 4d, the title compound 10-(1-benzyl-piperidin-4-yl)-6-hydroxy-10H-phenoxazine-3-carboxylic acid dimethylamide, 7d was obtained as a TFA salt. MS m/z (MH$^+$) 443.9.

Example E

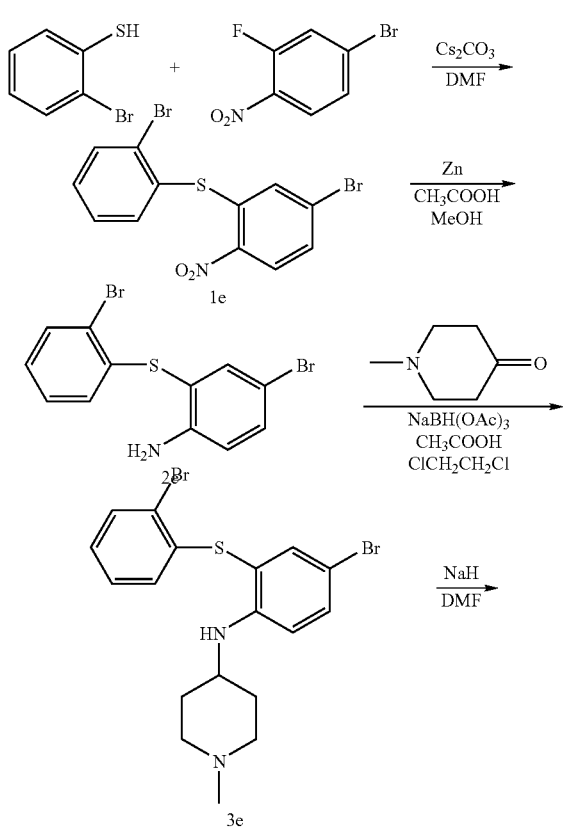

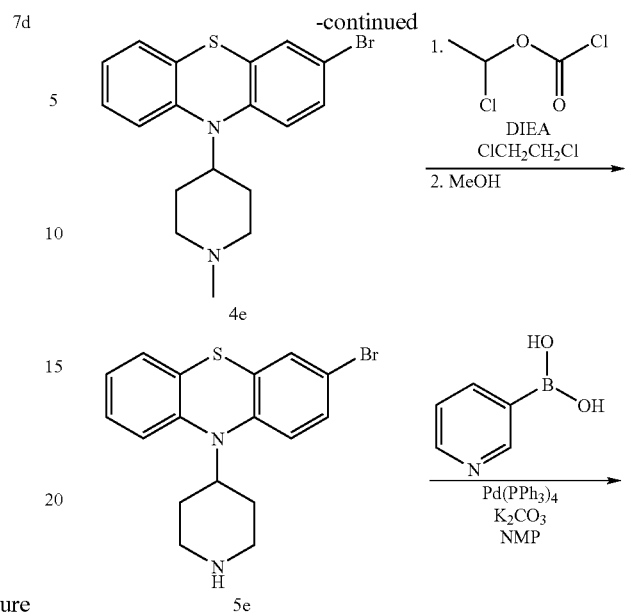

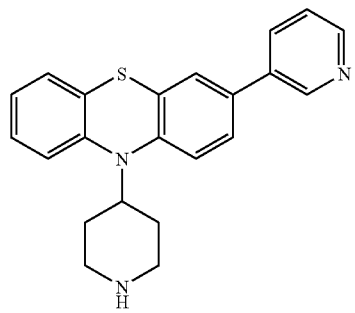

4-Bromo-2-(2-bromophenylsulfanyl)-nitrobenzene, 1e

Using an adaptation of the method described in Procedure 1, substituting 2-bromothiophenol for 2-bromophenol and 2-fluoro-4-bromonitrobenzene for 3-fluoro-4-nitrobenzonitrile, the title compound 4-bromo-2-(2-bromophenylsulfanyl)-nitrobenzene, 1e was obtained.

Procedure 14

4-Bromo-2-(2-bromophenylsulfanyl)-aniline, 2e

To a mixture of 4-bromo-2-(2-bromophenylsulfanyl)-nitrobenzene, 1e (15.56 g; 40 mmol) in acetic acid (200 mL) and methanol (400 mL) was added zinc (15.7 g; 240 mmol) over a 30 min period. The mixture was heated to 40° C. for 1 h overnight, filtered, evaporated, and dried under vacuum overnight. The residue was suspended in 1N NaOH solution and extracted with methylene chloride. The organic phase was dried over MgSO$_4$, filtered, and evaporated. The residue was purified via flash column chromatography (eluent gradient: 0 to 10% EtOAc in heptane) to yield 14.2 g (99%) of title compound 4-bromo-2-(2-bromophenylsulfanyl)-aniline, 2e.

[4-Bromo-2-(2-bromophenylsulfanyl)-phenyl]-(1-methyl-piperidin-4-yl)-amine, 3e Using an adaptation of the method described in Procedure 3, substituting 4-bromo-2-(2-bromophenylsulfanyl)-aniline, 2e for 4-amino-3-(2-bromophenoxy)-benzonitrile, 2a, and 1-methylpiperidin-4-one for 4-oxo-piperidine-1-carboxylic acid tert-butyl ester, the title compound [4-bromo-2-(2-bromophenylsulfanyl)-phenyl]-(1-methyl-piperidin-4-yl)-amine, 3e was obtained.

3-Bromo-10-(1-methylpiperidin-4-yl)-10H-phenothiazine, 4e

Using an adaptation of the method described in Procedure 4, substituting [4-bromo-2-(2-bromophenylsulfanyl)-phenyl]-(1-methyl-piperidin-4-yl)-amine, 3e for 4-[2-(2-bromophenoxy)-4-cyanophenylamino]-piperidine-1-carboxylic acid tert-butyl ester, 3a, the title compound 3-bromo-10-(1-methylpiperidin-4-yl)-10H-phenothiazine, 4e was obtained. MS m/z (MH$^+$) 375.1/377.1.

Procedure 15

3-Bromo-10-piperidin-4-yl-10H-phenothiazine, 5e

To a solution of 3-bromo-10-(1-methylpiperidin-4-yl)-10H-phenothiazine, 4e (0.6 g, 1.6 mmol) in 1,2-dichloroethane (10 mL) was added 1-chloroethyl chloroformate (276 μL, 2.6 mmol). The mixture was heated to reflux for 1 h, allowed to cool to rt, and evaporated. The residue was dissolved in methanol (10 mL) and heated to reflux for 1 h. Treatment with 1-chloroethyl chloroformate was repeated three more times to obtain ⅔ conversion. After work-up, the residue was purified via flash column chromatography (eluent gradient: 0 to 30% MeOH in EtOAc containing 1% triethylamine) to yield 150 mg of recovered starting material 4e and 382 mg (66%) of title compound 3-bromo-10-piperidin-4-yl-10H-phenothiazine, 5e. MS m/z (MH$^+$) 401.1/403.1.

Procedure 16

10-Piperidin-4-yl-3-pyridin-3-yl-10H-phenothiazine, 6e

A mixture of 3-bromo-10-piperidin-4-yl-10H-phenothiazine, 5e (10.5 mg, 0.029 mmol), 3-pyridyl boronic acid (10.7 mg, 0.087 mmol), potassium carbonate (12 mg, 0.087 mmol) and Pd(PPh$_3$)$_4$ (3 mg, 2.5 μmol) in NMP (300 μL) was heated to 160° C. for 10 min in a microwave. The mixture was absorbed onto a 1 g SPE cartridge and eluted (eluent: 10% methanol in ethyl acetate containing 1% triethylamine). The eluent (~15 mL) was collected and evaporated. The residue was purified via reverse phase HPLC (eluent: acetonitrile in water containing 0.1% TFA) to yield title compound 10-piperidin-4-yl-3-pyridin-3-yl-10H-phenothiazine, 6e as a TFA salt. MS m/z (MH$^+$) 360.2.

Example F

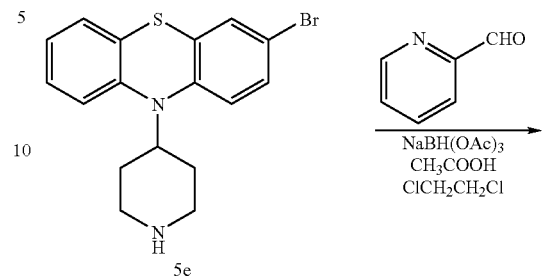

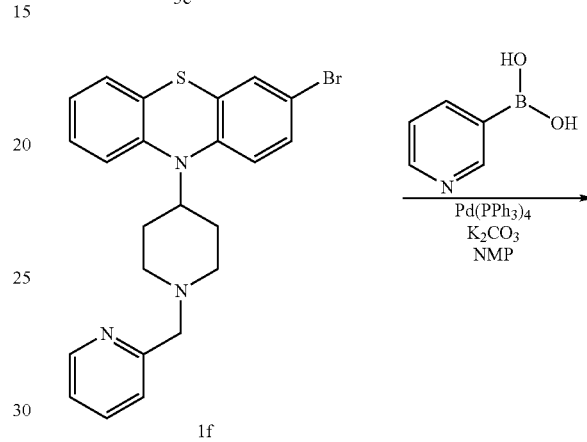

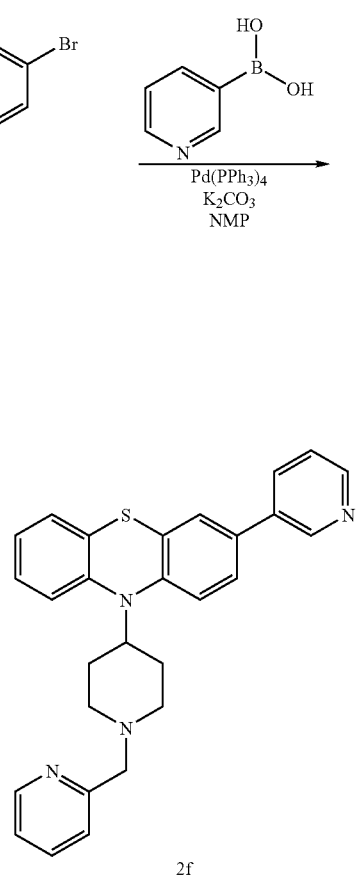

Procedure 17

3-Bromo-10-(1-pyridin-2-ylmethyl-piperidin-4-yl)-10H-phenothiazine, 1f

To a solution of 3-bromo-10-piperidin-4-yl-10H-phenothiazine, 5e (10.5 mg; 0.029 mmol) and 2-pyridyl carboxaldehyde (9.3 mg; 0.087 mmol) in dichloroethane (120 μL) was added acetic acid (5 μL) and a solution of sodium triacetoxyborohydride (12 mg, 0.057 mmol) in DMF (100 μL). The mixture was stirred at rt for 18 h, quenched with water (50 μL), and lyophilized. The thus obtained crude 3-bromo-10-(1-pyridin-2-ylmethyl-piperidin-4-yl)-10H-phenothiazine, 1f was used as such for the next reaction.

3-Pyridin-3-yl-10-(1-pyridin-2-ylmethyl-piperidin-4-yl)-10H-phenothiazine, 2f Using an adaptation of the method described in Procedure 16, substituting 3-bromo-10-(1-pyridin-2-ylmethyl-piperidin-4-yl)-10H-phenothiazine, 1f for 3-bromo-10-piperidin-4-yl-10H-phenothiazine, 5e, the title compound 3-pyridin-3-yl-10-(1-pyridin-2-ylmethyl-piperidin-4-yl)-10H-phenothiazine, 2f was obtained as a TFA salt. MS m/z (MH$^+$) 451.2.

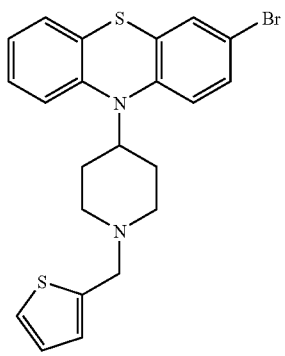

3-Bromo-10-(1-thiophen-2-ylmethyl-piperidin-4-yl)-10H-phenothiazine, 3f

Using an adaptation of the method described in Procedure 17, substituting 2-thiophene carboxaldehyde for 2-pyridyl carboxaldehyde and without adding acetic acid, the title compound 3-bromo-10-(1-thiophen-2-ylmethyl-piperidin-4-yl)-10H-phenothiazine, 3f was obtained. MS m/z (MH$^+$) 441.0.

3-Bromo-10-(1-phenethyl-piperidin-4-yl)-10H-phenothiazine, 4f

Using an adaptation of the method described in Procedure 17, substituting phenyl acetaldehyde for 2-pyridyl carboxaldehyde and without adding acetic acid, the title compound 3-bromo-10-(1-phenethyl-piperidin-4-yl)-10H-phenothiazine, 4f was obtained. MS m/z (MH$^+$) 465.1.

Example G

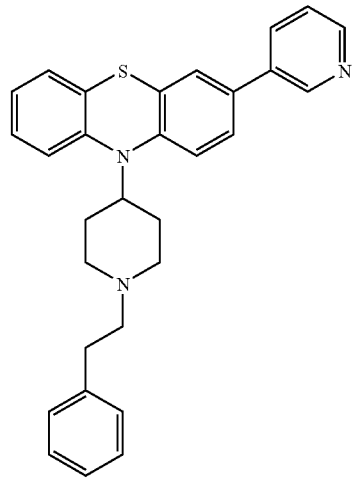

10-(1-Phenethyl-piperidin-4-yl)-3-pyridin-3-yl-10H-phenothiazine, 1g

Using an adaptation of the method described in Procedure 16, substituting 3-bromo-10-(1-phenethyl-piperidin-4-yl)-10H-phenothiazine, 4f for 3-bromo-10-piperidin-4-yl-10H-phenothiazine, 5e the title compound 10-(1-phenethyl-piperidin-4-yl)-3-pyridin-3-yl-10H-phenothiazine, 1g was obtained as a TFA salt. MS m/z (MH$^+$) 464.2.

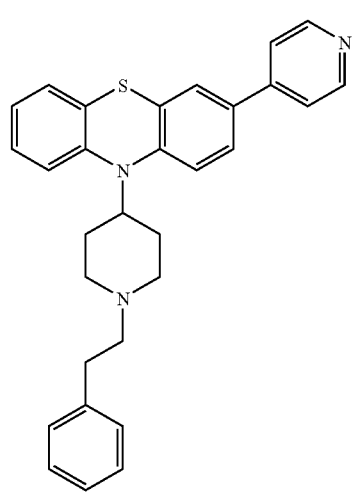

10-(1-Phenethyl-piperidin-4-yl)-3-pyridin-4-yl-10H-phenothiazine, 2g

Using an adaptation of the method described in Procedure 16, substituting 3-bromo-10-(1-phenethyl-piperidin-4-yl)-

10H-phenothiazine, 4f for 3-bromo-10-piperidin-4-yl-10H-phenothiazine, 5e and 4-pyridyl boronic acid for 3-pyridyl boronic acid in Procedure 16, the title compound 10-(1-phenethyl-piperidin-4-yl)-3-pyridin-4-yl-10H-phenothiazine, 2g was obtained as a TFA salt. MS m/z (MH$^+$) 464.2.

phenothiazine, 4e for 3-bromo-10-piperidin-4-yl-10H-phenothiazine, 5e and 2-acetylaminophenyl boronic acid for 3-pyridyl boronic acid, the title compound N-{2-[10-(1-methyl-piperidin-4-yl)-10H-phenothiazin-3-yl]-phenyl}-acetamide, 4g was obtained as a TFA salt. MS m/z (MH$^+$) 430.2.

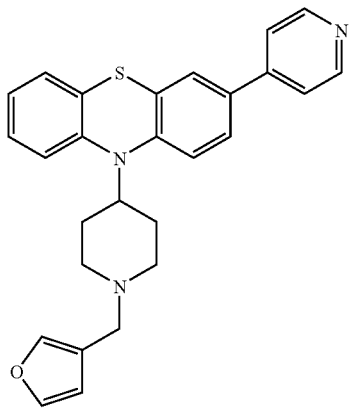

10-(1-Furan-3-ylmethyl-piperidin-4-yl)-3-pyridin-4-yl-10H-phenothiazine, 3g

Using an adaptation of the methods described in Procedures 16 and 17, substituting 3-furyl carboxaldehyde for 2-pyridyl carboxaldehyde in Procedure 17, and 4-pyridyl boronic acid for 3-pyridyl boronic acid in Procedure 16, the title compound 10-(1-furan-3-ylmethyl-piperidin-4-yl)-3-pyridin-4-yl-10H-phenothiazine, 3g was obtained as a TFA salt. MS m/z (MH$^+$) 440.2.

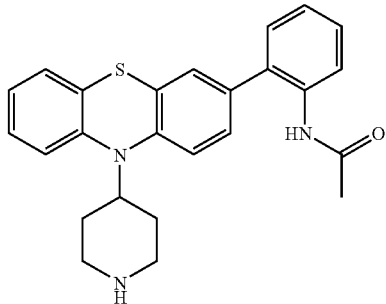

N-[2-(10-Piperidin-4-yl-10H-phenothiazin-3-yl)-phenyl]-acetamide, 5g

Using an adaptation of the method described in Procedure 16, substituting 2-acetylaminophenyl boronic acid for 3-pyridyl boronic acid, the title compound N-[2-(10-piperidin-4-yl-10H-phenothiazin-3-yl)-phenyl]-acetamide, 5g was obtained as a TFA salt. MS m/z (MH$^+$) 416.2.

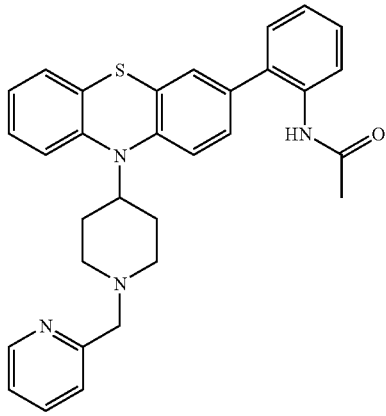

N-{2-[10-(1-Pyridin-2-ylmethyl-piperidin-4-yl)-10H-phenothiazin-3-yl]-phenyl}-acetamide, 6g Using an adaptation of the methods described in Procedures 16 and 17, substituting 2-acetylaminophenyl boronic acid for 3-pyridyl boronic acid in Procedure 16, the title compound N-{2-[10-(1-pyridin-2-ylmethyl-piperidin-4-yl)-10H-phenothiazin-3-yl]-phenyl}-acetamide, 6g was obtained as a TFA salt. MS m/z (MH$^+$) 507.2.

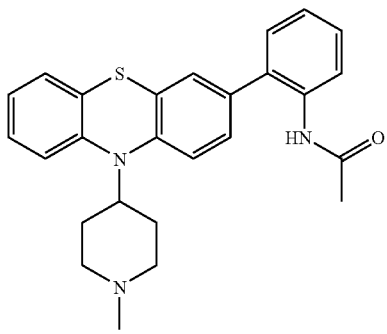

N-{2-[10-(1-Methyl-piperidin-4-yl)-10H-phenothiazin-3-yl]-phenyl}-acetamide, 4g

Using an adaptation of the method described in Procedure 16, substituting 3-bromo-10-(1-methylpiperidin-4-yl)-10H-

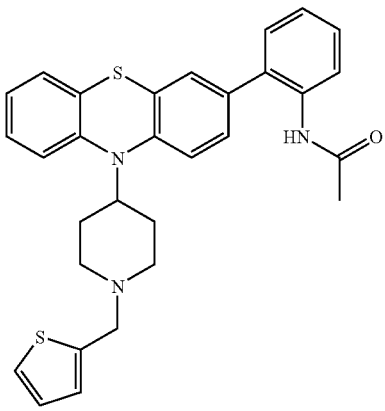

N-{2-[10-(1-Thiophen-2-ylmethyl-piperidin-4-yl)-10H-phenothiazin-3-yl]-phenyl}-acetamide, 7g Using an adaptation of the methods described in Procedures 16 and 17, substituting 2-thiophene carboxaldehyde for 2-pyridyl carboxaldehyde in Procedure 17 and 2-acetylaminophenyl boronic acid for 3-pyridyl boronic acid in Procedure 16, the title compound N-{2-[10-(1-thiophen-2-ylmethyl-piperidin-4-yl)-10H-phenothiazin-3-yl]-phenyl}-acetamide, 7g was obtained as a TFA salt. MS m/z (MH$^+$) 512.2.

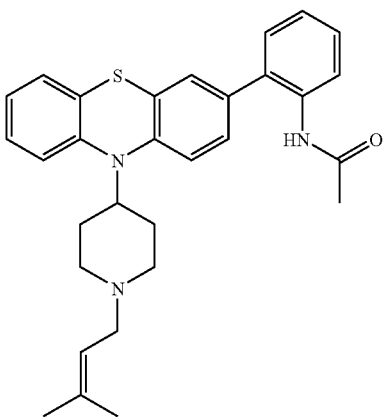

N-(2-{10-[1-(3-Methyl-but-2-enyl)-piperidin-4-yl]-10H-phenothiazin-3-yl}-phenyl)-acetamide, 8g Using an adaptation of the methods described in Procedures 16 and 17, substituting 3-methyl-but-2-enal for 2-pyridyl carboxaldehyde in Procedure 17 and 2-acetylaminophenyl boronic acid for 3-pyridyl boronic acid in Procedure 16, the title compound N-(2-{10-[1-(3-methyl-but-2-enyl)-piperidin-4-yl]-10H-phenothiazin-3-yl}-phenyl)-acetamide, 8g was obtained as a TFA salt. MS m/z (MH$^+$) 484.3.

Example H

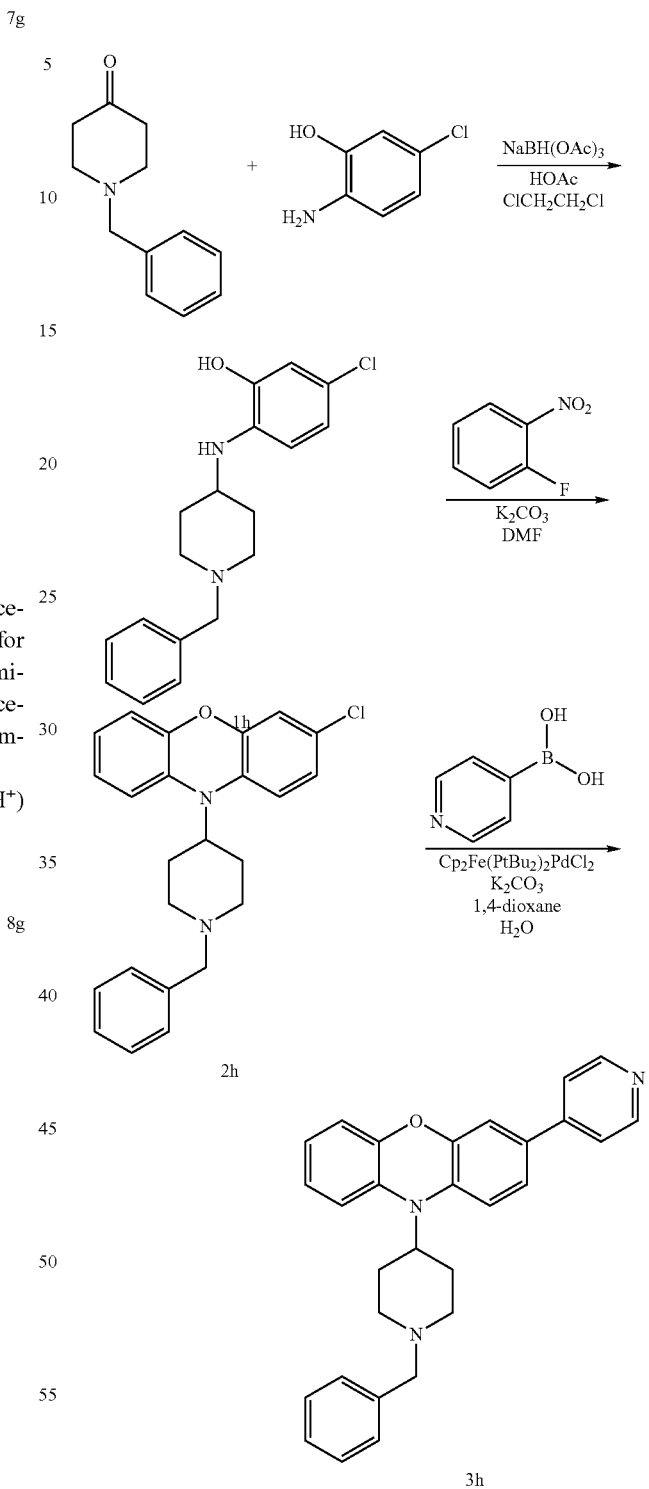

2-(1-Benzyl-piperidin-4-ylamino)-5-chlorophenol, 1h

Using an adaptation of the method described in Procedure 7, substituting 2-amino-5-chlorophenol for the TFA salt of 10-piperidin-4-yl-3-(1H-tetrazol-5-yl)-10H-phenoxazine, 6a, 1-benzyl-piperidin-4-one for 1H-imidazole-2-carboxaldehyde, and sodium triacetoxyborohydride for tetramethylammonium triacetoxyborohydride, the title compound 2-(1-benzyl-piperidin-4-ylamino)-5-chlorophenol, 1h was obtained. MS m/z (MH+) 317.

10-(1-Benzyl-piperidin-4-yl)-3-chloro-10H-phenoxazine, 2h

Using an adaptation of the method described in Procedure 1, substituting 2-(1-benzyl-piperidin-4-ylamino)-5-chlorophenol, 1h, for 2-bromophenol, and 2-fluoronitrobenzene for 3-fluoro-4-nitrobenzonitrile, the title compound 10-(1-benzyl-piperidin-4-yl)-3-chloro-10H-phenoxazine, 2h was obtained. MS m/z (MH+) 390.9.

10-(1-Benzyl-piperidin-4-yl)-3-pyridin-4-yl-10H-phenoxazine, 3h

Using an adaptation of the method described in Procedure 16, substituting 10-(1-benzyl-piperidin-4-yl)-3-chloro-10H-phenoxazine, 2h, for 3-bromo-10-piperidin-4-yl-10H-phenothiazine, 5e, 4-pyridyl boronic acid for 3-pyridyl boronic acid, $Cp_2Fe(PtBu_2)_2PdCl_2$ for $Pd(PPh_3)_4$ and a 5:1 mixture of dioxane:water for NMP, the title compound 10-(1-benzyl-piperidin-4-yl)-3-pyridin-4-yl-10H-phenoxazine, 3h was obtained as a TFA salt after reverse phase HPLC purification (eluent gradient: 10% to 30% $CH_3CN$ in water containing 0.1% TFA). MS m/z (MH+) 434.1.

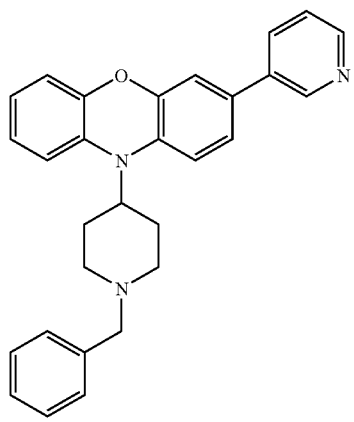

10-(1-Benzyl-piperidin-4-yl)-3-pyridin-3-yl-10H-phenoxazine, 4h

Using an adaptation of the method described in Procedure 16, substituting 10-(1-benzyl-piperidin-4-yl)-3-chloro-10H-phenoxazine, 2h, for 3-bromo-10-piperidin-4-yl-10H-phenothiazine, 5e, $Cp_2Fe(PtBu_2)_2PdCl_2$ for $Pd(PPh_3)_4$ and a 5:1 mixture of dioxane:water for NMP, the title compound 10-(1-benzyl-piperidin-4-yl)-3-pyridin-4-yl-10H-phenoxazine, 3h was obtained as a TFA salt after reverse phase HPLC purification (eluent gradient: 10% to 30% $CH_3CN$ in water containing 0.1% TFA). MS m/z (MH+) 434.1.

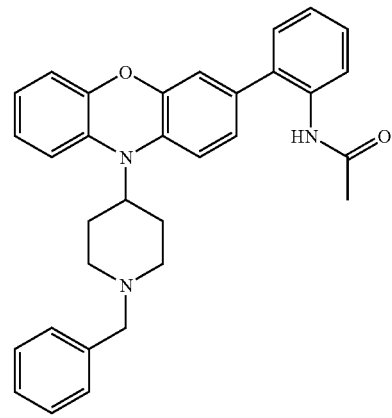

N-{2-[10-(1-Benzyl-piperidin-4-yl)-10H-phenoxazin-3-yl]-phenyl}-acetamide, 5h Using an adaptation of the method described in Procedure 16, substituting 10-(1-benzyl-piperidin-4-yl)-3-chloro-10H-phenoxazine, 2h, for 3-bromo-10-piperidin-4-yl-10H-phenothiazine, 5e, 2-acetylaminophenyl boronic acid for 3-pyridyl boronic acid, $Cp_2Fe(PtBu_2)_2PdCl_2$ for $Pd(PPh_3)_4$ and a 5:1 mixture of dioxane:water for NMP, the title compound N-{2-[10-(1-benzyl-piperidin-4-yl)-10H-phenoxazin-3-yl]-phenyl}-acetamide, 5h was obtained as a TFA salt after reverse phase HPLC purification (eluent gradient: 20% to 40% $CH_3CN$ in water containing 0.1% TFA). MS m/z (MH+) 490.2.

Example I

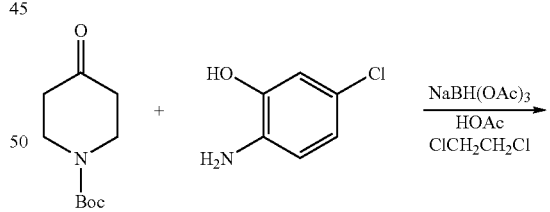

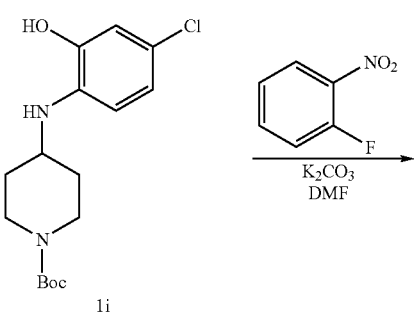

-continued

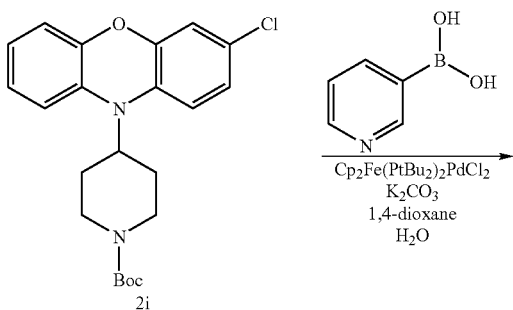

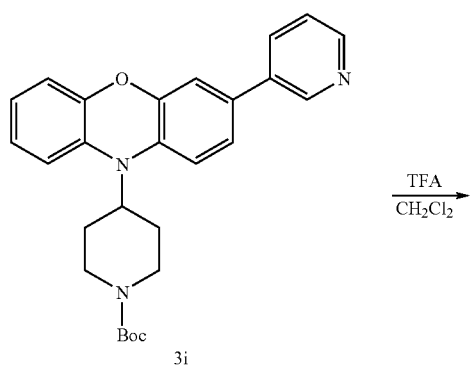

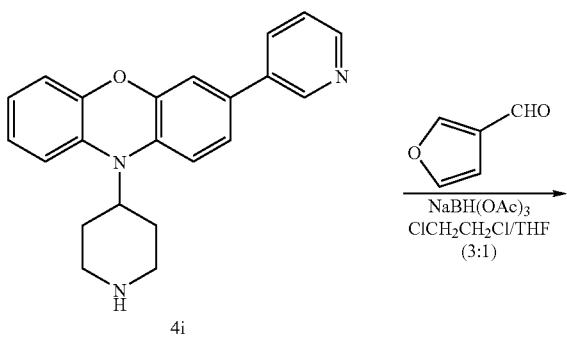

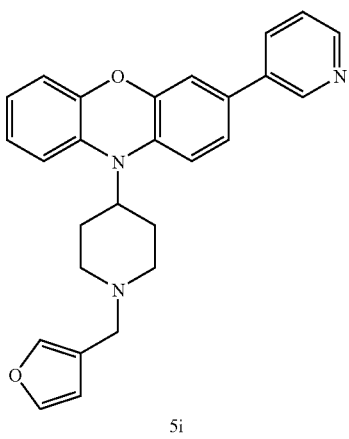

4-(4-Chloro-2-hydroxyphenylamino)-piperidine-1-carboxylic acid tert-butyl ester, 1i Using an adaptation of the method described in Procedure 7, substituting 2-amino-5-chlorophenol for the TFA salt of 10-piperidin-4-yl-3-(1H-tetrazol-5-yl)-10H-phenoxazine, 6a, and 4-oxo-piperidine-1-carboxylic acid tert-butyl ester for 1H-imidazole-2-carboxaldehyde, the title compound 4-(4-chloro-2-hydroxy-phenylamino)-piperidine-1-carboxylic acid tert-butyl ester, 1i was obtained. MS m/z (MH$^+$) 327.

4-(3-Chloro-phenoxazin-10-yl)-piperidine-1-carboxylic acid tert-butyl ester, 2i Using an adaptation of the method described in Procedure 1, substituting 4-(4-chloro-2-hydroxyphenylamino)-piperidine-1-carboxylic acid tert-butyl ester, 1i, for 2-bromophenol, and 2-fluoronitrobenzene for 3-fluoro-4-nitrobenzonitrile, the title compound 4-(3-chloro-phenoxazin-10-yl)-piperidine-1-carboxylic acid tert-butyl ester, 2i was obtained. MS m/z (MH$^+$) 401.

4-(3-Pyridin-3-yl-phenoxazin-10-yl)-piperidine-1-carboxylic acid tert-butyl ester, 3i Using an adaptation of the method described in Procedure 16, substituting 4-(3-chloro-phenoxazin-10-yl)-piperidine-1-carboxylic acid tert-butyl ester, 2i, for 3-bromo-10-piperidin-4-yl-10H-phenothiazine, 5e, Cp$_2$Fe(PtBu$_2$)$_2$PdCl$_2$ for Pd(PPh$_3$)$_4$ and a 5:1 mixture of dioxane:water for NMP, the title compound 4-(3-pyridin-3-yl-phenoxazin-10-yl)-piperidine-1-carboxylic acid tert-butyl ester, 3i was obtained. MS m/z (MH$^+$) 444.

10-Piperidin-4-yl-3-pyridin-3-yl-10H-phenoxazine, 4i

Using an adaptation of the method described in Procedure 6, substituting 4-(3-pyridin-3-yl-phenoxazin-10-yl)-piperidine-1-carboxylic acid tert-butyl ester, 3i, for 4-[3-(1H-tetrazol-5-yl)-phenoxazin-10-yl]-piperidine-1-carboxylic acid tert-butyl ester, 5a, and a mixture of TFA in methylene chloride for a 4N hydrochloric acid solution, the title compound 10-piperidin-4-yl-3-pyridin-3-yl-10H-phenoxazine, 4i was obtained as a TFA salt after purification via reverse phase HPLC (eluent gradient: CH$_3$CN in water containing 0.1% TFA). MS m/z (MH$^+$) 344.

10-(1-Furan-3-ylmethyl-piperidin-4-yl)-3-pyridin-3-yl-10H-phenoxazine, 5i

Using an adaptation of the method described in Procedure 7, substituting 10-piperidin-4-yl-3-pyridin-3-yl-10H-phenoxazine, 4i for the TFA salt of 10-piperidin-4-yl-3-(1H-tetrazol-5-yl)-10H-phenoxazine, 6a, 3-furyl carboxaldehyde for 1H-imidazole-2-carboxaldehyde, sodium triacetoxyborohydride for tetramethyl-ammonium triacetoxyborohydride, and a 3:1 mixture of 1,2-dichloroethane:THF for 100% 1,2-dichloroethane, the title compound 10-(1-furan-3-ylmethyl-piperidin-4-yl)-3-pyridin-3-yl-10H-phenoxazine, 5i was obtained as a TFA salt after purification via reverse phase HPLC (eluent: CH$_3$CN in H$_2$O containing 0.1% TFA). MS m/z (MH$^+$) 424.

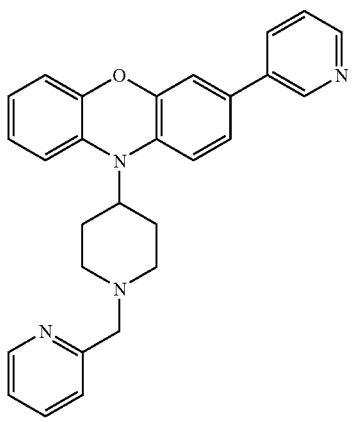

3-Pyridin-3-yl-10-(1-pyridin-2-ylmethyl-piperidin-4-yl)-10H-phenoxazine, 6i

Using an adaptation of the method described in Procedure 7, substituting 10-piperidin-4-yl-3-pyridin-3-yl-10H-phenoxazine, 4i for the TFA salt of 10-piperidin-4-yl-3-(1H-tetrazol-5-yl)-10H-phenoxazine, 6a, 2-pyridyl carboxaldehyde for 1H-imidazole-2-carboxaldehyde, sodium triacetoxyborohydride for tetramethyl-ammonium triacetoxyborohydride, and a 3:1 mixture of 1,2-dichloroethane:THF for 100% 1,2-dichloroethane, the title compound 3-pyridin-3-yl-10-(1-pyridin-2-ylmethyl-piperidin-4-yl)-10H-phenoxazine, 6i was obtained as a TFA salt after purification via reverse phase HPLC (eluent: CH$_3$CN in H$_2$O containing 0.1% TFA). MS m/z (MH$^+$) 435.

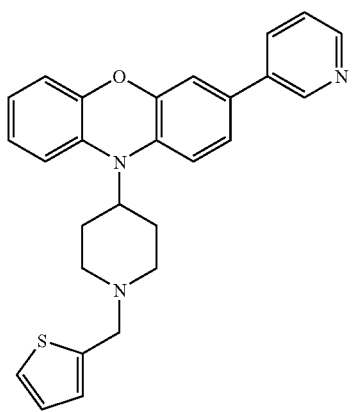

3-Pyridin-3-yl-10-(1-thiophen-2-ylmethyl-piperidin-4-yl)-10H-phenoxazine, 7i

Using an adaptation of the method described in Procedure 7, substituting 10-piperidin-4-yl-3-pyridin-3-yl-10H-phenoxazine, 4i for the TFA salt of 10-piperidin-4-yl-3-(1H-tetrazol-5-yl)-10H-phenoxazine, 6a, 2-thiophene carboxaldehyde for 1H-imidazole-2-carboxaldehyde, sodium triacetoxyborohydride for tetramethyl-ammonium triacetoxyborohydride, and a 3:1 mixture of 1,2-dichloroethane:THF for 100% 1,2-dichloroethane, the title compound 3-pyridin-3-yl-10-(1-thiophen-2-ylmethyl-piperidin-4-yl)-10H-phenoxazine, 7i was obtained as a TFA salt after purification via reverse phase HPLC (eluent: CH$_3$CN in H$_2$O containing 0.1% TFA). MS m/z (MH$^+$) 440.

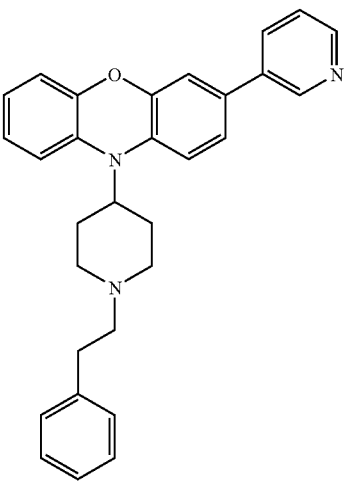

10-(1-Phenethyl-piperidin-4-yl)-3-pyridin-3-yl-10H-phenoxazine, 8i

Using an adaptation of the method described in Procedure 7, substituting 10-piperidin-4-yl-3-pyridin-3-yl-10H-phenoxazine, 4i for the TFA salt of 10-piperidin-4-yl-3-(1H-tetrazol-5-yl)-10H-phenoxazine, 6a, phenyl acetaldehyde for 1H-imidazole-2-carboxaldehyde, sodium triacetoxyborohydride for tetramethyl-ammonium triacetoxyborohydride, and a 3:1 mixture of 1,2-dichloroethane:THF for 100% 1,2-dichloroethane, the title compound 10-(1-phenethyl-piperidin-4-yl)-3-pyridin-3-yl-10H-phenoxazine, 8i was obtained as a TFA salt after purification via reverse phase HPLC (eluent: CH$_3$CN in H$_2$O containing 0.1% TFA). MS m/z (MH$^+$) 448.

Example J

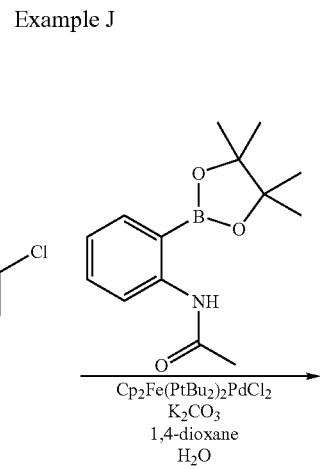

-continued

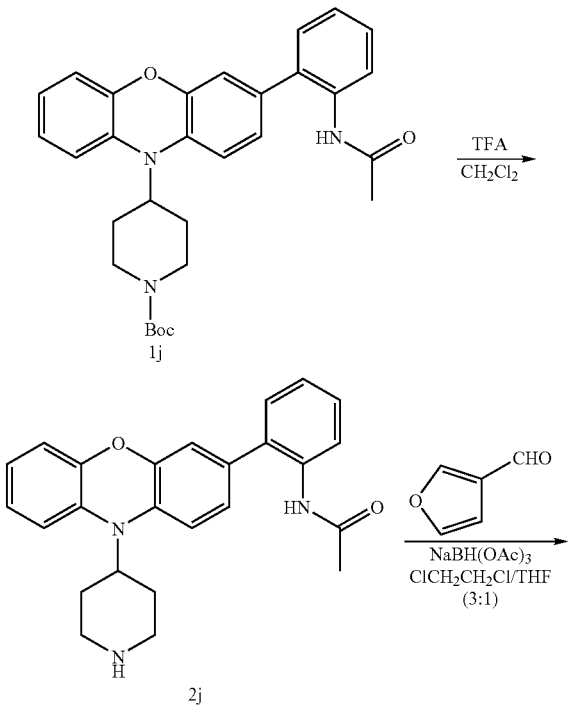

N-[2-(10-Piperidin-4-yl-10H-phenoxazin-3-yl)-phenyl]-acetamide, 2j

Using an adaptation of the method described in Procedure 6, substituting 4-[3-(2-acetylaminophenyl)-phenoxazin-10-yl]-piperidine-1-carboxylic acid tert-butyl ester, 1j, for 4-[3-(1H-tetrazol-5-yl)-phenoxazin-10-yl]-piperidine-1-carboxylic acid tert-butyl ester, 5a, and a mixture of TFA in methylene chloride for a 4N hydrochloric acid solution, the title compound N-[2-(10-piperidin-4-yl-10H-phenoxazin-3-yl)-phenyl]-acetamide, 2j was obtained as a TFA salt after purification via reverse phase HPLC (eluent gradient: $CH_3CN$ in water containing 0.1% TFA). MS m/z ($MH^+$) 400.

N-{2-[10-(1-Furan-3-ylmethyl-piperidin-4-yl)-10H-phenoxazin-3-yl]-phenyl}-acetamide, 3j Using an adaptation of the method described in Procedure 7, substituting N-[2-(10-piperidin-4-yl-10H-phenoxazin-3-yl)-phenyl]-acetamide, 2j for the TFA salt of 10-piperidin-4-yl-3-(1H-tetrazol-5-yl)-10H-phenoxazine, 6a, 3-furaldehyde for 1H-imidazole-2-carboxaldehyde, sodium triacetoxyborohydride for tetramethylammonium borohydride, and a 3:1 mixture of 1,2-dichloroethane:THF for 100% 1,2-dichloroethane, the title compound N-{2-[10-(1-furan-3-ylmethyl-piperidin-4-yl)-10H-phenoxazin-3-yl]-phenyl}-acetamide, 3j was obtained as a TFA salt after purification via reverse phase HPLC (eluent: $CH_3CN$ in $H_2O$ containing 0.1% TFA). MS m/z ($MH^+$) 480.

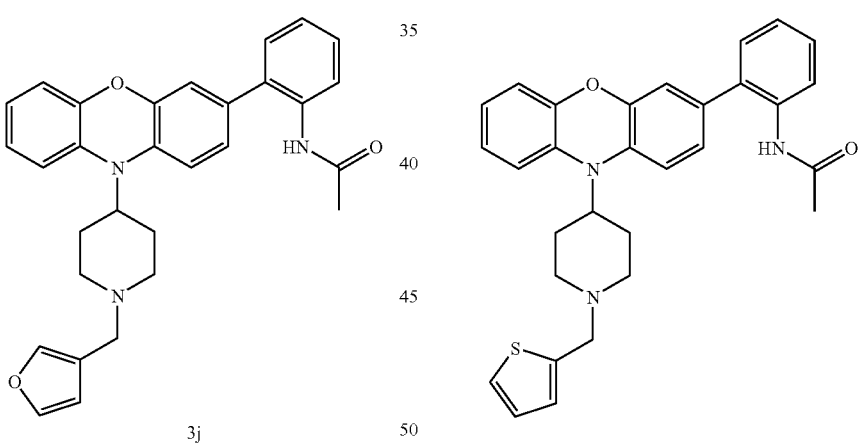

4-[3-(2-Acetylaminophenyl)-phenoxazin-10-yl]-piperidine-1-carboxylic acid tert-butyl ester, 1j Using an adaptation of the method described in Procedure 16, substituting 4-(3-chloro-phenoxazin-10-yl)-piperidine-1-carboxylic acid tert-butyl ester, 2i, for 3-bromo-10-piperidin-4-yl-10H-phenothiazine, 5e, N-[2-(4,4,5,5-tetramethyl-[1,3,2]dioxaborolan-2-yl)-phenyl]-acetamide for 3-pyridyl boronic acid, $Cp_2Fe(PtBu_2)_2PdCl_2$ for $Pd(PPh_3)_4$ and a 5:1 mixture of dioxane:water for NMP, the title compound 4-[3-(2-acetylaminophenyl)-phenoxazin-10-yl]-piperidine-1-carboxylic acid tert-butyl ester, 1j was obtained.

N-{2-[10-(1-Thiophen-2-ylmethyl-piperidin-4-yl)-10H-phenoxazin-3-yl]-phenyl}-acetamide, 4j Using an adaptation of the method described in Procedure 7, substituting N-[2-(10-piperidin-4-yl-10H-phenoxazin-3-yl)-phenyl]-acetamide, 2j for the TFA salt of 10-piperidin-4-yl-3-(1H-tetrazol-5-yl)-10H-phenoxazine, 6a, 2-thiophene carboxaldehyde for 1H-imidazole-2-carboxaldehyde, sodium triacetoxyborohydride for tetramethylammonium borohydride, and a 3:1 mixture of 1,2-dichloroethane:THF for 100% 1,2-dichloroethane, the title compound N-{2-[10-(1-furan-3-ylmethyl-piperidin-4-yl)-10H-phenoxazin-3-yl]-phenyl}-acetamide, 3j was obtained as a TFA salt after purification via reverse phase HPLC (eluent: $CH_3CN$ in $H_2O$ containing 0.1% TFA). MS m/z ($MH^+$) 496.

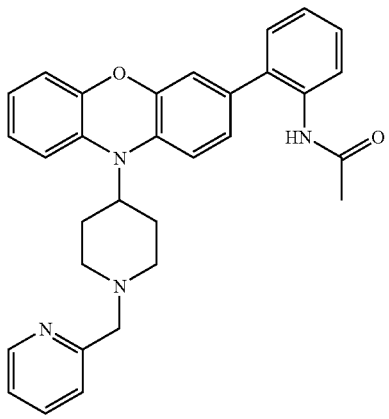

N-{2-[10-(1-Pyridin-2-ylmethyl-piperidin-4-yl)-10H-phenoxazin-3-yl]-phenyl}-acetamide, 5j Using an adaptation of the method described in Procedure 7, substituting N-[2-(10-piperidin-4-yl-10H-phenoxazin-3-yl)-phenyl]-acetamide, 2j for the TFA salt of 10-piperidin-4-yl-3-(1H-tetrazol-5-yl)-10H-phenoxazine, 6a, 2-pyridyl carboxaldehyde for 1H-imidazole-2-carboxaldehyde, sodium triacetoxyborohydride for tetramethylammonium borohydride, and a 3:1 mixture of 1,2-dichloroethane:THF for 100% 1,2-dichloroethane, the title compound N-{2-[10-(1-pyridin-2-ylmethyl-piperidin-4-yl)-10H-phenoxazin-3-yl]-phenyl}-acetamide, 5j was obtained as a TFA salt after purification via reverse phase HPLC (eluent: CH$_3$CN in H$_2$O containing 0.1% TFA). MS m/z (MH$^+$) 491.

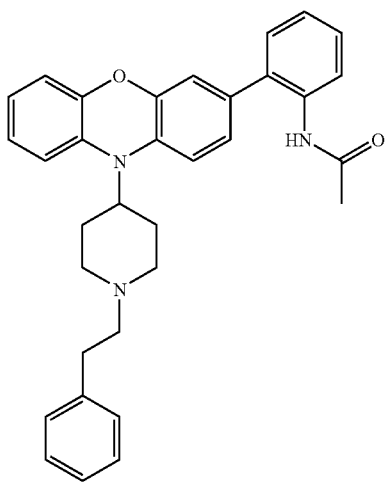

N-{2-[10-(1-Phenethyl-piperidin-4-yl)-10H-phenoxazin-3-yl]-phenyl}-acetamide, 6j Using an adaptation of the method described in Procedure 7, substituting N-[2-(10-piperidin-4-yl-10H-phenoxazin-3-yl)-phenyl]-acetamide, 2j for the TFA salt of 10-piperidin-4-yl-3-(1H-tetrazol-5-yl)-10H-phenoxazine, 6a, phenyl acetaldehyde for 1H-imidazole-2-carboxaldehyde, sodium triacetoxyborohydride for tetramethylammonium borohydride, and a 3:1 mixture of 1,2-dichloroethane:THF for 100% 1,2-dichloroethane, the title compound N-{2-[10-(1-phenethyl-piperidin-4-yl)-10H-phenoxazin-3-yl]-phenyl}-acetamide, 6j was obtained as a TFA salt after purification via reverse phase HPLC (eluent: CH$_3$CN in H$_2$O containing 0.1% TFA). MS m/z (MH$^+$) 504.

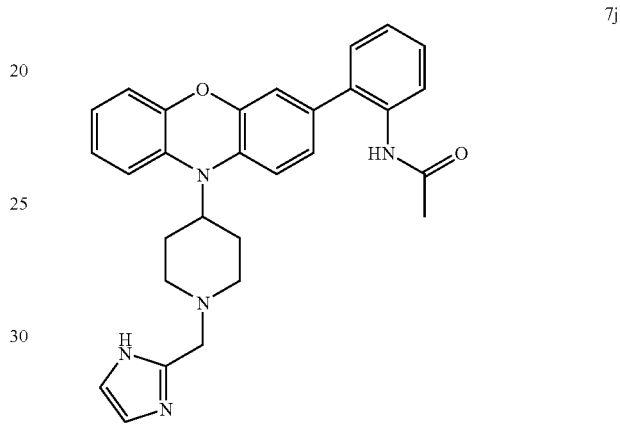

N-(2-{10-[1-(1H-Imidazol-2-ylmethyl)-piperidin-4-yl]-10H-phenoxazin-3-yl}-phenyl)-acetamide, 7j Using an adaptation of the method described in Procedure 7, substituting N-[2-(10-piperidin-4-yl-10H-phenoxazin-3-yl)-phenyl]-acetamide, 2j for the TFA salt of 10-piperidin-4-yl-3-(1H-tetrazol-5-yl)-10H-phenoxazine, 6a, sodium triacetoxyborohydride for tetramethylammonium borohydride, and a 3:1 mixture of 1,2-dichloroethane:THF for 100% 1,2-dichloroethane, the title compound N-(2-{10-[1-(1H-imidazol-2-ylmethyl)-piperidin-4-yl]-10H-phenoxazin-3-yl}-phenyl)-acetamide, 7j was obtained as a TFA salt after purification via reverse phase HPLC (eluent: CH$_3$CN in H$_2$O containing 0.1% TFA). MS m/z (MH$^+$) 479.9.

Example K

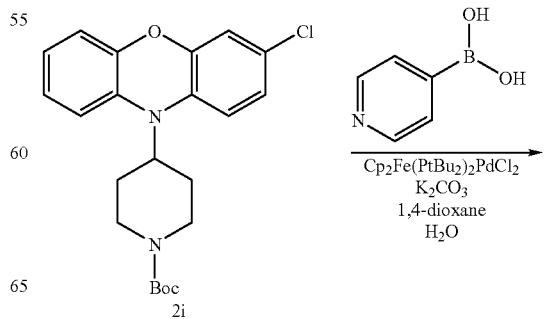

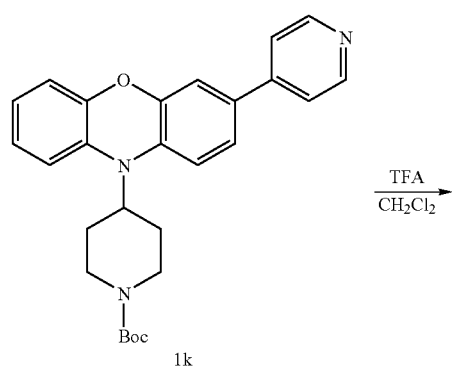

1k

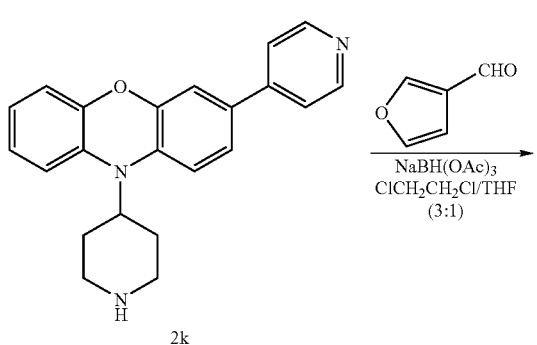

2k 4-(3-Pyridin-4-yl-phenoxazin-10-yl)-piperidine-1-carboxylic acid tert-butyl ester, 1k Using an adaptation of the method described in Procedure 16, substituting 4-(3-chloro-phenoxazin-10-yl)-piperidine-1-carboxylic acid tert-butyl ester, 2i, for 3-bromo-10-piperidin-4-yl-10H-phenothiazine, 5e, 4-pyridyl boronic acid for 3-pyridyl boronic acid, $Cp_2Fe(PtBu_2)_2PdCl_2$ for $Pd(PPh_3)_4$ and a 5:1 mixture of dioxane:water for NMP, the title compound 4-(3-pyridin-4-yl-phenoxazin-10-yl)-piperidine-1-carboxylic acid tert-butyl ester, 1k was obtained. MS m/z (MH$^+$) 444.

10-Piperidin-4-yl-3-pyridin-4-yl-10H-phenoxazine, 2k

Using an adaptation of the method described in Procedure 6, substituting 4-(3-pyridin-4-yl-phenoxazin-10-yl)-piperidine-1-carboxylic acid tert-butyl ester, 1k, for 4-[3-(1H-tetrazol-5-yl)-phenoxazin-10-yl]-piperidine-1-carboxylic acid tert-butyl ester, 5a, and a mixture of TFA in methylene chloride for a 4N hydrochloric acid solution, the title compound 10-piperidin-4-yl-3-pyridin-4-yl-10H-phenoxazine, 2k, was obtained as a TFA salt after purification via reverse phase HPLC (eluent gradient: $CH_3CN$ in water containing 0.1% TFA). MS m/z (MH$^+$) 344.

10-(1-Furan-3-ylmethyl-piperidin-4-yl)-3-pyridin-4-yl-10H-phenoxazine, 3k

Using an adaptation of the method described in Procedure 7, substituting 10-piperidin-4-yl-3-pyridin-4-yl-10H-phenoxazine, 2k for the TFA salt of 10-piperidin-4-yl-3-(1H-tetrazol-5-yl)-10H-phenoxazine, 6a, 3-furaldehyde for 1H-imidazole-2-carboxaldehyde, sodium triacetoxyborohydride for tetramethyl-ammonium borohydride, and a 3:1 mixture of 1,2-dichloroethane:THF for 100% 1,2-dichloroethane, the title compound 10-(1-furan-3-ylmethyl-piperidin-4-yl)-3-pyridin-4-yl-10H-phenoxazine, 3k was obtained as a TFA salt after purification via reverse phase HPLC (eluent: $CH_3CN$ in $H_2O$ containing 0.1% TFA). MS m/z (MH$^+$) 424.

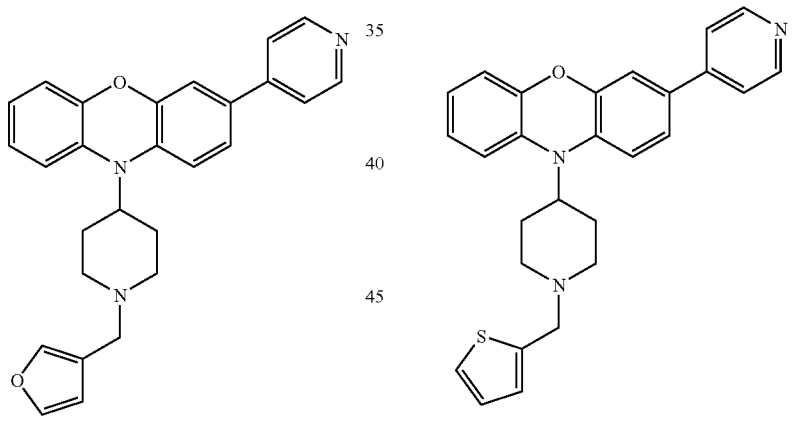

3-Pyridin-4-yl-10-(1-thiophen-2-ylmethyl-piperidin-4-yl)-10H-phenoxazine, 4k

Using an adaptation of the method described in Procedure 7, substituting 10-piperidin-4-yl-3-pyridin-4-yl-10H-phenoxazine, 2k for the TFA salt of 10-piperidin-4-yl-3-(1H-tetrazol-5-yl)-10H-phenoxazine, 6a, 2-thiophene carboxaldehyde for 1H-imidazole-2-carboxaldehyde, sodium triacetoxyborohydride for tetramethyl-ammonium borohydride, and a 3:1 mixture of 1,2-dichloroethane:THF for 100% 1,2-dichloroethane, the title compound 3-pyridin-4-yl-10-(1-thiophen-2-ylmethyl-piperidin-4-yl)-10H-phenoxazine, 4k was obtained as a TFA salt after purification via reverse phase HPLC (eluent: $CH_3CN$ in $H_2O$ containing 0.1% TFA). MS m/z (MH$^+$) 440.

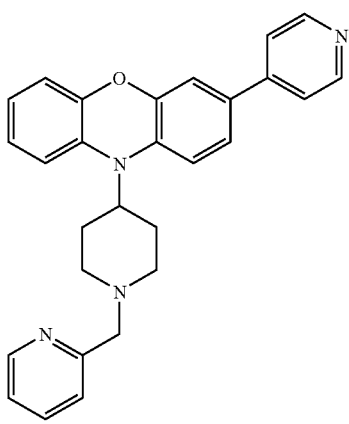

3-Pyridin-4-yl-10-(1-pyridin-2-ylmethyl-piperidin-4-yl)-10H-phenoxazine, 5k

Using an adaptation of the method described in Procedure 7, substituting 10-piperidin-4-yl-3-pyridin-4-yl-10H-phenoxazine, 2k for the TFA salt of 10-piperidin-4-yl-3-(1H-tetrazol-5-yl)-10H-phenoxazine, 6a, 2-pyridyl carboxaldehyde for 1H-imidazole-2-carboxaldehyde, sodium triacetoxyborohydride for tetramethyl-ammonium borohydride, and a 3:1 mixture of 1,2-dichloroethane:THF for 100% 1,2-dichloroethane, the title compound 3-pyridin-4-yl-10-(1-pyridin-2-ylmethyl-piperidin-4-yl)-10H-phenoxazine, 5k was obtained as a TFA salt after purification via reverse phase HPLC (eluent: $CH_3CN$ in $H_2O$ containing 0.1% TFA). MS m/z (MH$^+$) 435.

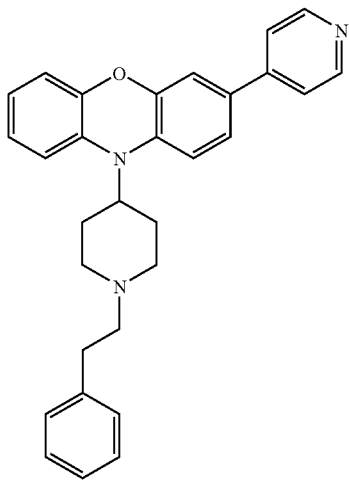

10-(1-Phenethyl-piperidin-4-yl)-3-pyridin-4-yl-10H-phenoxazine, 6k

Using an adaptation of the method described in Procedure 7, substituting 10-piperidin-4-yl-3-pyridin-4-yl-10H-phenoxazine, 2k for the TFA salt of 10-piperidin-4-yl-3-(1H-tetrazol-5-yl)-10H-phenoxazine, 6a, phenyl acetaldehyde for 1H-imidazole-2-carboxaldehyde, sodium triacetoxyborohydride for tetramethyl-ammonium borohydride, and a 3:1 mixture of 1,2-dichloroethane:THF for 100% 1,2-dichloroethane, the title compound 10-(1-phenethyl-piperidin-4-yl)-3-pyridin-4-yl-10H-phenoxazine, 6k was obtained as a TFA salt after purification via reverse phase HPLC (eluent: $CH_3CN$ in $H_2O$ containing 0.1% TFA). MS m/z (MH$^+$) 448.

Example L

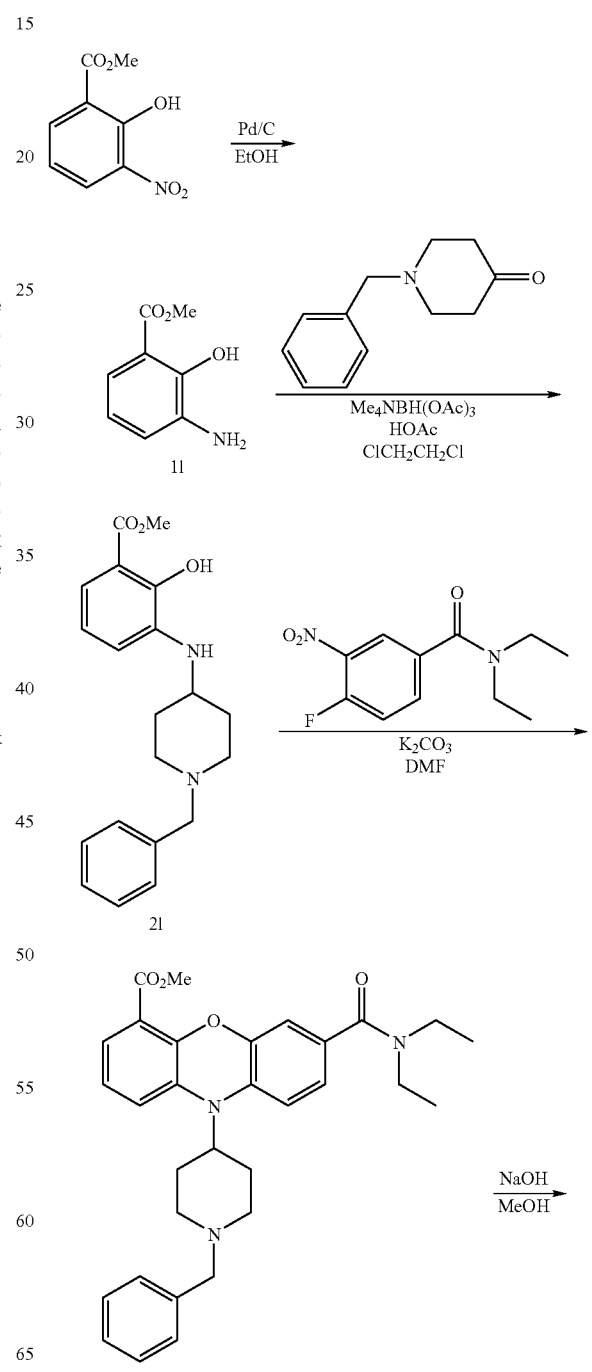

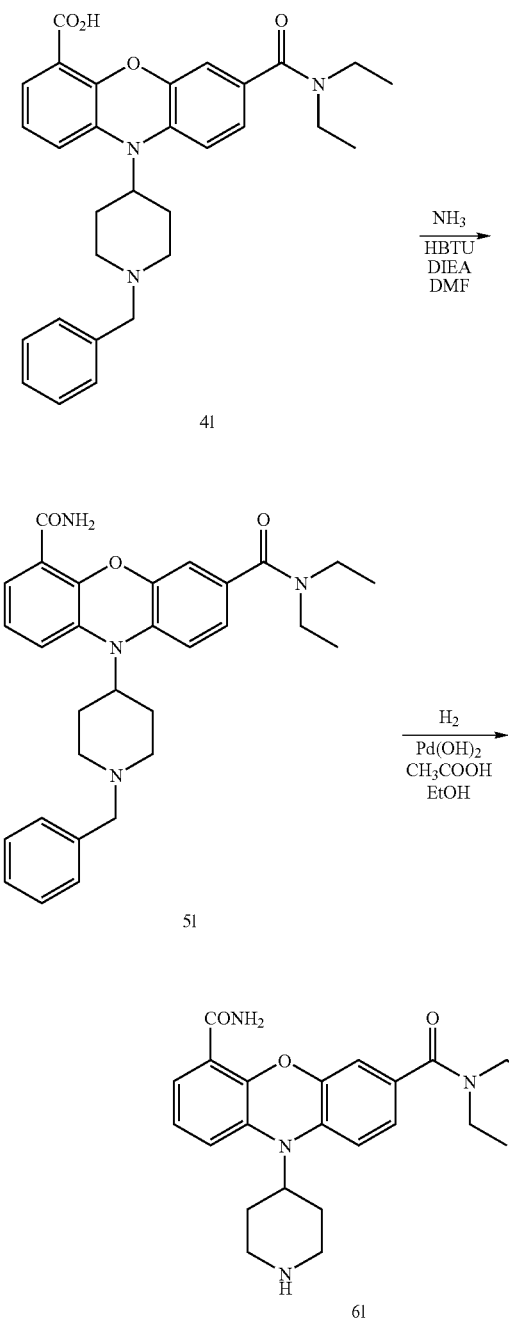

3-(1-Benzylpiperidin-4-ylamino)-2-hydroxybenzoic acid methyl ester, 2l

Using an adaptation of the method described in Procedure 3, substituting 3-amino-2-hydroxybenzoic acid methyl ester, 1l for 4-amino-3-(2-bromophenoxy)-benzonitrile, 2a, 1-benzylpiperidin-4-one for 4-oxo-piperidine-1-carboxylic acid tert-butyl ester, and tetramethylammonium triacetoxyborohydride for sodium triacetoxyborohydride, the title compound 3-(1-benzylpiperidin-4-ylamino)-2-hydroxybenzoic acid methyl ester, 2l was obtained.

10-(1-Benzylpiperidin-4-yl)-7-diethylcarbamoyl-10H-phenoxazine-4-carboxylic acid methyl ester, 3l Using an adaptation of the method described in Procedure 1, substituting 3-(1-benzylpiperidin-4-ylamino)-2-hydroxybenzoic acid methyl ester, 2l for 2-bromophenol, and N,N-diethyl-4-fluoro-3-nitrobenzamide for 3-fluoro-4-nitrobenzonitrile, the title compound 10-(1-benzylpiperidin-4-yl)-7-diethylcarbamoyl-10H-phenoxazine-4-carboxylic acid methyl ester, 3l was obtained.

Procedure 19

10-(1-Benzylpiperidin-4-yl)-7-diethylcarbamoyl-10H-phenoxazine-4-carboxylic acid, 4l To a solution of 10-(1-benzylpiperidin-4-yl)-7-diethylcarbamoyl-10H-phenoxazine-4-carboxylic acid methyl ester, 3l (2.92 g, 5.7 mmol) in methanol (10 mL) was added a 1N sodium hydroxide solution (5 mL), and the mixture was heated to 50° C. for 30 min. The mixture was allowed to cool to rt, the solvent was evaporated, and the residue was purified via reverse phase HPLC (eluent: $CH_3CN$ in water containing 0.1% TFA), yielding title compound 10-(1-benzylpiperidin-4-yl)-7-diethylcarbamoyl-10H-phenoxazine-4-carboxylic acid, 4l, as a TFA salt. MS m/z ($MH^+$) 500.1

10-(1-Benzylpiperidin-4-yl)-10H-phenoxazine-3,6-dicarboxylic acid 6-amide 3-diethylamide, 5l Using an adaptation of the method described in Procedure 12, substituting the TFA salt of 10-(1-benzylpiperidin-4-yl)-7-diethylcarbamoyl-10H-phenoxazine-4-carboxylic acid, 4l for 10-(1-benzyl-piperidin-4-yl)-6-methoxy-10H-phenoxazine-3-carboxylic acid, 3d, ammonia (0.5 M solution in dioxane) for N,N-diethylamine, and HBTU for HATU, the title compound 10-(1-benzylpiperidin-4-yl)-10H-phenoxazine-3,6-dicarboxylic acid 6-amide 3-diethylamide, 5l was obtained as a TFA salt after purification via reverse phase HPLC (eluent: $CH_3CN$ in water containing 0.1% TFA). MS m/z ($MH^+$) 499.1.

10-Piperidin-4-yl-10H-phenoxazine-3,6-dicarboxylic Acid 6-amide 3-diethylamide, 6l Using an adaptation of the method described in Procedure 18, substituting the TFA salt of 10-(1-benzylpiperidin-4-yl)-10H-phenoxazine-3,6-dicarboxylic acid 6-amide 3-diethylamide, 5l for 2-hydroxy-3-nitrobenzoic acid methyl ester, palladium hydroxide for palladium on carbon and in the presence of acetic acid, the title compound 10-piperidin-4-yl-10H-phenoxazine-3,6-dicarboxylic acid 6-amide 3-diethylamide, 6l was obtained as a TFA salt after purification via reverse phase HPLC (eluent: $CH_3CN$ in water containing 0.1% TFA). MS m/z ($MH^+$) 409.

Procedure 18

3-Amino-2-hydroxybenzoic acid methyl ester, 1l

To a solution of 2-hydroxy-3-nitrobenzoic acid methyl ester (5 g, 25.4 mmol) in ethanol (40 mL) was added 10% palladium on carbon (0.5 g), and the mixture was hydrogenated for 2 h. The catalyst was removed via filtration and the solvent was removed via evaporation, yielding 4.17 g (88%) of title compound 3-amino-2-hydroxybenzoic acid methyl ester, 1l.

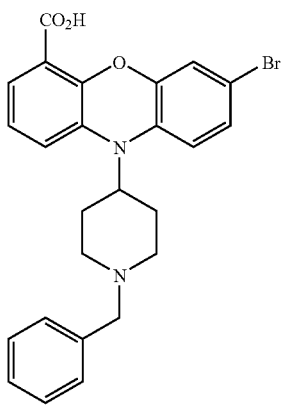

10-(1-Benzyl-piperidin-4-yl)-7-bromo-10H-phenoxazine-4-carboxylic acid, 7l

Using an adaptation of the method described in Procedures 1 and 19, substituting 3-(1-benzylpiperidin-4-ylamino)-2-hydroxybenzoic acid methyl ester, 2l for 2-bromophenol, 5-bromo-2-fluoro-nitrobenzene for 3-fluoro-4-nitrobenzonitrile, and dimethyl sulfoxide for dimethyl formamide in Procedure 1, and substituting dimethyl sulfoxide for metyhanol in Procedure 19, the title compound 10-(1-benzyl-piperidin-4-yl)-7-bromo-10H-phenoxazine-4-carboxylic acid, 7l was obtained as a TFA salt after purification via reverse phase HPLC (eluent: CH$_3$CN in water containing 0.1% TFA). MS m/z (MH$^+$) 478.9/480.

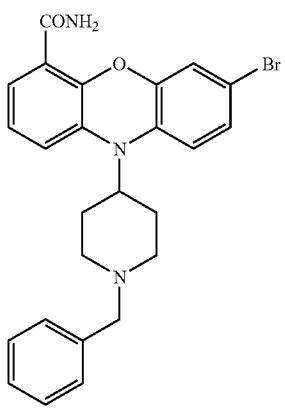

10-(1-Benzyl-piperidin-4-yl)-7-bromo-10H-phenoxazine-4-carboxylic acid amide, 8l Using an adaptation of the method described in Procedure 12, substituting the TFA salt of 10-(1-benzyl-piperidin-4-yl)-7-bromo-10H-phenoxazine-4-carboxylic acid, 7l for 10-(1-benzyl-piperidin-4-yl)-6-methoxy-10H-phenoxazine-3-carboxylic acid, 3d, ammonia (0.5 M solution in dioxane) for N,N-diethylamine, and HBTU for HATU, the title compound 10-(1-benzyl-piperidin-4-yl)-7-bromo-10H-phenoxazine-4-carboxylic acid amide, 8l was obtained as a TFA salt after purification via reverse phase HPLC (eluent: CH$_3$CN in water containing 0.1% TFA). MS m/z (MH$^+$) 477.6/479.

Example M

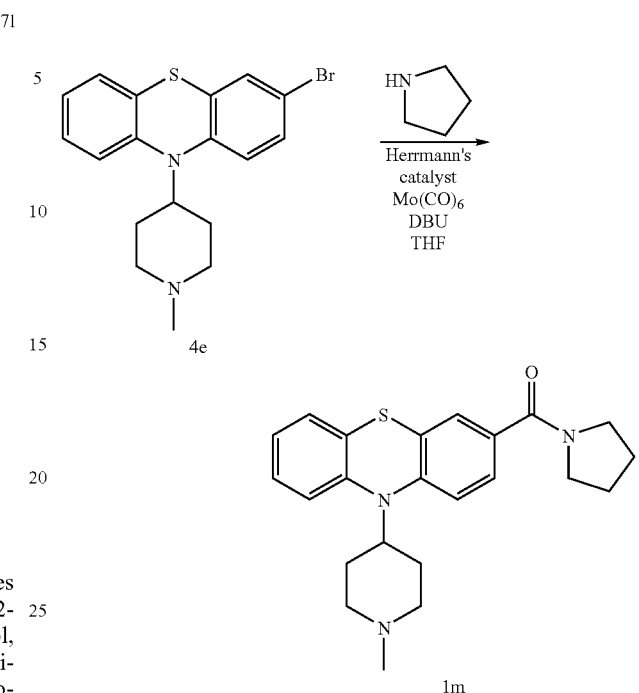

Procedure 20

[10-(1-Methyl-piperidin-4-yl)-10H-phenothiazin-3-yl]-pyrrolidin-1-yl-methanone, 1m To a solution of 3-bromo-10-(1-methylpiperidin-4-yl)-10H-phenothiazine, 4e (19 mg, 0.05 mmol) in THF (0.3 mL) was added pyrrolidine (12 µL, 0.15 mmol), Mo(CO)$_6$ (13 mg, 0.05 mmol), Herrmann's catalyst (2.3 mg, 0.0025 mmol), and DBU (22 µL, 0.15 mmol), and the mixture was irradiated in a microwave oven at 150° C. for 15 min. The mixture was evaporated, and the residue was purified via reverse phase HPLC (eluent gradient: CH$_3$CN in water containing 0.1% TFA) to yield [10-(1-methyl-piperidin-4-yl)-10H-phenothiazin-3-yl]-pyrrolidin-1-yl-methanone, 1m as a TFA salt. MS m/z (MH$^+$) 394.2.

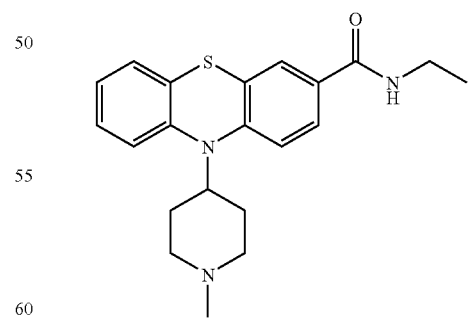

10-(1-Methyl-piperidin-4-yl)-10H-phenothiazine-3-carboxylic acid ethylamide, 2m

Using an adaptation of the method described in Procedure 20, substituting ethylamine for pyrrolidine, the title compound 10-(1-methyl-piperidin-4-yl)-10H-phenothiazine-3-carboxylic acid ethylamide, 2m was obtained as a TFA salt after purification via reverse phase HPLC (eluent: $CH_3CN$ in $H_2O$ containing 0.1% TFA). MS m/z ($MH^+$) 368.2.

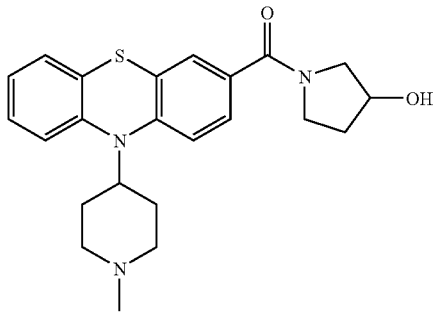

(3-Hydroxypyrrolidin-1-yl)-[10-(1-methylpiperidin-4-yl)-10H-phenothiazin-3-yl]-methanone, 3m Using an adaptation of the method described in Procedure 20, substituting 3-hydroxypyrrolidine for pyrrolidine, the title compound (3-hydroxypyrrolidin-1-yl)-[10-(1-methylpiperidin-4-yl)-10H-phenothiazin-3-yl]-methanone, 3m was obtained as a TFA salt after purification via reverse phase HPLC (eluent: $CH_3CN$ in $H_2O$ containing 0.1% TFA). MS m/z ($MH^+$) 410.2.

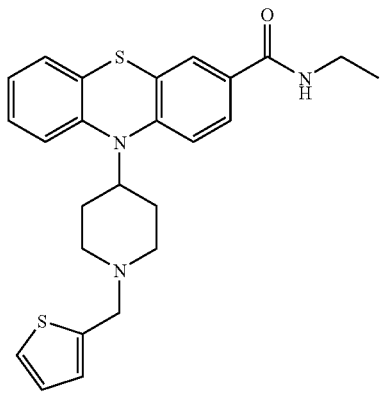

10-(1-Thiophen-2-ylmethyl-piperidin-4-yl)-10H-phenothiazine-3-carboxylic acid ethylamide, 4m Using an adaptation of the method described in Procedure 20, substituting 3-bromo-10-(1-thiophen-2-ylmethyl-piperidin-4-yl)-10H-phenothiazine, 3f for 3-bromo-10-(1-methylpiperidin-4-yl)-10H-phenothiazine, 4e and ethylamine for pyrrolidine, the title compound 10-(1-thiophen-2-ylmethyl-piperidin-4-yl)-10H-phenothiazine-3-carboxylic acid ethylamide, 4m was obtained as a TFA salt after purification via reverse phase HPLC (eluent: $CH_3CN$ in $H_2O$ containing 0.1% TFA). MS m/z ($MH^+$) 450.1.

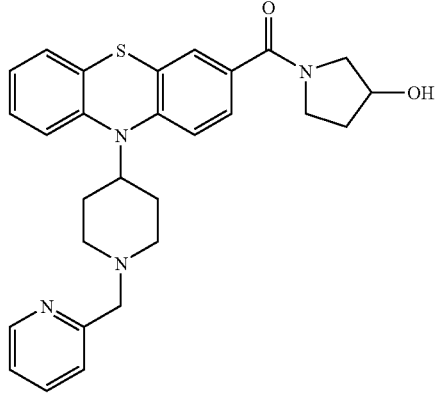

(3-Hydroxypyrrolidin-1-yl)-[10-(1-pyridin-2-ylmethyl-piperidin-4-yl)-10H-phenothiazin-3-yl]-methanone, 5m Using an adaptation of the method described in Procedure 20, substituting 3-bromo-10-(1-pyridin-2-ylmethyl-piperidin-4-yl)-10H-phenothiazine, 1f for 3-bromo-10-(1-methylpiperidin-4-yl)-10H-phenothiazine, 4e and 3-hydroxypyrrolidine for pyrrolidine, the title compound (3-hydroxypyrrolidin-1-yl)-[10-(1-pyridin-2-ylmethyl-piperidin-4-yl)-10H-phenothiazin-3-yl]-methanone, 5m was obtained as a TFA salt after purification via reverse phase HPLC (eluent: $CH_3CN$ in $H_2O$ containing 0.1% TFA). MS m/z ($MH^+$) 487.2.

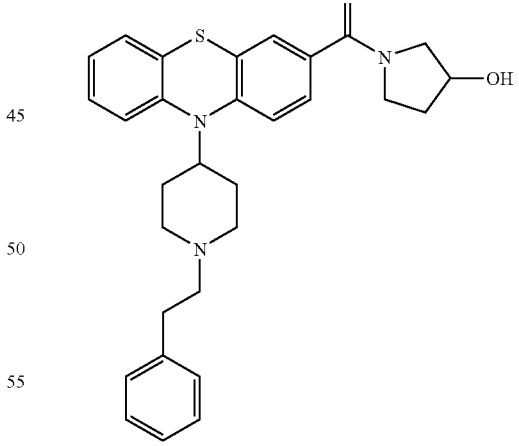

(3-Hydroxypyrrolidin-1-yl)-[10-(1-phenethyl-piperidin-4-yl)-10H-phenothiazin-3-yl]-methanone, 6m Using an adaptation of the method described in Procedure 20, substituting 3-bromo-10-(1-phenethyl-piperidin-4-yl)-10H-phenothiazine, 4f for 3-bromo-10-(1-methylpiperidin-4-yl)-10H-phenothiazine, 4e and 3-hydroxypyrrolidine for pyrrolidine, the title compound (3-hydroxypyrrolidin-1-yl)-[10-(1-phenethyl-piperidin-4-yl)-10H-phenothiazin-3-yl]-methanone, 6m was obtained as a TFA salt after purification via reverse phase HPLC (eluent: $CH_3CN$ in $H_2O$ containing 0.1% TFA). MS m/z (MH$^+$) 500.2.

Example N

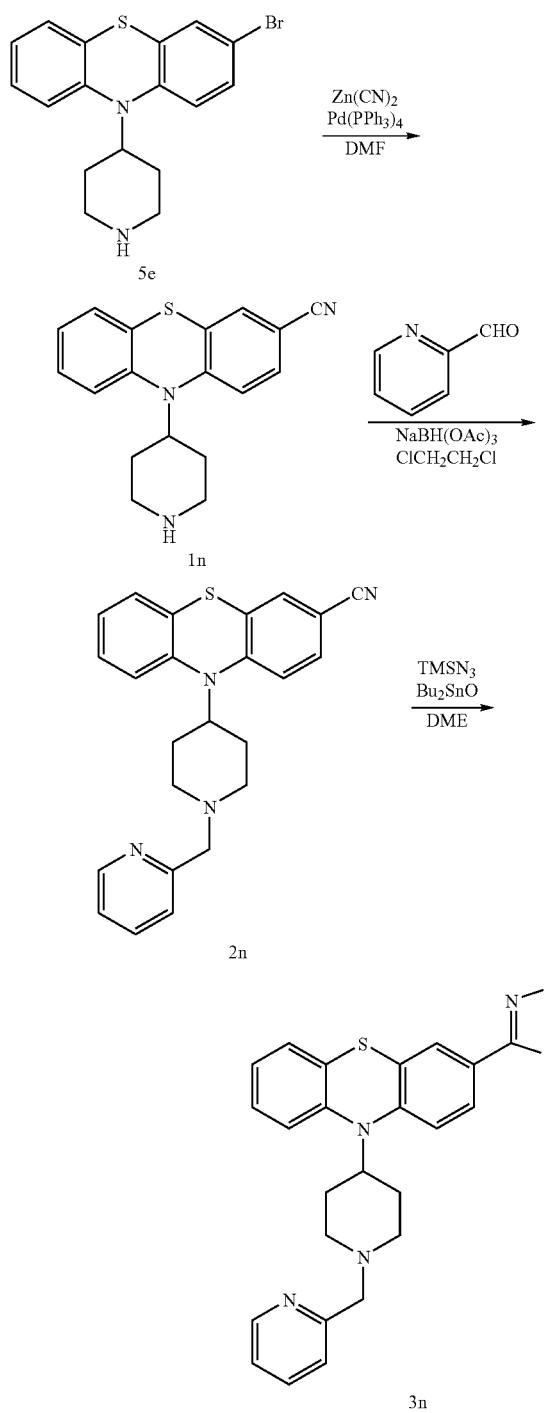

Procedure 21

10-Piperidin-4-yl-10H-phenothiazine-3-carbonitrile, 1n

To a solution of 3-bromo-10-piperidin-4-yl-10H-phenothiazine, 5e (120 mg, 0.33 mmol) in DMF (1.5 mL) was added zinc cyanide (39 mg, 0.33 mmol) and tetrakistriphenylphosphine palladium (19 mg, 0.0165 mmol), the solution was purged with nitrogen, and the mixture was heated in the microwave for 6 min at 160° C. The mixture was allowed to cool to rt, and purified via reverse phase HPLC (eluent: $CH_3CN$ in water containing 0.1% TFA) to yield title compound 10-piperidin-4-yl-10H-phenothiazine-3-carbonitrile, 1n as a TFA salt. MS m/z (MH$^+$) 308.1.

10-(1-Pyridin-2-ylmethyl-piperidin-4-yl)-10H-phenothiazine-3-carbonitrile, 2n Using an adaptation of the method described in Procedure 7, substituting 10-piperidin-4-yl-10H-phenothiazine-3-carbonitrile, 1n for the TFA salt of 10-piperidin-4-yl-3-(1H-tetrazol-5-yl)-10H-phenoxazine, 6a, 2-pyridyl carboxaldehyde for 1H-imidazole-2-carboxaldehyde, and sodium triacetoxyborohydride for tetramethyl-ammonium borohydride, the title compound 10-(1-pyridin-2-ylmethyl-piperidin-4-yl)-10H-phenothiazine-3-carbonitrile, 2n (MS m/z (MH$^+$) 399.2). The material was used as such for the next reaction.

Procedure 22

10-(1-Pyridin-2-ylmethyl-piperidin-4-yl)-3-(1H-tetrazol-5-yl)-10H-phenothiazine, 3n To a solution of 10-(1-pyridin-2-ylmethyl-piperidin-4-yl)-10H-phenothiazine-3-carbonitrile, 2n (79.7 mg, 0.2 mmol) in dimethoxyethane was added trimethylsilyl azide (0.092 g, 0.8 mmol) and dibutyltin oxide (10 mg, 0.04 mmol), and the mixture was heated in a microwave for 15 min at 150° C. The mixture was allowed to cool to rt, and purified via reverse phase HPLC (eluent: $CH_3CN$ in water containing 0.1% TFA) to yield title compound 10-(1-pyridin-2-ylmethyl-piperidin-4-yl)-3-(1H-tetrazol-5-yl)-10H-phenothiazine, 3n as a TFA salt. MS m/z (MH$^+$) 442.2.

10-Piperidin-4-yl-3-(1H-tetrazol-5-yl)-10H-phenothiazine, 4n

Using an adaptation of the method described in Procedure 22, substituting 10-piperidin-4-yl-10H-phenothiazine-3-carbonitrile, 1n for 10-(1-pyridin-2-ylmethyl-piperidin-4-yl)-10H-phenothiazine-3-carbonitrile, 2n, the title compound 10-piperidin-4-yl-3-(1H-tetrazol-5-yl)-10H-phenothiazine, 4n was obtained as a TFA salt. MS m/z (MH+) 351.1.

Example O

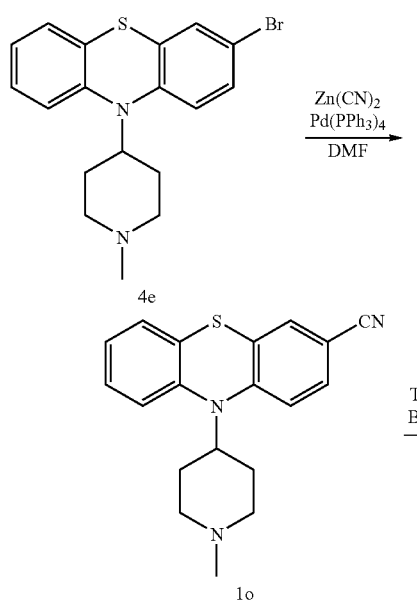

10-(1-Methyl-piperidin-4-yl)-10H-phenothiazine-3-carbonitrile, 1o

Using an adaptation of the method described in Procedure 21, substituting 3-bromo-10-(1-methylpiperidin-4-yl)-10H-phenothiazine, 4e for 3-bromo-10-piperidin-4-yl-10H-phenothiazine, 5e, the title compound 10-(1-methyl-piperidin-4-yl)-10H-phenothiazine-3-carbonitrile, 1o was obtained as a TFA salt. MS m/z (MH+) 322.1.

10-(1-Methyl-piperidin-4-yl)-3-(1H-tetrazol-5-yl)-10H-phenothiazine, 2o

Using an adaptation of the method described in Procedure 22, substituting 10-(1-methyl-piperidin-4-yl)-10H-phenothiazine-3-carbonitrile, 1o for 10-(1-pyridin-2-ylmethyl-piperidin-4-yl)-10H-phenothiazine-3-carbonitrile, 2n, the title compound 10-(1-methyl-piperidin-4-yl)-3-(1H-tetrazol-5-yl)-10H-phenothiazine, 2o was obtained as a TFA salt. MS m/z (MH+) 365.1.

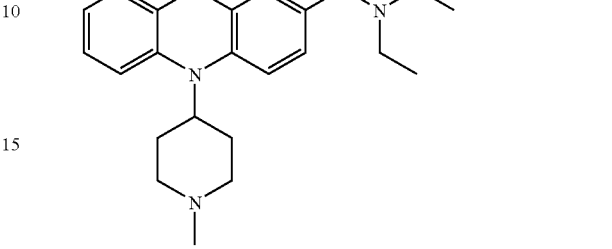

N,N-Diethyl-10-(1-methyl-piperidin-4-yl)-10H-phenothiazine-3-carboxamidine, 3o

Using an adaptation of the method described in Procedure 10, substituting 10-(1-methyl-piperidin-4-yl)-10H-phenothiazine-3-carbonitrile, 1o for 4-(3-cyano-phenoxazin-10-yl)-piperidine-1-carboxylic acid tert-butyl ester, 4a, the title compound N,N-diethyl-10-(1-methyl-piperidin-4-yl)-10H-phenothiazine-3-carboxamidine, 3o was obtained as a TFA salt after purification via reverse phase HPLC (eluent: CH3CN in water containing 0.1% TFA). MS m/z (MH+) 395.2.

Example P

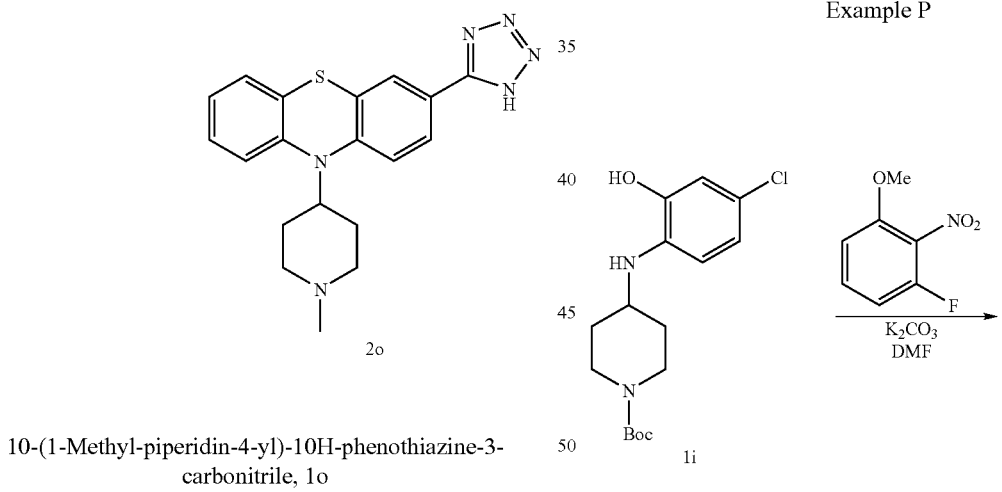

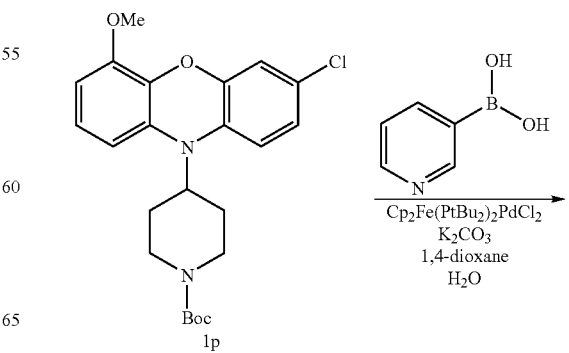

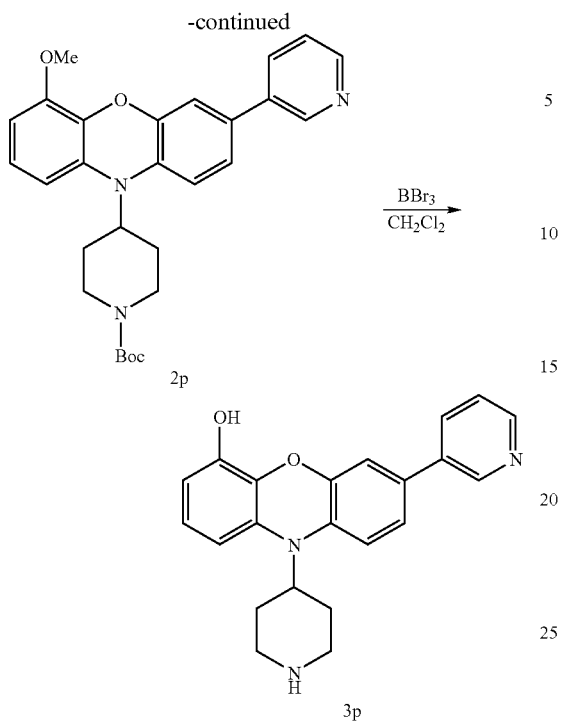

4-(3-Chloro-6-methoxy-phenoxazin-10-yl)-piperidine-1-carboxylic acid tert-butyl ester, 1p Using an adaptation of the method described in Procedure 1, substituting 4-(4-chloro-2-hydroxyphenylamino)-piperidine-1-carboxylic acid tert-butyl ester, 1i, for 2-bromophenol, and 6-fluoro-2-methoxynitrobenzene for 3-fluoro-4-nitrobenzonitrile, the title compound 4-(3-chloro-6-methoxy-phenoxazin-10-yl)-piperidine-1-carboxylic acid tert-butyl ester, 1p was obtained.

4-(6-Methoxy-3-pyridin-3-yl-phenoxazin-10-yl)-piperidine-1-carboxylic acid tert-butyl ester, 2p Using an adaptation of the method described in Procedure 16, substituting 4-(3-chloro-6-methoxy-phenoxazin-10-yl)-piperidine-1-carboxylic acid tert-butyl ester, 1p, for 3-bromo-10-piperidin-4-yl-10H-phenothiazine, 5e, $Cp_2Fe(PtBu_2)_2PdCl_2$ for $Pd(PPh_3)_4$ and a 5:1 mixture of dioxane:water for NMP, the title compound 4-(6-methoxy-3-pyridin-3-yl-phenoxazin-10-yl)-piperidine-1-carboxylic acid tert-butyl ester, 2p was obtained. MS m/z (MH$^+$) 474.

10-Piperidin-4-yl-7-pyridin-3-yl-10H-phenoxazin-4-ol, 3p

Using an adaptation of the method described in Procedure 13, substituting 4-(6-methoxy-3-pyridin-3-yl-phenoxazin-10-yl)-piperidine-1-carboxylic acid tert-butyl ester, 2p, for 10-(1-benzyl-piperidin-4-yl)-6-methoxy-10H-phenoxazine-3-carboxylic acid diethylamide, 4d, the title compound 10-piperidin-4-yl-7-pyridin-3-yl-10H-phenoxazin-4-ol, 3p was obtained as a TFA salt after purification via reverse phase HPLC (eluent: CH$_3$CN in water containing 0.1% TFA). MS m/z (MH$^+$) 359.9.

10-Piperidin-4-yl-7-pyridin-4-yl-10H-phenoxazin-4-ol, 4p and 6-Methoxy-10-piperidin-4-yl-3-pyridin-4-yl-10H-phenoxazine, 5p Using an adaptation of the methods described in Procedures 16 and 13, substituting 4-(3-chloro-6-methoxy-phenoxazin-10-yl)-piperidine-1-carboxylic acid tert-butyl ester, 1p, for 3-bromo-10-piperidin-4-yl-10H-phenothiazine, 5e, 4-pyridyl boronic acid for 3-pyridyl boronic acid, $Cp_2Fe(PtBu_2)_2PdCl_2$ for $Pd(PPh_3)_4$ and a 5:1 mixture of dioxane:water for NMP in Procedure 16, a mixture of title compounds 10-piperidin-4-yl-7-pyridin-4-yl-10H-phenoxazin-4-ol, 4p and 6-methoxy-10-piperidin-4-yl-3-pyridin-4-yl-10H-phenoxazine, 5p, was obtained. Compounds 4p and 5p were separated via reverse phase HPLC (eluent: CH$_3$CN in water containing 0.1% TFA) to yield pure 10-piperidin-4-yl-7-pyridin-4-yl-10H-phenoxazin-4-ol, 4p (first eluting) and 6-methoxy-10-piperidin-4-yl-3-pyridin-4-yl-10H-phenoxazine, 5p (second eluting) as TFA salts. 4p: MS m/z (MH$^+$) 360; 5p: MS m/z (MH$^+$) 374.

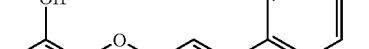

N-[2-(6-Hydroxy-10-piperidin-4-yl-10H-phenoxazin-3-yl)-phenyl]-acetamide, 6p Using an adaptation of the methods described in Procedures 16 and 13, substituting substituting 4-(3-chloro-6-methoxy-phenoxazin-10-yl)-piperidine-1-carboxylic acid tert-butyl ester, 1p, for 3-bromo-10-piperidin-4-yl-10H-phenothiazine, 5e, N-[2-(4,4,5,5-tetramethyl-[1,3,2]dioxaborolan-2-yl)-phenyl]-acetamide for 3-pyridyl boronic acid, $Cp_2Fe(PtBu_2)_2PdCl_2$ for $Pd(PPh_3)_4$ and a 5:1 mixture of dioxane:water for NMP in Procedure 16, the title compound N-[2-(6-hydroxy-10-piperidin-4-yl-10H-phenoxazin-3-yl)-phenyl]-acetamide, 6p was obtained as a TFA salt after purification via reverse phase HPLC (eluent: $CH_3CN$ in water containing 0.1% TFA). MS m/z ($MH^+$) 416.

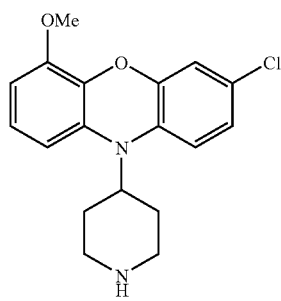

7p

3-Chloro-6-methoxy-10-piperidin-4-yl-10H-phenoxazine, 7p

Using an adaptation of the method described in Procedure 6, substituting 4-(3-chloro-6-methoxy-phenoxazin-10-yl)-piperidine-1-carboxylic acid tert-butyl ester, 1p, for 4-[3-(1H-tetrazol-5-yl)-phenoxazin-10-yl]-piperidine-1-carboxylic acid tert-butyl ester, 5a, and a mixture of TFA in methylene chloride for a 4N hydrochloric acid solution, the title compound 3-chloro-6-methoxy-10-piperidin-4-yl-10H-phenoxazine, 7p was obtained as a TFA salt after purification via reverse phase HPLC (eluent gradient: $CH_3CN$ in water containing 0.1% TFA).
MS m/z ($MH^+$) 330.9.

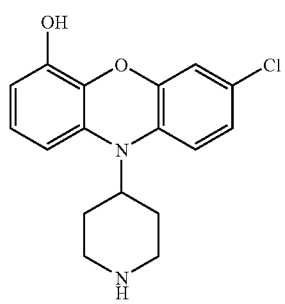

8p

7-Chloro-10-piperidin-4-yl-10H-phenoxazin-4-ol, 8p

Using an adaptation of the method described in Procedure 13, substituting 4-(3-chloro-6-methoxy-phenoxazin-10-yl)-piperidine-1-carboxylic acid tert-butyl ester, 1p, for 10-(1-benzyl-piperidin-4-yl)-6-methoxy-10H-phenoxazine-3-carboxylic acid diethylamide, 4d, the title compound 7-chloro-10-piperidin-4-yl-10H-phenoxazin-4-ol, 8p was obtained as a TFA salt after purification via reverse phase HPLC (eluent: $CH_3CN$ in water containing 0.1% TFA). MS m/z ($MH^+$) 316.8.

Example Q

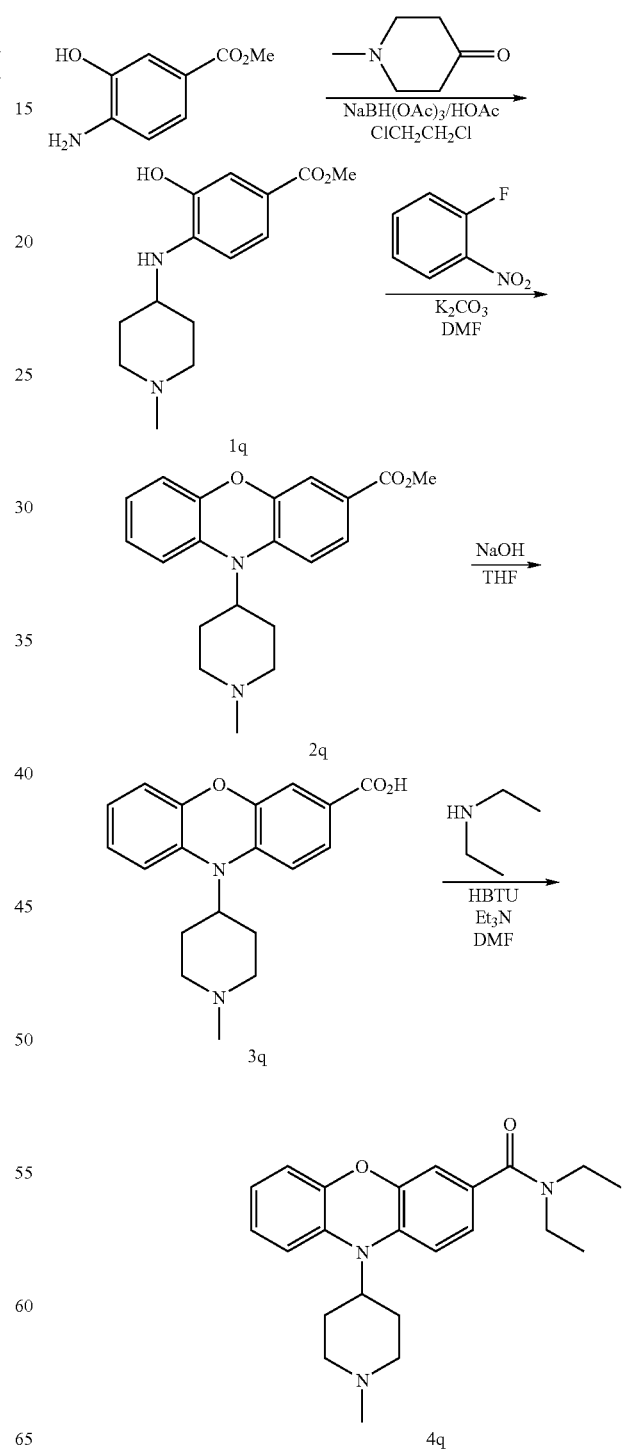

3-Hydroxy-4-(1-methyl-piperidin-4-ylamino)-benzoic acid methyl ester, 1q

Using an adaptation of the method described in Procedure 3, substituting 4-amino-3-hydroxybenzoic acid methyl ester for 4-amino-3-(2-bromophenoxy)-benzonitrile and 1-methyl-piperidin-4-one for 4-oxo-piperidine-1-carboxylic acid tert-butyl ester, the title compound 3-hydroxy-4-(1-methyl-piperidin-4-ylamino)-benzoic acid methyl ester, 1q was obtained.

10-(1-Methyl-piperidin-4-yl)-10H-phenoxazine-3-carboxylic acid methyl ester, 2q Using an adaptation of the method described in Procedure 1, substituting 3-hydroxy-4-(1-methyl-piperidin-4-ylamino)-benzoic acid methyl ester, 1q for 2-bromophenol and 2-fluoronitrobenzene for 3-fluoro-4-nitrobenzonitrile, the title compound 10-(1-methyl-piperidin-4-yl)-10H-phenoxazine-3-carboxylic acid methyl ester, 2q was obtained as a TFA salt after purification via reverse phase HPLC (eluent: $CH_3CN$ in water containing 0.1% TFA). MS m/z ($MH^+$) 338.9.

10-(1-Methyl-piperidin-4-yl)-10H-phenoxazine-3-carboxylic acid, 3q

Using an adaptation of the method described in Procedure 11, substituting 10-(1-methyl-piperidin-4-yl)-10H-phenoxazine-3-carboxylic acid methyl ester, 2q for 10-(1-benzyl-piperidin-4-yl)-6-methoxy-10H-phenoxazine-3-carboxylic acid methyl ester, 2d, and THF for dioxane, the title compound 10-(1-methyl-piperidin-4-yl)-10H-phenoxazine-3-carboxylic acid, 3q was obtained as a TFA salt after purification via reverse phase HPLC (eluent: $CH_3CN$ in water containing 0.1% TFA). MS m/z ($MH^+$) 325.2.

10-(1-Methyl-piperidin-4-yl)-10H-phenoxazine-3-carboxylic acid diethylamide, 4q Using an adaptation of the method described in Procedure 12, substituting the TFA salt of 10-(1-methyl-piperidin-4-yl)-10H-phenoxazine-3-carboxylic acid, 3q for 10-(1-benzyl-piperidin-4-yl)-6-methoxy-10H-phenoxazine-3-carboxylic acid, 3d, and HBTU for HATU, the title compound 10-(1-methyl-piperidin-4-yl)-10H-phenoxazine-3-carboxylic acid diethylamide, 4q was obtained as a TFA salt after purification via reverse phase HPLC (eluent: $CH_3CN$ in water containing 0.1% TFA). MS m/z ($MH^+$) 380.2.

(3-(S)-Hydroxypyrrolidin-1-yl)-[10-(1-methyl-piperidin-4-yl)-10H-phenoxazin-3-yl]-methanone, 5q Using an adaptation of the method described in Procedure 12, substituting the TFA salt of 10-(1-methyl-piperidin-4-yl)-10H-phenoxazine-3-carboxylic acid, 3q for 10-(1-benzyl-piperidin-4-yl)-6-methoxy-10H-phenoxazine-3-carboxylic acid, 3d, 3-(S)-hydroxypyrrolidine for N,N-diethylamine, and HBTU for HATU, the title compound (3-(S)-Hydroxypyrrolidin-1-yl)-[10-(1-methyl-piperidin-4-yl)-10H-phenoxazin-3-yl]-methanone, 5q was obtained as a TFA salt after purification via reverse phase HPLC (eluent: $CH_3CN$ in water containing 0.1% TFA). MS m/z ($MH^+$) 394.2.

Example R

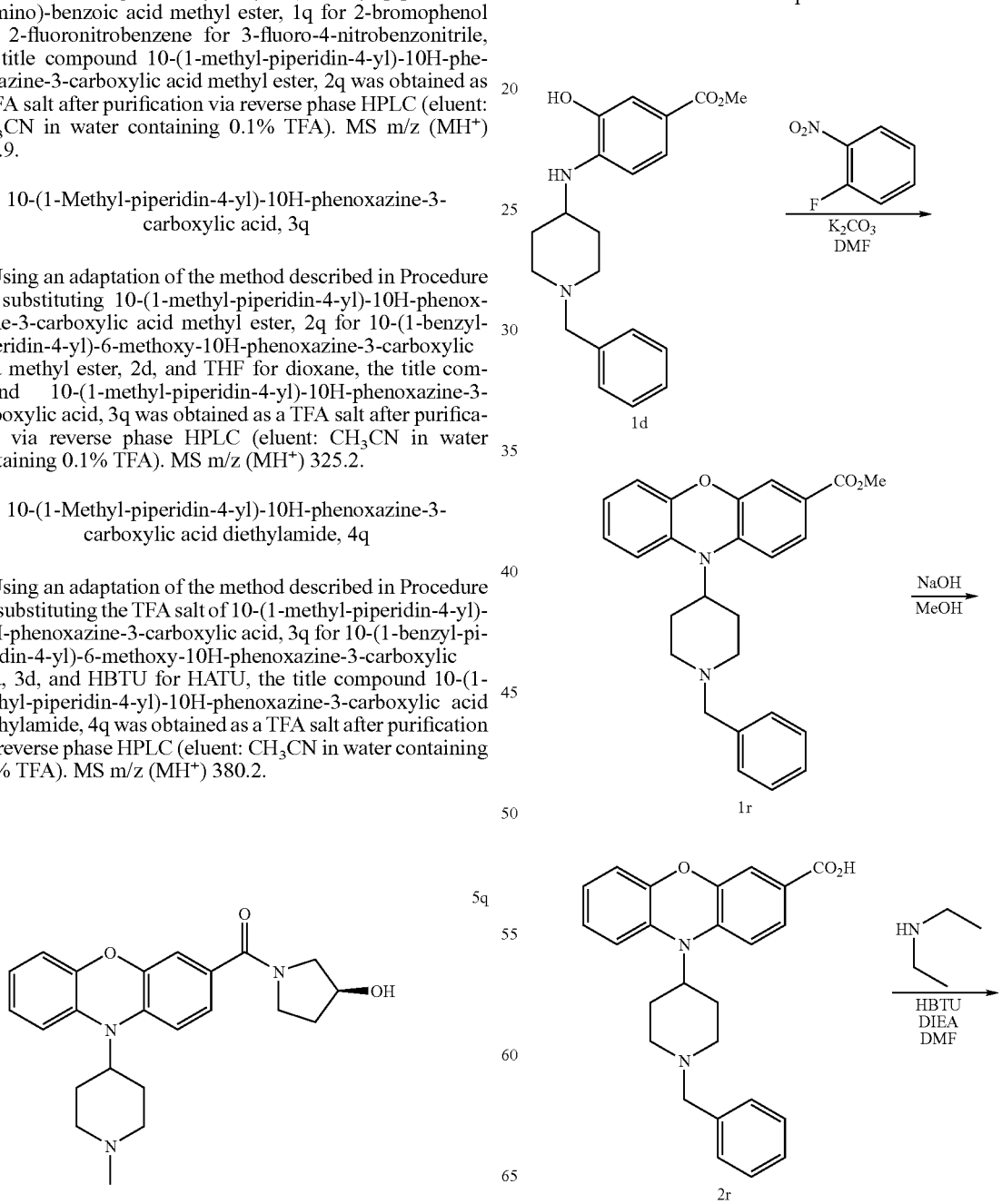

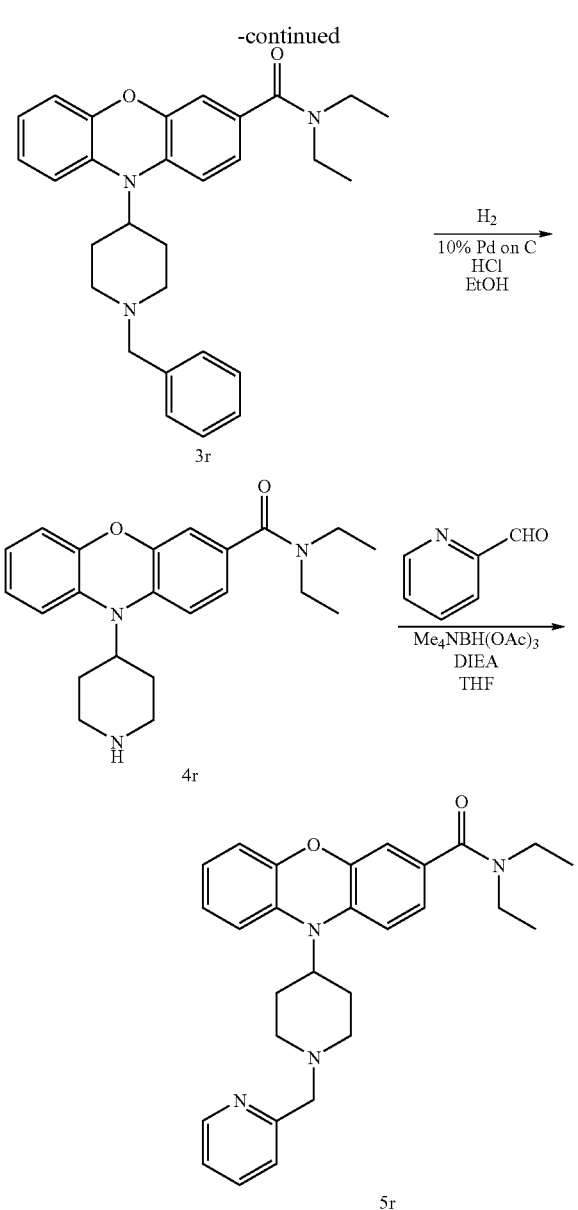

(1-benzyl-piperidin-4-yl)-6-methoxy-10H-phenoxazine-3-carboxylic acid methyl ester, 2d, and methanol for dioxane, the title compound 10-(1-benzyl-piperidin-4-yl)-10H-phenoxazine-3-carboxylic acid, 2r was obtained as a TFA salt after purification via reverse phase HPLC (eluent: $CH_3CN$ in water containing 0.1% TFA). MS m/z ($MH^+$) 401.1.

10-(1-Benzyl-piperidin-4-yl)-10H-phenoxazine-3-carboxylic acid diethylamide, 3r Using an adaptation of the method described in Procedure 12, substituting the TFA salt of 10-(1-benzyl-piperidin-4-yl)-10H-phenoxazine-3-carboxylic acid, 2r for 10-(1-benzyl-piperidin-4-yl)-6-methoxy-10H-phenoxazine-3-carboxylic acid, 3d, and HBTU for HATU, the title compound 10-(1-benzyl-piperidin-4-yl)-10H-phenoxazine-3-carboxylic acid diethylamide, 3r was obtained as a TFA salt after purification via reverse phase HPLC (eluent: $CH_3CN$ in water containing 0.1% TFA). MS m/z ($MH^+$) 456.3.

10-Piperidin-4-yl-10H-phenoxazine-3-carboxylic acid diethylamide, 4r

Using an adaptation of the method described in Procedure 18, substituting the TFA salt of 10-(1-benzyl-piperidin-4-yl)-10H-phenoxazine-3-carboxylic acid diethylamide, 3r for 2-hydroxy-3-nitrobenzoic acid methyl ester, and in the presence of 1N HCl, the title compound 10-piperidin-4-yl-10H-phenoxazine-3-carboxylic acid diethylamide, 4r was obtained as a TFA salt after purification via reverse phase HPLC (eluent: $CH_3CN$ in water containing 0.1% TFA). MS m/z ($MH^+$) 366.1.

10-(1-Pyridin-2-ylmethyl-piperidin-4-yl)-10H-phenoxazine-3-carboxylic acid diethylamide, 5r Using an adaptation of the method described in Procedure 7, substituting the TFA salt of 10-piperidin-4-yl-10H-phenoxazine-3-carboxylic acid diethylamide, 4r for 10-piperidin-4-yl-3-(1H-tetrazol-5-yl)-10H-phenoxazine, 6a, 2-pyridylcarboxaldehyde for 1H-imidazole-2-carboxaldehyde, tetrahydrofuran for dichloroethane, and in the presence of N,N-diisopropyl-N-ethylamine, the title compound 10-(1-pyridin-2-ylmethyl-piperidin-4-yl)-10H-phenoxazine-3-carboxylic acid diethylamide, 5r was obtained as a TFA salt after purification via reverse phase HPLC (eluent: $CH_3CN$ in water containing 0.1% TFA). MS m/z ($MH^+$) 457.1.

10-(1-Benzyl-piperidin-4-yl)-10H-phenoxazine-3-carboxylic acid methyl ester, 1r Using an adaptation of the method described in Procedure 1, substituting 4-(1-benzyl-piperidin-4-ylamino)-3-hydroxybenzoic acid methyl ester, 1d for 2-bromophenol and 2-fluoronitrobenzene for 3-fluoro-4-nitrobenzonitrile, the title compound 10-(1-benzyl-piperidin-4-yl)-10H-phenoxazine-3-carboxylic acid methyl ester, 1r was obtained as a TFA salt after purification via reverse phase HPLC (eluent: $CH_3CN$ in water containing 0.1% TFA).

10-(1-Benzyl-piperidin-4-yl)-10H-phenoxazine-3-carboxylic acid, 2r

Using an adaptation of the method described in Procedure 11, substituting the TFA salt of 10-(1-benzyl-piperidin-4-yl)-10H-phenoxazine-3-carboxylic acid methyl ester, 1r for 10-

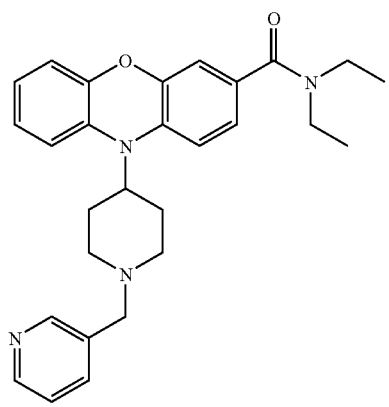

10-(1-Pyridin-3-ylmethyl-piperidin-4-yl)-10H-phenoxazine-3-carboxylic acid diethylamide, 6r Using an adaptation of the method described in Procedure 7, substituting the TFA salt of 10-piperidin-4-yl-10H-phenoxazine-3-carboxylic acid diethylamide, 4r for 10-piperidin-4-yl-3-(1H-tetrazol-5-yl)-10H-phenoxazine, 6a, 3-pyridylcarboxaldehyde for 1H-imidazole-2-carboxaldehyde, tetrahydrofuran for dichloroethane, and in the presence of N,N-diisopropyl-N-ethylamine, the title compound 10-(1-pyridin-3-ylmethyl-piperidin-4-yl)-10H-phenoxazine-3-carboxylic acid diethylamide, 6r was obtained as a TFA salt after purification via reverse phase HPLC (eluent: CH$_3$CN in water containing 0.1% TFA). MS m/z (MH$^+$) 457.1.

10-[1-(3-Methyl-but-2-enyl)-piperidin-4-yl]-10H-phenoxazine-3-carboxylic acid diethylamide, 8r Using an adaptation of the method described in Procedure 7, substituting the TFA salt of 10-piperidin-4-yl-10H-phenoxazine-3-carboxylic acid diethylamide, 4r for 10-piperidin-4-yl-3-(1H-tetrazol-5-yl)-10H-phenoxazine, 6a, 3-methyl-but-2-enal for 1H-imidazole-2-carboxaldehyde, tetrahydrofuran for dichloroethane, and in the presence of N,N-diisopropyl-N-ethylamine, the title compound 10-[1-(3-methyl-but-2-enyl)-piperidin-4-yl]-10H-phenoxazine-3-carboxylic acid diethylamide, 8r was obtained as a TFA salt after purification via reverse phase HPLC (eluent: CH$_3$CN in water containing 0.1% TFA). MS m/z (MH$^+$) 434.1.

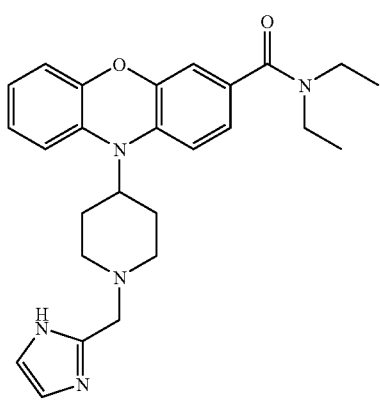

7r

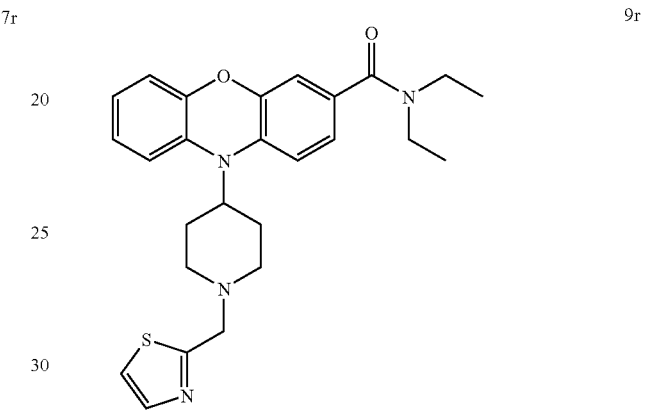

9r

10-[1-(1H-Imidazol-2-ylmethyl)-piperidin-4-yl]-10H-phenoxazine-3-carboxylic acid diethylamide, 7r Using an adaptation of the method described in Procedure 7, substituting the TFA salt of 10-piperidin-4-yl-10H-phenoxazine-3-carboxylic acid diethylamide, 4r for 10-piperidin-4-yl-3-(1H-tetrazol-5-yl)-10H-phenoxazine, 6a, tetrahydrofuran for dichloroethane, and in the presence of N,N-diisopropyl-N-ethylamine, the title compound 10-[1-(1H-imidazol-2-ylmethyl)-piperidin-4-yl]-10H-phenoxazine-3-carboxylic acid diethylamide, 7r was obtained as a TFA salt after purification via reverse phase HPLC (eluent: CH$_3$CN in water containing 0.1% TFA). MS m/z (MH$^+$) 446.1.

10-(1-Thiazol-2-ylmethyl-piperidin-4-yl)-10H-phenoxazine-3-carboxylic acid diethylamide, 9r Using an adaptation of the method described in Procedure 7, substituting the TFA salt of 10-piperidin-4-yl-10H-phenoxazine-3-carboxylic acid diethylamide, 4r for 10-piperidin-4-yl-3-(1H-tetrazol-5-yl)-10H-phenoxazine, 6a, thiazole-2-carboxaldehyde for 1H-imidazole-2-carboxaldehyde, tetrahydrofuran for dichloroethane, and in the presence of N,N-diisopropyl-N-ethylamine, the title compound 10-(1-thiazol-2-ylmethyl-piperidin-4-yl)-10H-phenoxazine-3-carboxylic acid diethylamide, 9r was obtained as a TFA salt after purification via reverse phase HPLC (eluent: CH$_3$CN in water containing 0.1% TFA). MS m/z (MH$^+$) 463.

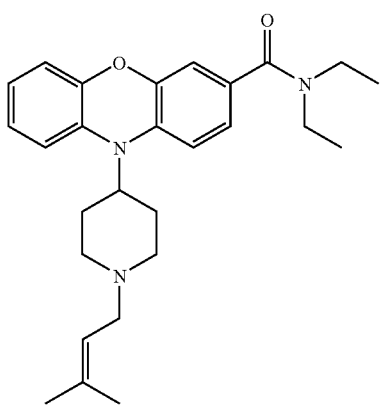

8r

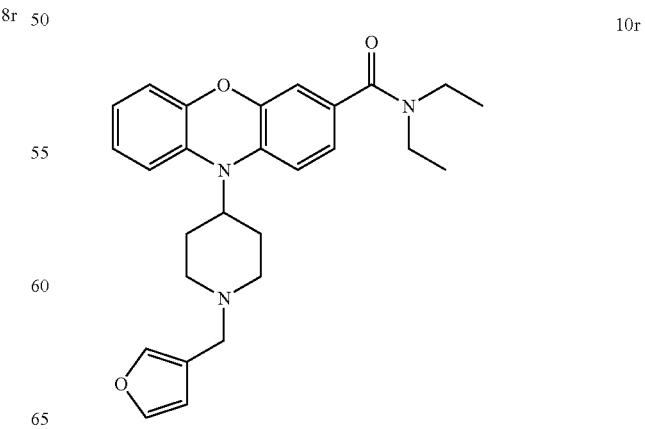

10r

10-(1-Furan-3-ylmethyl-piperidin-4-yl)-10H-phenoxazine-3-carboxylic acid diethylamide, 10r Using an adaptation of the method described in Procedure 7, substituting the TFA salt of 10-piperidin-4-yl-10H-phenoxazine-3-carboxylic acid diethylamide, 4r for 10-piperidin-4-yl-3-(1H-tetrazol-5-yl)-10H-phenoxazine, 6a, 3-furylcarboxaldehyde for 1H-imidazole-2-carboxaldehyde, tetrahydrofuran for dichloroethane, and in the presence of N,N-diisopropyl-N-ethylamine, the title compound 10-(1-furan-3-ylmethyl-piperidin-4-yl)-10H-phenoxazine-3-carboxylic acid diethylamide, 10r was obtained as a TFA salt after purification via reverse phase HPLC (eluent: CH$_3$CN in water containing 0.1% TFA). MS m/z (MH$^+$) 446.1.

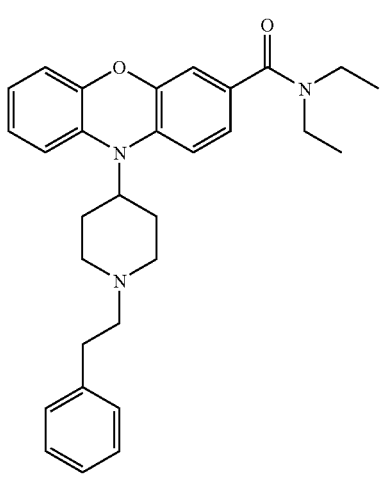

10-(1-Phenethyl-piperidin-4-yl)-10H-phenoxazine-3-carboxylic acid diethylamide, 11r Using an adaptation of the method described in Procedure 7, substituting the TFA salt of 10-piperidin-4-yl-10H-phenoxazine-3-carboxylic acid diethylamide, 4r for 10-piperidin-4-yl-3-(1H-tetrazol-5-yl)-10H-phenoxazine, 6a, phenylacetaldehyde for 1H-imidazole-2-carboxaldehyde, tetrahydrofuran for dichloroethane, and in the presence of N,N-diisopropyl-N-ethylamine, the title compound 10-(1-phenethyl-piperidin-4-yl)-10H-phenoxazine-3-carboxylic acid diethylamide, 11r was obtained as a TFA salt after purification via reverse phase HPLC (eluent: CH$_3$CN in water containing 0.1% TFA). MS m/z (MH$^+$) 470.1.

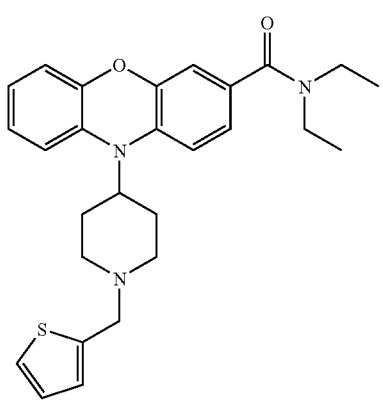

10-(1-Thiophen-2-ylmethyl-piperidin-4-yl)-10H-phenoxazine-3-carboxylic acid diethylamide, 12r Using an adaptation of the method described in Procedure 7, substituting the TFA salt of 10-piperidin-4-yl-10H-phenoxazine-3-carboxylic acid diethylamide, 4r for 10-piperidin-4-yl-3-(1H-tetrazol-5-yl)-10H-phenoxazine, 6a, 2-thiophenecarboxaldehyde for 1H-imidazole-2-carboxaldehyde, tetrahydrofuran for dichloroethane, and in the presence of N,N-diisopropyl-N-ethylamine, the title compound 10-(1-thiophen-2-ylmethyl-piperidin-4-yl)-10H-phenoxazine-3-carboxylic acid diethylamide, 12r was obtained as a TFA salt after purification via reverse phase HPLC (eluent: CH$_3$CN in water containing 0.1% TFA). MS m/z (MH$^+$) 462.

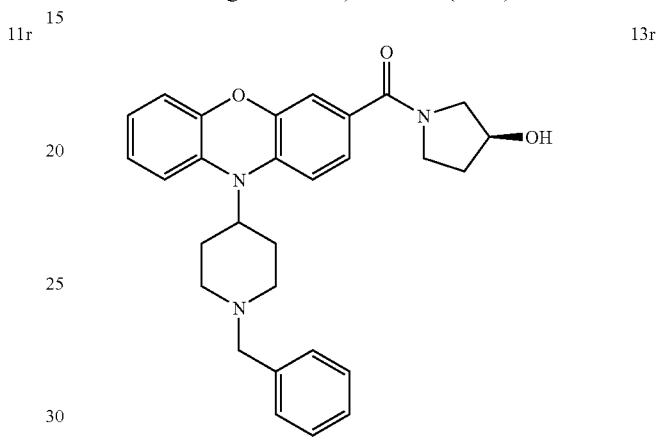

[10-(1-Benzyl-piperidin-4-yl)-10H-phenoxazin-3-yl]-(3-(S)-Hydroxypyrrolidin-1-yl)-methanone, 13r Using an adaptation of the method described in Procedure 12, substituting the TFA salt of 10-(1-benzyl-piperidin-4-yl)-10H-phenoxazine-3-carboxylic acid, 2r for 10-(1-benzyl-piperidin-4-yl)-6-methoxy-10H-phenoxazine-3-carboxylic acid, 3d, 3-(S)-hydroxypyrrolidine for N,N-diethylamine, and HBTU for HATU, the title compound [10-(1-benzyl-piperidin-4-yl)-10H-phenoxazin-3-yl]-(3-(S)-Hydroxypyrrolidin-1-yl)-methanone, 13r was obtained as a TFA salt after purification via reverse phase HPLC (eluent: CH$_3$CN in water containing 0.1% TFA). MS m/z (MH$^+$) 470.1.

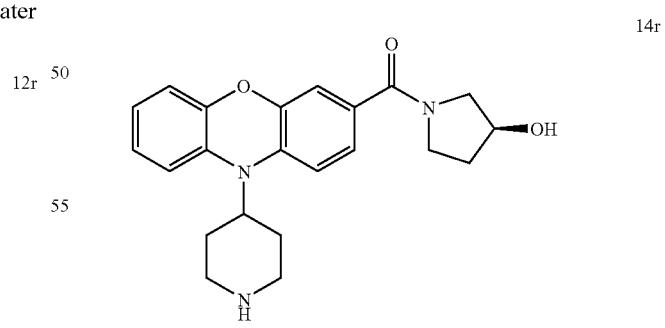

(3-(S)-Hydroxypyrrolidin-1-yl)-(10-piperidin-4-yl-10H-phenoxazin-3-yl)-methanone, 14r Using an adaptation of the method described in Procedure 18, substituting the TFA salt of [10-(1-benzyl-piperidin-4-yl)-10H-phenoxazin-3-yl]-(3-(S)-Hydroxypyrrolidin-1-yl)- methanone, 13r for 2-hydroxy-3-nitrobenzoic acid methyl ester, and in the presence of 1N HCl, the title compound (3-(S)-Hydroxypyrrolidin-1-yl)-(10-piperidin-4-yl-10H-phenoxazin-3-yl)-methanone, 14r was obtained as a TFA salt after purification via reverse phase HPLC (eluent: CH$_3$CN in water containing 0.1% TFA). MS m/z (MH$^+$) 380.

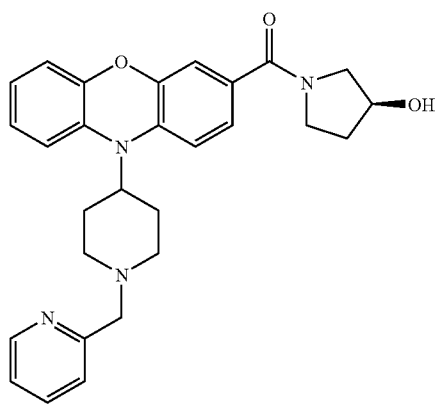

(3-(S)-Hydroxypyrrolidin-1-yl)-[10-(1-pyridin-2-ylmethyl-piperidin-4-yl)-10H-phenoxazin-3-yl]-methanone, 15r Using an adaptation of the method described in Procedure 7, substituting the TFA salt of (3-(S)-Hydroxypyrrolidin-1-yl)-(10-piperidin-4-yl-10H-phenoxazin-3-yl)-methanone, 14r for 10-piperidin-4-yl-3-(1H-tetrazol-5-yl)-10H-phenoxazine, 6a, 2-pyridylcarboxaldehyde for 1H-imidazole-2-carboxaldehyde, tetrahydrofuran for dichloroethane, and in the presence of N,N-diisopropyl-N-ethylamine, the title compound (3-(S)-Hydroxypyrrolidin-1-yl)-[10-(1-pyridin-2-ylmethyl-piperidin-4-yl)-10H-phenoxazin-3-yl]-methanone, 15r was obtained as a TFA salt after purification via reverse phase HPLC (eluent: CH$_3$CN in water containing 0.1% TFA). MS m/z (MH$^+$) 471.

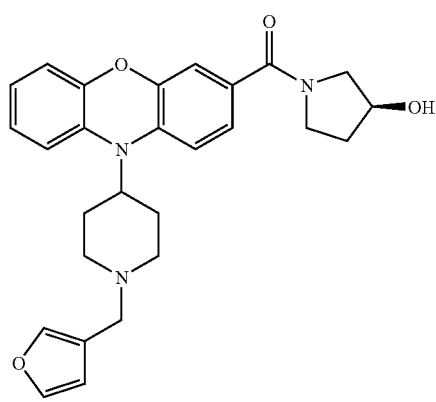

[10-(1-Furan-3-ylmethyl-piperidin-4-yl)-10H-phenoxazin-3-yl]-(3-(S)-Hydroxypyrrolidin-1-yl)-methanone, 16r Using an adaptation of the method described in Procedure 7, substituting the TFA salt of (3-(S)-Hydroxypyrrolidin-1-yl)-(10-piperidin-4-yl-10H-phenoxazin-3-yl)-methanone, 14r for 10-piperidin-4-yl-3-(1H-tetrazol-5-yl)-10H-phenoxazine, 6a, 3-furylcarboxaldehyde for 1H-imidazole-2-carboxaldehyde, tetrahydrofuran for dichloroethane, and in the presence of N,N-diisopropyl-N-ethylamine, the title compound [10-(1-furan-3-ylmethyl-piperidin-4-yl)-10H-phenoxazin-3-yl]-(3-(S)-Hydroxypyrrolidin-1-yl)-methanone, 16r was obtained as a TFA salt after purification via reverse phase HPLC (eluent: CH$_3$CN in water containing 0.1% TFA). MS m/z (MH$^+$) 460.

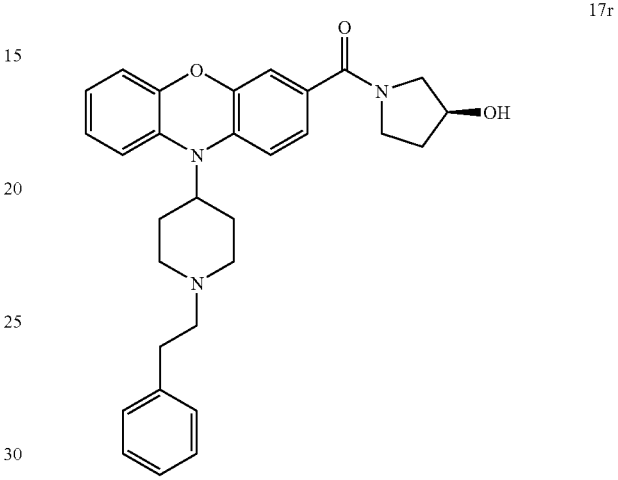

(3-(S)-Hydroxypyrrolidin-1-yl)-[10-(1-phenethyl-piperidin-4-yl)-10H-phenoxazin-3-yl]-methanone, 17r Using an adaptation of the method described in Procedure 7, substituting the TFA salt of (3-(S)-Hydroxypyrrolidin-1-yl)-(10-piperidin-4-yl-10H-phenoxazin-3-yl)-methanone, 14r for 10-piperidin-4-yl-3-(1H-tetrazol-5-yl)-10H-phenoxazine, 6a, phenylacetaldehyde for 1H-imidazole-2-carboxaldehyde, tetrahydrofuran for dichloroethane, and in the presence of N,N-diisopropyl-N-ethylamine, the title compound (3-(S)-Hydroxypyrrolidin-1-yl)-[10-(1-phenethyl-piperidin-4-yl)-10H-phenoxazin-3-yl]-methanone, 17r was obtained as a TFA salt after purification via reverse phase HPLC (eluent: CH$_3$CN in water containing 0.1% TFA). MS m/z (MH$^+$) 484.1.

Example S

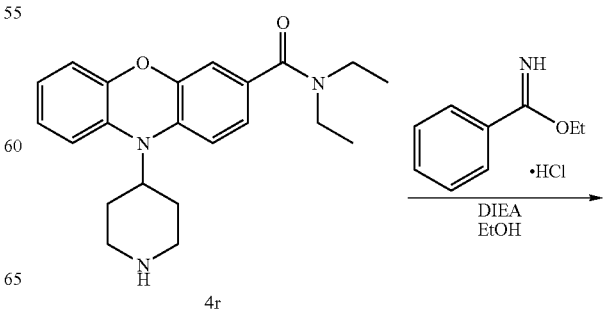

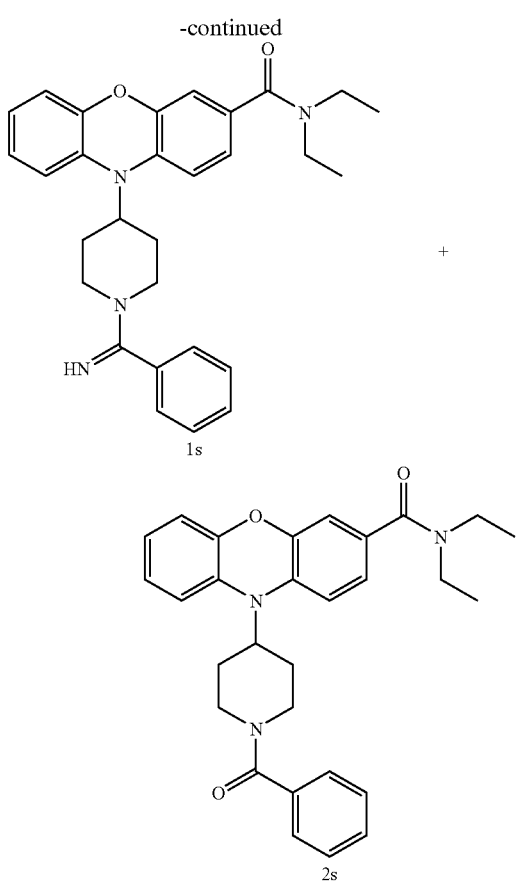

Procedure 23

10-[1-(Iminophenylmethyl)-piperidin-4-yl]-10H-phenoxazine-3-carboxylic acid diethylamide, 1s (JNJ-39020930) and 10-(1-Benzoyl-piperidin-4-yl)-10H-phenoxazine-3-carboxylic acid diethylamide, 2s To a solution of the TFA salt of 10-piperidin-4-yl-10H-phenoxazine-3-carboxylic acid diethylamide, 4r (80 mg, 0.167 mmol) in ethanol was added benzimidic acid ethyl ester (223 mg, 1.2 mmol) N,N-diisopropyl-N-ethylamine (172 mg, 1.3 mmol), and the mixture was heated to 40° C. for 24 h. The solvent was removed via evaporation, and the residue was purified via reverse phase HPLC yielding a mixture of target compound 10-[1-(iminophenylmethyl)-piperidin-4-yl]-10H-phenoxazine-3-carboxylic acid diethylamide, 1s (first eluting product) as a TFA salt and 10-(1-benzoyl-piperidin-4-yl)-10H-phenoxazine-3-carboxylic acid diethylamide, 2s (second eluting product) as a free base. 1s: MS m/z (MH$^+$) 469.1; 2s: MS m/z (MH$^+$) 470.

Biological Examples

Rat Brain Delta Opioid Receptor Binding Assay

Procedure: Male, Wistar rats (150-250 g, VAF, Charles River, Kingston, N.Y.) were killed by $CO_2$, and their brains were removed and placed immediately in ice cold Tris HCl buffer (50 mM, pH 7.4). The forebrains were separated from the remainder of the brain by a coronal transection, beginning dorsally at the colliculi and passing ventrally through the midbrain-pontine junction. After dissection, the forebrains were homogenized in Tris buffer in a Teflon®-glass homogenizer. The homogenate was diluted to a concentration of 1 g of forebrain tissue per 80 mL Tris and centrifuged at 39,000×g for 10 min. The pellet was resuspended in the same volume of Tris buffer containing 5 mM $MgCl_2$ with several brief pulses from a Polytron homogenizer. This particulate preparation was used for the delta opioid binding assays. Following incubation with the delta selective peptide ligand ~4 nM [$^3$H]DPDPE or 0.15 nM [$^3$H]naltrindole at 25° C. for 2.5 h in a 96-well plate with total volume of 1 mL, the plate contents were filtered through Wallac filtermat B sheets on a Tomtec 96-well harvester. The filters were rinsed three times with 2 mL of 10 mM HEPES (pH 7.4), and dried in a 650 W microwave oven for 1.75 min twice. To each sample area 2×50 μL of Betaplate Scint scintillation fluid (LKB) was added and the radioactivity was quantified on a LKB (Wallac) 1205 BetaPlate liquid scintillation counter.

Analysis: The data from the scintillation counter was used to calculate either the % inhibition compared to control binding (when only a single concentration of test compound was evaluated) or a $K_i$ value (when a range of concentrations was tested). Percent inhibition was calculated as: [(total dpm−test compound dpm)/(total dpm−nonspecific dpm)]*100. Kd and Ki values can be calculated using GraphPad PRISM data analysis program. The data obtained are shown in Table 1, below.

Rat Brain Mu Opioid Receptor Binding Assay

Procedure: Male, Wistar rats (150-250 g, VAF, Charles River, Kingston, N.Y.) were killed by $CO_2$, and their brains were removed and placed immediately in ice cold Tris HCl buffer (50 mM, pH 7.4). The forebrains can be separated from the remainder of the brain by a coronal transection, beginning dorsally at the colliculi and passing ventrally through the midbrain-pontine junction. After dissection, the forebrains were homogenized in Tris buffer in a Teflon®-glass homogenizer. The homogenate was diluted to a concentration of 1 g of forebrain tissue per 80 mL Tris and centrifuged at 39,000×g for 10 min. The pellet was resuspended in the same volume of Tris buffer containing 5 mM $MgCl_2$ with several brief pulses from a Polytron homogenizer. This particulate preparation was used for the mu opioid binding assays. Following incubation with the mu selective peptide ligand, ~0.8 nM [$^3$H]DAMGO, at 25° C. for 2.5 h in a 96-well plate with total assay volume of 1 mL, the plate contents were filtered through Wallac filtermat B sheets on a Tomtec 96-well harvester. The filters were rinsed three times with 2 mL of 10 mM HEPES (pH 7.4), and dried in a 650 W microwave oven for 1.75 min twice. To each sample area 2×40 μL of Betaplate Scint scintillation fluid (LKB) was added and the radioactivity was quantifed on a LKB (Wallac) 1205 BetaPlate liquid scintillation counter.

Analysis: The data from the scintillation counter was used to calculate either the % inhibition compared to control binding (when only a single concentration of test compound was evaluated) or a $K_i$ value (when a range of concentrations was tested). Percent inhibition was calculated as: [(total dpm−test compound dpm)/(total dpm−nonspecific dpm)]*100. Kd and Ki values were calculated using GraphPad PRISM data analysis program. The data obtained are shown in Table 1, below.

[$^{35}$S]GTPγS Binding Assay in NG108-15 Cell Membranes (Delta Opioid)

Methods: NG108-15 cell membranes were purchased from Applied Cell Sciences (Rockville, Md.). 8 mg/mL of membrane protein was suspended in 10 mM TRIS-HCl pH 7.2, 2 mM EDTA, 10% sucrose. Membranes were maintained at 4-8° C. A 1 mL volume of membranes was added into 10 mL cold binding assay buffer. The assay buffer contained 50 mM Tris, pH 7.6, 5 mM MgCl$_2$, 100 mM NaCl, 1 mM DTT and 1 mM EGTA. The membrane suspension was homogenized twice with a Polytron, and centrifuged at 3000 rpm for 10 min. The supernatant was then centrifuged at 18,000 rpm for 20 min. Ten mL assay buffer was added into the pellet containing tube. The pellet and buffer were mixed with a Polytron.

Incubation procedure: The pellet membranes (75 µg/mL) were preincubated with SPA (10 mg/mL) at 25° C. for 45 min in the assay buffer. The SPA (5 mg/mL) coupled with membranes (37.5 µg/mL) was then incubated with 0.1 nM [$^{35}$S]GTPγS in the same Tris buffer containing 100 µM GDP in a total volume of 200 µL. Increasing concentrations of receptor agonists were used to stimulate [$^{35}$S]-GTPγS binding. The basal binding was tested in the absence of agonists and non-specific binding was tested in the presence of 10 µM unlabeled GTPγS. The data were analyzed on a Packard Top Count.

DATA

% of Basal=(stimulated−non specific)*100/(basal−non specific).

EC$_{50}$ value values were calculated using GraphPad Prism. The data obtained are shown in Table 1, below.

[$^{35}$S]GTPγS Binding Assays in CHO-hMOR Cell Membranes

Methods: CHO-hMOR cell membranes were purchased from Receptor Biology, Inc. (Baltimore, Md.). About 10 mg/mL of membrane protein was suspended in 10 mM TRIS-HCl pH 7.2, 2 mM EDTA, 10% sucrose, and the suspension was kept on ice. A 1 mL volume of membranes was added to 15 mL cold binding assay buffer containing 50 mM HEPES, pH 7.6, 5 mM MgCl$_2$, 100 mM NaCl, 1 mM DTT and 1 mM EDTA. The membrane suspension was homogenized with a Polytron and centrifuged at 3,000 rpm for 10 min. The supernatant was then centrifuged at 18,000 rpm for 20 min. The pellet was resuspended in 10 mL assay buffer with a Polytron. The membranes were preincubated with wheat germ agglutinin coated SPA beads (Amersham) at 25° C. for 45 min in the assay buffer. The SPA bead (5 mg/mL) coupled membranes (10 µg/mL) were then incubated with 0.5 nM [$^{35}$S]GTPγS in the assay buffer. The basal binding was that taking place in the absence of added test compound; this unmodulated binding was considered as 100%, with agonist stimulated binding rising to levels significantly above this value. A range of concentrations of receptor agonist was used to stimulate [$^{35}$S]GTPγS binding. Both basal and non-specific binding was tested in the absence of agonist; non-specific binding determination included 10 µM unlabeled GTPγS.

Compounds were tested for function as antagonists by evaluating their potential to inhibit agonist-stimulated GTPγS binding. Radioactivity was quantified on a Packard Top-Count. The following parameters were calculated:

$$\% \text{ stimulation} = \frac{(\text{test compound cpm} - \text{non-specific cpm})}{(\text{basal cpm} - \text{non-specific cpm})} \times 100$$

$$\% \text{ inhibition} = \frac{(\% \text{ stimulation by } 1\mu M \text{ DAMGO} - \% \text{ stimulation by test compound})}{(\% \text{ stimulation by } 1\ \mu M \text{ DAMGO} - 100)} \times 100$$

EC$_{50}$ values were calculated using GraphPad Prism. The data obtained are shown in Table 1, below.

TABLE 1

| Compound | Ex # | delta (Ki, nM) | mu (Ki, nM) | delta GTPγS EC50 (nM) | delta GTPγS Rel Eff | mu GTPγS EC50 (nM) |
|---|---|---|---|---|---|---|
| 10-(1-Benzyl-piperidin-4-yl)-6-hydroxy-10H-phenoxazine-3-carboxylic acid diethylamide | 6d | 0.10 | | | | |
| 10-(1-Benzylpiperidin-4-yl)-10H-phenoxazine-3,6-dicarboxylic acid 6-amide 3-diethylamide | 5l | 0.10 | | | | |
| 10-(1-Benzyl-piperidin-4-yl)-6-hydroxy-10H-phenoxazine-3-carboxylic acid dimethylamide | 7d | 0.17 | | | | |
| 3-[10-(1-Thiophen-2-ylmethyl-piperidin-4-yl)-10H-phenoxazin-3-yl]-4H-[1,2,4]oxadiazol-5-one | 5b | 7.08 | | | | |
| 10-(1-Pyridin-2-ylmethyl-piperidin-4-yl)-10H-phenoxazine-3-carboxylic acid diethylamide | 5r | 9.63 | | | | |
| 10-(1-Furan-3-ylmethyl-piperidin-4-yl)-3-(1H-tetrazol-5-yl)-10H-phenoxazine | 8a | 15.41 | | | | |
| 3-[10-(1-Pyridin-2-ylmethyl-piperidin-4-yl)-10H-phenoxazin-3-yl]-4H-[1,2,4]oxadiazol-5-one | 6b | 17.11 | | | | |
| 10-(1-Pyridin-2-ylmethyl-piperidin-4-yl)-3-(1H-tetrazol-5-yl)-10H-phenothiazine | 3n | 24.47 | | | | |

TABLE 1-continued

| Compound | Ex # | delta (Ki, nM) | mu (Ki, nM) | delta GTPγS EC50 (nM) | delta GTPγS Rel Eff | mu GTPγS EC50 (nM) |
|---|---|---|---|---|---|---|
| 10-(1-Pyridin-3-ylmethyl-piperidin-4-yl)-10H-phenoxazine-3-carboxylic acid diethylamide | 6r | 25.53 | | | | |
| N-[2-(6-Hydroxy-10-piperidin-4-yl-10H-phenoxazin-3-yl)-phenyl]-acetamide | 6p | 42.48 | | | | |
| 10-(1-Benzyl-piperidin-4-yl)-6-methoxy-10H-phenoxazine-3-carboxylic acid diethylamide | 4d | 42.75 | | | | |
| 10-Piperidin-4-yl-7-pyridin-3-yl-10H-phenoxazin-4-ol | 3p | 44.34 | | | | |
| 3-[10-(1-Furan-3-ylmethyl-piperidin-4-yl)-10H-phenoxazin-3-yl]-4H-[1,2,4]oxadiazol-5-one | 3b | 47.90 | | | | |
| 10-Piperidin-4-yl-10H-phenoxazine-3,6-dicarboxylic acid 6-amide 3-diethylamide | 6l | 51.24 | | | | |
| N-[2-(10-Piperidin-4-yl-10H-phenothiazin-3-yl)-phenyl]-acetamide | 5g | 57.23 | 1966 | | | |
| N-[2-(10-Piperidin-4-yl-10H-phenoxazin-3-yl)-phenyl]-acetamide | 2j | 75.04 | | | | |
| 10-(1-Benzyl-piperidin-4-yl)-7-bromo-10H-phenoxazine-4-carboxylic acid amide | 8l | 83.56 | | | | |
| 10-[1-(1H-Imidazol-2-ylmethyl)-piperidin-4-yl]-10H-phenoxazine-3-carboxylic acid diethylamide | 7r | 98.70 | | | | |
| 10-(1-Benzyl-piperidin-4-yl)-10H-phenoxazine-3-carboxylic acid diethylamide | 3r | 100 | 1649 | | | |
| 10-(1-Methyl-piperidin-4-yl)-10H-phenoxazine-3-carboxylic acid diethylamide | 4r | 124 | | | | |
| 10-[1-(3-Methyl-but-2-enyl)-piperidin-4-yl]-10H-phenoxazine-3-carboxylic acid diethylamide | 8r | 164 | | | | |
| 10-Piperidin-4-yl-3-pyridin-3-yl-10H-phenoxazine | 4i | 164 | | | | |
| N,N-Diethyl-10-piperidin-4-yl-10H-phenoxazine-3-carboxamidine | 2c | 170 | | | | |
| N-(2-{10-[1-(3-Methyl-but-2-enyl)-piperidin-4-yl]-10H-phenothiazin-3-yl}-phenyl)-acetamide | 8g | 183 | 1313 | | | |
| [10-(1-Furan-3-ylmethyl-piperidin-4-yl)-10H-phenoxazin-3-yl]-(3-(S)-hydroxypyrrolidin-1-yl)-methanone | 16r | 189 | | | | |
| (3-(S)-Hydroxypyrrolidin-1-yl)-[10-(1-pyridin-2-ylmethyl-piperidin-4-yl)-10H-phenoxazin-3-yl]-methanone | 15r | 203 | | | | |
| 10-Piperidin-4-yl-3-(1H-tetrazol-5-yl)-10H-phenoxazine | 6a | 220 | 1352 | | | |
| 10-(1-Benzyl-piperidin-4-yl)-7-bromo-10H-phenoxazine-4-carboxylic acid | 7l | 223 | | | | |
| N-{2-[10-(1-Methyl-piperidin-4-yl)-10H-phenothiazin-3-yl]-phenyl}-acetamide | 4g | 225 | 3717 | | | |
| 10-(1-Pyridin-2-ylmethyl-piperidin-4-yl)-3-(1H-tetrazol-5-yl)-10H-phenoxazine | 10a | 227 | | | | |
| (3-Hydroxypyrrolidin-1-yl)-[10-(1-pyridin-2-ylmethyl-piperidin-4-yl)-10H-phenothiazin-3-yl]-methanone | 5m | 242 | | | | |
| N-(2-{10-[1-(1H-Imidazol-2-ylmethyl)-piperidin-4-yl]-10H-phenoxazin-3-yl}-phenyl)-acetamide | 7j | 249 | | | | |
| N,N-Diethyl-10-(1-furan-3-ylmethyl-piperidin-4-yl)-10H-phenoxazine-3-carboxamidine | 3c | 254 | | | | |
| N-{2-[10-(1-Pyridin-2-ylmethyl-piperidin-4-yl)-10H-phenothiazin-3-yl]-phenyl}-acetamide | 6g | 255 | 837 | | | |

TABLE 1-continued

| Compound | Ex # | delta (Ki, nM) | mu (Ki, nM) | delta GTPγS EC50 (nM) | delta GTPγS Rel Eff | mu GTPγS EC50 (nM) |
|---|---|---|---|---|---|---|
| N,N-Diethyl-10-(1-pyridin-2-ylmethyl-piperidin-4-yl)-10H-phenoxazine-3-carboxamidine | 5c | 258 | | | | |
| 3-(10-Piperidin-4-yl-10H-phenoxazin-3-yl)-4H-[1,2,4]oxadiazol-5-one | 2b | 259 | 1694 | | | |
| N,N-Diethyl-10-(1-phenethyl-piperidin-4-yl)-10H-phenoxazine-3-carboxamidine | 4c | 266 | | | | |
| 10-(1-Thiazol-2-ylmethyl-piperidin-4-yl)-10H-phenoxazine-3-carboxylic acid diethylamide | 9r | 300 | | | | |
| 10-(1-Methyl-piperidin-4-yl)-10H-phenoxazine-3-carboxylic acid diethylamide | 4q | 358 | >10000 | | | |
| 3-Pyridin-3-yl-10-(1-pyridin-2-ylmethyl-piperidin-4-yl)-10H-phenothiazine | 2f | 365 | 2852 | | | |
| 10-(1-Benzyl-piperidin-4-yl)-6-methoxy-10H-phenoxazine-3-carboxylic acid dimethylamide | 5d | 374 | | | | |
| 10-[1-(Imino-phenyl-methyl)-piperidin-4-yl]-10H-phenoxazine-3-carboxylic acid diethylamide | 1s | 382 | | | | |
| N-{2-[10-(1-Benzyl-piperidin-4-yl)-10H-phenoxazin-3-yl]-phenyl}-acetamide | 5h | 400 | 3325 | | | |
| 3-[10-(1-Phenethyl-piperidin-4-yl)-10H-phenoxazin-3-yl]-4H-[1,2,4]oxadiazol-5-one | 4b | 401 | | | | |
| 10-Piperidin-4-yl-10H-phenoxazine-3-carbonitrile | 11a | 436 | 5816 | 1928 | 0.45 | >10,000 |
| [10-(1-Benzyl-piperidin-4-yl)-10H-phenoxazin-3-yl]-(3-(S)-Hydroxypyrrolidin-1-yl)-methanone | 13r | 465 | | | | |
| 10-Piperidin-4-yl-3-pyridin-3-yl-10H-phenothiazine | 6e | 475 | 3066 | | | |
| 10-(1-Phenethyl-piperidin-4-yl)-3-(1H-tetrazol-5-yl)-10H-phenoxazine | 9a | 475 | | | | |
| 10-(1-Furan-3-ylmethyl-piperidin-4-yl)-3-pyridin-3-yl-10H-phenothiazine | 3g | 500 | 964 | | | |
| 10-Piperidin-4-yl-7-pyridin-4-yl-10H-phenoxazin-4-ol | 4p | 535 | | | | |
| 10-Piperidin-4-yl-3-pyridin-4-yl-10H-phenoxazine | 2k | 554 | | | | |
| N-{2-[10-(1-Thiophen-2-ylmethyl-piperidin-4-yl)-10H-phenothiazin-3-yl]-phenyl}-acetamide | 7g | 571 | 4028 | | | |
| N-{2-[10-(1-Pyridin-2-ylmethyl-piperidin-4-yl)-10H-phenoxazin-3-yl]-phenyl}-acetamide | 5j | 576 | | | | |
| 6-Methoxy-10-piperidin-4-yl-3-pyridin-4-yl-10H-phenoxazine | 5p | 589 | | | | |
| 10-(1-Furan-3-ylmethyl-piperidin-4-yl)-10H-phenoxazine-3-carboxylic acid diethylamide | 10r | 655 | | | | |
| 10-[1-(1H-Imidazol-2-ylmethyl)-piperidin-4-yl]-3-(1H-tetrazol-5-yl)-10H-phenoxazine | 7a | 655 | 2768 | | | |
| 10-Piperidin-4-yl-10H-phenoxazine-3-carboxylic acid amide | 12a | 682 | 1243 | 9247 | 0.81 | >10,000 |
| 10-(1-Thiophen-2-ylmethyl-piperidin-4-yl)-10H-phenothiazine-3-carboxylic acid ethylamide | 4m | 784 | | | | |
| N,N-Diethyl-10-(1-methyl-piperidin-4-yl)-10H-phenothiazine-3-carboxamidine | 3o | 1017 | | | | |
| 10-(1-Benzyl-piperidin-4-yl)-3-pyridin-3-yl-10H-phenoxazine | 4h | 1089 | >10000 | | | |
| 10-(1-Methyl-piperidin-4-yl)-10H-phenoxazine-3-carboxylic acid methyl ester | 2q | 1131 | >10000 | | | |

TABLE 1-continued

| Compound | Ex # | delta (Ki, nM) | mu (Ki, nM) | delta GTPγS EC50 (nM) | delta GTPγS Rel Eff | mu GTPγS EC50 (nM) |
|---|---|---|---|---|---|---|
| 10-(1-Phenethyl-piperidin-4-yl)-10H-phenoxazine-3-carboxylic acid diethylamide | 11r | 1177 | | | | |
| 10-(1-Methyl-piperidin-4-yl)-10H-phenothiazine-3-carboxylic acid ethylamide | 2m | 1201 | | | | |
| 3-Pyridin-4-yl-10-(1-pyridin-2-ylmethyl-piperidin-4-yl)-10H-phenoxazine | 5k | 1202 | | | | |
| 10-(1-Furan-3-ylmethyl-piperidin-4-yl)-3-pyridin-4-yl-10H-phenoxazine | 3k | 1229 | | | | |
| 10-(1-Benzyl-piperidin-4-yl)-10H-phenoxazine-3-carboxylic acid | 2r | 1311 | 349 | | | |
| (3-(S)-Hydroxypyrrolidin-1-yl)-(10-piperidin-4-yl-10H-phenoxazin-3-yl)-methanone | 14r | 1334 | | | | |
| N-{2-[10-(1-Thiophen-2-ylmethyl-piperidin-4-yl)-10H-phenoxazin-3-yl]-phenyl}-acetamide | 4j | 1393 | | | | |
| 3-Bromo-10-piperidin-4-yl-10H-phenothiazine | 5e | 1396 | 6936 | | | |
| [10-(1-Methyl-piperidin-4-yl)-10H-phenothiazin-3-yl]-pyrrolidin-1-yl-methanone | 1m | 1439 | | | | |
| 3-Bromo-10-(1-phenethyl-piperidin-4-yl)-10H-phenothiazine | 1g | 1496 | 78 | | | |
| 10-(1-Benzyl-piperidin-4-yl)-3-chloro-10H-phenoxazine | 2h | 1576 | 3705 | | | |
| 10-Piperidin-4-yl-10H-phenothiazine-3-carbonitrile | 1n | 1576 | | | | |
| 10-(1-Thiophen-2-ylmethyl-piperidin-4-yl)-10H-phenoxazine-3-carboxylic acid diethylamide | 12r | 1652 | | | | |
| 3-Chloro-6-methoxy-10-piperidin-4-yl-10H-phenoxazine | 7p | 1746 | | | | |
| 10-(1-Phenethyl-piperidin-4-yl)-3-pyridin-4-yl-10H-phenothiazine | 2g | 2057 | 43 | | | |
| 10-(1-Benzyl-piperidin-4-yl)-3-pyridin-4-yl-10H-phenoxazine | 3h | 2091 | 7108 | | | |
| 10-(1-Phenethyl-piperidin-4-yl)-3-pyridin-4-yl-10H-phenoxazine | 6k | 2125 | | | | |
| 10-Piperidin-4-yl-3-(1H-tetrazol-5-yl)-10H-phenothiazine | 4n | 2239 | | | | |
| N-{2-[10-(1-Furan-3-ylmethyl-piperidin-4-yl)-10H-phenoxazin-3-yl]-phenyl}-acetamide | 3j | 2275 | | | | |
| 10-(1-Methyl-piperidin-4-yl)-10H-phenoxazine-3-carboxylic acid | 3q | 2624 | | | | |
| (3-(S)-Hydroxypyrrolidin-1-yl)-[10-(1-methyl-piperidin-4-yl)-10H-phenoxazin-3-yl]-methanone | 5q | 2628 | >10000 | | | |
| (3-Hydroxypyrrolidin-1-yl)-[10-(1-methylpiperidin-4-yl)-10H-phenothiazin-3-yl]-methanone | 3m | 3150 | | | | |
| (3-(S)-Hydroxypyrrolidin-1-yl)-[10-(1-phenethyl-piperidin-4-yl)-10H-phenoxazin-3-yl]-methanone | 17r | 3169 | | | | |
| (3-Hydroxypyrrolidin-1-yl)-[10-(1-phenethyl-piperidin-4-yl)-10H-phenothiazin-3-yl]-methanone | 6m | 3232 | | | | |
| 3-Pyridin-4-yl-10-(1-thiophen-2-ylmethyl-piperidin-4-yl)-10H-phenoxazine | 4k | 3617 | | | | |
| 10-(1-Methyl-piperidin-4-yl)-3-(1H-tetrazol-5-yl)-10H-phenothiazine | 2o | 3956 | | | | |
| 3-Bromo-10-(1-methylpiperidin-4-yl)-10H-phenothiazine | 4e | 4959 | 6932 | | | |
| 3-Pyridin-3-yl-10-(1-thiophen-2-ylmethyl-piperidin-4-yl)-10H-phenoxazine | 7i | 5132 | | | | |
| N-{2-[10-(1-Phenethyl-piperidin-4-yl)-10H-phenoxazin-3-yl]-phenyl}-acetamide | 6j | 5374 | | | | |

TABLE 1-continued

| Compound | Ex # | delta (Ki, nM) | mu (Ki, nM) | delta GTPγS EC50 (nM) | delta GTPγS Rel Eff | mu GTPγS EC50 (nM) |
|---|---|---|---|---|---|---|
| 10-(1-Methyl-piperidin-4-yl)-10H-phenothiazine-3-carbonitrile | 1o | 6205 | | | | |
| 10-(1-Benzylpiperidin-4-yl)-7-diethylcarbamoyl-10H-phenoxazine-4-carboxylic acid | 4l | 6279 | | | | |
| 10-(1-Phenethyl-piperidin-4-yl)-3-pyridin-3-yl-10H-phenoxazine | 8i | >10000 | | | | |
| 3-Pyridin-3-yl-10-(1-pyridin-2-ylmethyl-piperidin-4-yl)-10H-phenoxazine | 6i | >10000 | | | | |
| 10-(1-Furan-3-ylmethyl-piperidin-4-yl)-3-pyridin-3-yl-10H-phenoxazine | 5i | >10000 | | | | |
| 7-Chloro-10-piperidin-4-yl-10H-phenoxazin-4-ol | 8p | >10000 | | | | |
| 10-(1-Benzoyl-piperidin-4-yl)-10H-phenoxazine-3-carboxylic acid diethylamide | 2s | >10000 | | | | |

We claim:
1. A compound that is:
10-(1-Benzyl-piperidin-4-yl)-6-hydroxy-10H-phenoxazine-3-carboxylic acid diethylamide;
10-(1-Benzylpiperidin-4-yl)-10H-phenoxazine-3,6-dicarboxylic acid 6-amide 3-diethylamide;
10-(1-Benzyl-piperidin-4-yl)-6-hydroxy-10H-phenoxazine-3-carboxylic acid dimethylamide;
3-[10-(1-Thiophen-2-ylmethyl-piperidin-4-yl)-10H-phenoxazin-3-yl]-4H-[1,2,4]oxadiazol-5-one;
10-(1-Pyridin-2-ylmethyl-piperidin-4-yl)-10H-phenoxazine-3-carboxylic acid diethylamide;
10-(1-Furan-3-ylmethyl-piperidin-4-yl)-3-(1H-tetrazol-5-yl)-10H-phenoxazine;
3-[10-(1-Pyridin-2-ylmethyl-piperidin-4-yl)-10H-phenoxazin-3-yl]-4H-[1,2,4]oxadiazol-5-one;
10-(1-Pyridin-2-ylmethyl-piperidin-4-yl)-3-(1H-tetrazol-5-yl)-10H-phenothiazine;
10-(1-Pyridin-3-ylmethyl-piperidin-4-yl)-10H-phenoxazine-3-carboxylic acid diethylamide;
N-[2-(6-Hydroxy-10-piperidin-4-yl-10H-phenoxazin-3-yl)-phenyl]-acetamide;
10-(1-Benzyl-piperidin-4-yl)-6-methoxy-10H-phenoxazine-3-carboxylic acid diethylamide;
10-Piperidin-4-yl-7-pyridin-3-yl-10H-phenoxazin-4-ol;
3-[10-(1-Furan-3-ylmethyl-piperidin-4-yl)-10H-phenoxazin-3-yl]-4H-[1,2,4]oxadiazol-5-one;
10-Piperidin-4-yl-10H-phenoxazine-3,6-dicarboxylic acid 6-amide 3-diethylamide;
N-[2-(10-Piperidin-4-yl-10H-phenothiazin-3-yl)-phenyl]-acetamide;
N-[2-(10-Piperidin-4-yl-10H-phenoxazin-3-yl)-phenyl]-acetamide;
10-(1-Benzyl-piperidin-4-yl)-7-bromo-10H-phenoxazine-4-carboxylic acid amide;
10-[1-(1H-Imidazol-2-ylmethyl)-piperidin-4-yl]-10H-phenoxazine-3-carboxylic acid diethylamide;
10-(1-Benzyl-piperidin-4-yl)-10H-phenoxazine-3-carboxylic acid diethylamide;
10-(1-Methyl-piperidin-4-yl)-10H-phenoxazine-3-carboxylic acid diethylamide;
10-[1-(3-Methyl-but-2-enyl)-piperidin-4-yl]-10H-phenoxazine-3-carboxylic acid diethylamide;
10-Piperidin-4-yl-3-pyridin-3-yl-10H-phenoxazine;
N,N-Diethyl-10-piperidin-4-yl-10H-phenoxazine-3-carboxamidine;
N-(2-{10-[1-(3-Methyl-but-2-enyl)-piperidin-4-yl]-10H-phenothiazin-3-yl}-phenyl)-acetamide;
[10-(1-Furan-3-ylmethyl-piperidin-4-yl)-10H-phenoxazin-3-yl]-(3-(S)-hydroxypyrrolidin-1-yl)-methanone;
(3-(S)-Hydroxypyrrolidin-1-yl)-[10-(1-pyridin-2-ylmethyl-piperidin-4-yl)-10H-phenoxazin-3-yl]-methanone;
10-Piperidin-4-yl-3-(1H-tetrazol-5-yl)-10H-phenoxazine;
10-(1-Benzyl-piperidin-4-yl)-7-bromo-10H-phenoxazine-4-carboxylic acid;
N-{2-[10-(1-Methyl-piperidin-4-yl)-10H-phenothiazin-3-yl]-phenyl}-acetamide;
10-(1-Pyridin-2-ylmethyl-piperidin-4-yl)-3-(1H-tetrazol-5-yl)-10H-phenoxazine;
(3-Hydroxypyrrolidin-1-yl)-[10-(1-pyridin-2-ylmethyl-piperidin-4-yl)-10H-phenothiazin-3-yl]-methanone;
N-(2-{10-[1-(1H-Imidazol-2-ylmethyl)-piperidin-4-yl]-10H-phenoxazin-3-yl}-phenyl)-acetamide;
N,N-Diethyl-10-(1-furan-3-ylmethyl-piperidin-4-yl)-10H-phenoxazine-3-carboxamidine;
N-{2-[10-(1-Pyridin-2-ylmethyl-piperidin-4-yl)-10H-phenothiazin-3-yl]-phenyl}-acetamide;
N,N-Diethyl-10-(1-pyridin-2-ylmethyl-piperidin-4-yl)-10H-phenoxazine-3-carboxamidine;
3-(10-Piperidin-4-yl-10H-phenoxazin-3-yl)-4H-[1,2,4]oxadiazol-5-one;
N,N-Diethyl-10-(1-phenethyl-piperidin-4-yl)-10H-phenoxazine-3-carboxamidine;
10-(1-Thiazol-2-ylmethyl-piperidin-4-yl)-10H-phenoxazine-3-carboxylic acid diethylamide;
10-(1-Methyl-piperidin-4-yl)-10H-phenoxazine-3-carboxylic acid diethylamide;
3-Pyridin-3-yl-10-(1-pyridin-2-ylmethyl-piperidin-4-yl)-10H-phenothiazine;
10-(1-Benzyl-piperidin-4-yl)-6-methoxy-10H-phenoxazine-3-carboxylic acid dimethylamide;
10-[1-(Imino-phenyl-methyl)-piperidin-4-yl]-10H-phenoxazine-3-carboxylic acid diethylamide;
N-{2-[10-(1-Benzyl-piperidin-4-yl)-10H-phenoxazin-3-yl]-phenyl}-acetamide;
3-[10-(1-Phenethyl-piperidin-4-yl)-10H-phenoxazin-3-yl]-4H-[1,2,4]oxadiazol-5-one;

10-Piperidin-4-yl-10H-phenoxazine-3-carbonitrile;
[10-(1-Benzyl-piperidin-4-yl)-10H-phenoxazin-3-yl]-(3-(S)-Hydroxypyrrolidin-1-yl)-methanone;
10-Piperidin-4-yl-3-pyridin-3-yl-10H-phenothiazine;
10-(1-Phenethyl-piperidin-4-yl)-3-(1H-tetrazol-5-yl)-10H-phenoxazine;
10-(1-Furan-3-ylmethyl-piperidin-4-yl)-3-pyridin-4-yl-10H-phenothiazine;
10-Piperidin-4-yl-7-pyridin-4-yl-10H-phenoxazin-4-ol;
10-Piperidin-4-yl-3-pyridin-4-yl-10H-phenoxazine;
N-{2-[10-(1-Thiophen-2-ylmethyl-piperidin-4-yl)-10H-phenothiazin-3-yl]-phenyl}-acetamide;
N-{2-[10-(1-Pyridin-2-ylmethyl-piperidin-4-yl)-10H-phenoxazin-3-yl]-phenyl}-acetamide;
6-Methoxy-10-piperidin-4-yl-3-pyridin-4-yl-10H-phenoxazine;
10-(1-Furan-3-ylmethyl-piperidin-4-yl)-10H-phenoxazine-3-carboxylic acid diethylamide;
10-[1-(1H-Imidazol-2-ylmethyl)-piperidin-4-yl]-3-(1H-tetrazol-5-yl)-10H-phenoxazine;
10-Piperidin-4-yl-10H-phenoxazine-3-carboxylic acid amide;
10-(1-Thiophen-2-ylmethyl-piperidin-4-yl)-10H-phenothiazine-3-carboxylic acid ethylamide;
N,N-Diethyl-10-(1-methyl-piperidin-4-yl)-10H-phenothiazine-3-carboxamidine;
10-(1-Benzyl-piperidin-4-yl)-3-pyridin-3-yl-10H-phenoxazine;
10-(1-Methyl-piperidin-4-yl)-10H-phenoxazine-3-carboxylic acid methyl ester;
10-(1-Phenethyl-piperidin-4-yl)-10H-phenoxazine-3-carboxylic acid diethylamide;
10-(1-Methyl-piperidin-4-yl)-10H-phenoxazine-3-carboxylic acid;
10-(1-Methyl-piperidin-4-yl)-10H-phenothiazine-3-carboxylic acid ethylamide;
3-Pyridin-4-yl-10-(1-pyridin-2-ylmethyl-piperidin-4-yl)-10H-phenoxazine;
10-(1-Furan-3-ylmethyl-piperidin-4-yl)-3-pyridin-4-yl-10H-phenoxazine;
10-(1-Benzyl-piperidin-4-yl)-10H-phenoxazine-3-carboxylic acid;
(3-(S)-Hydroxypyrrolidin-1-yl)-(10-piperidin-4-yl-10H-phenoxazin-3-yl)-methanone;
N-{2-[10-(1-Thiophen-2-ylmethyl-piperidin-4-yl)-10H-phenoxazin-3-yl]-phenyl}-acetamide;
3-Bromo-10-piperidin-4-yl-10H-phenothiazine;
[10-(1-Methyl-piperidin-4-yl)-10H-phenothiazin-3-yl]-pyrrolidin-1-yl-methanone;
3-Bromo-10-(1-phenethyl-piperidin-4-yl)-10H-phenothiazine;
10-(1-Benzyl-piperidin-4-yl)-3-chloro-10H-phenoxazine;
10-Piperidin-4-yl-10H-phenothiazine-3-carbonitrile;
10-(1-Thiophen-2-ylmethyl-piperidin-4-yl)-10H-phenoxazine-3-carboxylic acid diethylamide;
3-Chloro-6-methoxy-10-piperidin-4-yl-10H-phenoxazine;
10-(1-Phenethyl-piperidin-4-yl)-3-pyridin-4-yl-10H-phenothiazine;
10-(1-Benzyl-piperidin-4-yl)-3-pyridin-4-yl-10H-phenoxazine;
10-(1-Phenethyl-piperidin-4-yl)-3-pyridin-4-yl-10H-phenoxazine;
10-Piperidin-4-yl-3-(1H-tetrazol-5-yl)-10H-phenothiazine;
N-{2-[10-(1-Furan-3-ylmethyl-piperidin-4-yl)-10H-phenoxazin-3-yl]-phenyl}-acetamide;
10-(1-Methyl-piperidin-4-yl)-10H-phenoxazine-3-carboxylic acid;
(3-(S)-Hydroxypyrrolidin-1-yl)-[10-(1-methyl-piperidin-4-yl)-10H-phenoxazin-3-yl]-methanone;
(3-Hydroxypyrrolidin-1-yl)-[10-(1-methylpiperidin-4-yl)-10H-phenothiazin-3-yl]-methanone;
(3-(S)-Hydroxypyrrolidin-1-yl)-[10-(1-phenethyl-piperidin-4-yl)-10H-phenoxazin-3-yl]-methanone;
(3-Hydroxypyrrolidin-1-yl)-[10-(1-phenethyl-piperidin-4-yl)-10H-phenothiazin-3-yl]-methanone;
3-Pyridin-4-yl-10-(1-thiophen-2-ylmethyl-piperidin-4-yl)-10H-phenoxazine;
10-(1-Methyl-piperidin-4-yl)-3-(1H-tetrazol-5-yl)-10H-phenothiazine;
3-Pyridin-3-yl-10-(1-thiophen-2-ylmethyl-piperidin-4-yl)-10H-phenoxazine;
N-{2-[10-(1-Phenethyl-piperidin-4-yl)-10H-phenoxazin-3-yl]-phenyl}-acetamide;
10-(1-Methyl-piperidin-4-yl)-10H-phenothiazine-3-carbonitrile;
10-(1-Benzylpiperidin-4-yl)-7-diethylcarbamoyl-10H-phenoxazine-4-carboxylic acid;
10-(1-Phenethyl-piperidin-4-yl)-3-pyridin-3-yl-10H-phenoxazine;
3-Pyridin-3-yl-10-(1-pyridin-2-ylmethyl-piperidin-4-yl)-10H-phenoxazine;
10-(1-Furan-3-ylmethyl-piperidin-4-yl)-3-pyridin-3-yl-10H-phenoxazine;
7-Chloro-10-piperidin-4-yl-10H-phenoxazin-4-ol; or
10-(1-Benzoyl-piperidin-4-yl)-10H-phenoxazine-3-carboxylic acid diethylamide.

2. A compound that is:
10-(1-Benzyl-piperidin-4-yl)-6-hydroxy-10H-phenoxazine-3-carboxylic acid diethylamide;
10-(1-Benzylpiperidin-4-yl)-10H-phenoxazine-3,6-dicarboxylic acid 6-amide 3-diethylamide;
10-(1-Benzyl-piperidin-4-yl)-6-hydroxy-10H-phenoxazine-3-carboxylic acid dimethylamide;
3-[10-(1-Thiophen-2-ylmethyl-piperidin-4-yl)-10H-phenoxazin-3-yl]-4H-[1,2,4]oxadiazol-5-one;
10-(1-Pyridin-2-ylmethyl-piperidin-4-yl)-10H-phenoxazine-3-carboxylic acid diethylamide;
10-(1-Furan-3-ylmethyl-piperidin-4-yl)-3-(1H-tetrazol-5-yl)-10H-phenoxazine;
3-[10-(1-Pyridin-2-ylmethyl-piperidin-4-yl)-10H-phenoxazin-3-yl]-4H-[1,2,4]oxadiazol-5-one;
10-(1-Pyridin-2-ylmethyl-piperidin-4-yl)-3-(1H-tetrazol-5-yl)-10H-phenothiazine;
10-(1-Pyridin-3-ylmethyl-piperidin-4-yl)-10H-phenoxazine-3-carboxylic acid diethylamide; or
N-[2-(6-Hydroxy-10-piperidin-4-yl-10H-phenoxazin-3-yl)-phenyl]-acetamide.

3. A pharmaceutical composition comprising a compound or salt according to claim 1 admixed with a pharmaceutically acceptable carrier, excipient or diluent.

4. A veterinary composition comprising a compound or salt according to claim 1 admixed with a veterinarily acceptable carrier, excipient or diluent.

5. A pharmaceutical composition comprising a compound or salt according to claim 2 admixed with a pharmaceutically acceptable carrier, excipient or diluent.

6. A veterinary composition comprising a compound or salt according to claim 2 admixed with a veterinarily acceptable carrier, excipient or diluent.

* * * * *